(12) United States Patent
Richelsoph

(10) Patent No.: US 9,421,041 B2
(45) Date of Patent: Aug. 23, 2016

(54) POLYAXIAL SCREW ASSEMBLY

(76) Inventor: Marc E. Richelsoph, Charlotte, NC (US)

( * ) Notice: Subject to any disclaimer, the term of this patent is extended or adjusted under 35 U.S.C. 154(b) by 968 days.

(21) Appl. No.: 12/556,001

(22) Filed: Oct. 2, 2009

(65) Prior Publication Data

US 2010/0063545 A1    Mar. 11, 2010

(51) Int. Cl.
*A61B 17/70* (2006.01)

(52) U.S. Cl.
CPC ......... *A61B 17/7035* (2013.01); *A61B 17/705* (2013.01); *A61B 17/7014* (2013.01); *A61B 17/7023* (2013.01); *A61B 17/7026* (2013.01); *A61B 17/7037* (2013.01); *A61B 17/7038* (2013.01); *A61B 17/7041* (2013.01)

(58) Field of Classification Search
CPC .......... A61B 17/7052; A61B 17/7014; A61B 17/7032; A61B 17/705; A61B 17/7049; A61B 17/7007; A61B 17/7025; A61B 17/7005; A61B 17/7002; A61B 17/88; A61B 17/7019
USPC ................................ 606/247–278; 403/109.5
See application file for complete search history.

(56) References Cited

U.S. PATENT DOCUMENTS

| | | | |
|---|---|---|---|
| 2,855,232 A | 10/1958 | Kozak | |
| 3,599,245 A | 8/1971 | Blatchford | |
| 3,997,138 A | 12/1976 | Crock et al. | |
| 4,041,939 A | 8/1977 | Hall | |
| 4,269,178 A | 5/1981 | Keene | |
| 4,404,967 A | 9/1983 | Bacal et al. | |
| 4,411,259 A | 10/1983 | Drummond | |
| 4,419,026 A * | 12/1983 | Leto | 403/104 |
| 4,611,581 A | 9/1986 | Steffee | |
| 4,706,367 A * | 11/1987 | Garringer | 29/525.05 |
| 4,836,196 A | 6/1989 | Park et al. | |
| 4,887,595 A | 12/1989 | Heinig et al. | |
| 4,946,458 A | 8/1990 | Harms et al. | |
| 4,947,835 A | 8/1990 | Hepburn et al. | |
| 4,950,269 A | 8/1990 | Gaines, Jr. | |
| 5,010,879 A | 4/1991 | Moriya et al. | |
| 5,036,837 A | 8/1991 | Mitchell et al. | |
| 5,084,048 A | 1/1992 | Jacob et al. | |
| 5,122,131 A | 6/1992 | Tsou | |
| 5,129,899 A | 7/1992 | Small et al. | |

(Continued)

FOREIGN PATENT DOCUMENTS

| WO | 9702786 A1 | 1/1997 |
|---|---|---|
| WO | 0018310 A | 4/2000 |

(Continued)

OTHER PUBLICATIONS

Supplementary European Search Report of European Patent App. No. 09 81 3525 dated Feb. 6, 2013.

(Continued)

*Primary Examiner* — Eduardo C Robert
*Assistant Examiner* — Michelle C Eckman
(74) *Attorney, Agent, or Firm* — Mayback & Hoffman, P.A.; Gregory L. Mayback

(57) ABSTRACT

A polyaxial screw assembly includes an internal load dampening mechanism for sharing and dampening loads between at least one screw member and at least one rod member interconnected by the assembly. A method of interconnecting the orthopedic screw with the rod by dampening with a body member interconnecting the screw to the rod.

11 Claims, 40 Drawing Sheets

(56) References Cited

U.S. PATENT DOCUMENTS

| | | |
|---|---|---|
| 5,176,679 A | 1/1993 | Lin |
| 5,201,734 A | 4/1993 | Cozad et al. |
| 5,261,913 A | 11/1993 | Marnay |
| 5,281,222 A | 1/1994 | Allard et al. |
| 5,356,411 A * | 10/1994 | Spievack .................. 606/63 |
| 5,380,325 A | 1/1995 | Lahille et al. |
| 5,395,371 A | 3/1995 | Miller et al. |
| 5,443,467 A | 8/1995 | Biedermann et al. |
| 5,474,551 A | 12/1995 | Finn et al. |
| 5,476,462 A | 12/1995 | Allard et al. |
| 5,501,684 A | 3/1996 | Schlapfer et al. |
| 5,507,746 A | 4/1996 | Lin |
| 5,516,335 A * | 5/1996 | Kummer et al. ............ 606/63 |
| 5,531,745 A | 7/1996 | Ray |
| 5,531,747 A | 7/1996 | Ray |
| 5,540,690 A | 7/1996 | Miller et al. |
| 5,545,163 A | 8/1996 | Miller et al. |
| 5,549,608 A | 8/1996 | Errico |
| 5,562,660 A | 10/1996 | Grob |
| 5,575,792 A | 11/1996 | Errico et al. |
| 5,578,033 A | 11/1996 | Errico |
| 5,584,834 A | 12/1996 | Errico |
| 5,586,984 A | 12/1996 | Errico et al. |
| 5,591,165 A | 1/1997 | Jackson |
| 5,630,817 A | 5/1997 | Rokegem et al. |
| 5,716,356 A | 2/1998 | Biedermann et al. |
| 5,728,098 A | 3/1998 | Sherman |
| 5,733,284 A | 3/1998 | Martin |
| 5,733,285 A | 3/1998 | Errico et al. |
| 5,879,350 A | 3/1999 | Sherman et al. |
| 5,882,350 A | 3/1999 | Ralph et al. |
| 5,891,145 A | 4/1999 | Morrison |
| 5,954,725 A | 9/1999 | Sherman et al. |
| 5,984,928 A * | 11/1999 | Hermann .................. 606/324 |
| 6,022,350 A | 2/2000 | Ganem |
| 6,045,552 A | 4/2000 | Zucherman et al. |
| 6,063,090 A | 5/2000 | Schlapfer |
| 6,113,601 A | 9/2000 | Tatar |
| 6,132,432 A | 10/2000 | Richelsoph |
| 6,206,879 B1 | 3/2001 | Marnay et al. |
| 6,248,105 B1 | 6/2001 | Schlapfer et al. |
| 6,254,602 B1 | 7/2001 | Justis |
| 6,273,888 B1 | 8/2001 | Justis |
| 6,290,703 B1 | 9/2001 | Ganem |
| 6,302,888 B1 | 10/2001 | Mellinger et al. |
| 6,355,040 B1 | 3/2002 | Richelsoph |
| 6,379,354 B1 | 4/2002 | Rogozinski |
| 6,554,834 B1 | 4/2003 | Crozet et al. |
| 6,582,400 B1 | 6/2003 | Hawk et al. |
| 6,585,737 B1 | 7/2003 | Braccelli et al. |
| 6,623,485 B2 | 9/2003 | Doubler et al. |
| 6,626,904 B1 * | 9/2003 | Jammet et al. ............. 606/266 |
| 6,641,586 B2 | 11/2003 | Varieur |
| 6,755,829 B1 | 6/2004 | Bono et al. |
| 6,770,094 B2 | 8/2004 | Fehling et al. |
| 6,843,791 B2 | 1/2005 | Serhan |
| 6,911,030 B1 | 6/2005 | Vanacker et al. |
| 6,964,666 B2 | 11/2005 | Jackson |
| 7,163,539 B2 | 1/2007 | Abdelgany |
| 7,186,255 B2 | 3/2007 | Baynham et al. |
| 7,207,992 B2 * | 4/2007 | Ritland .................. 606/86 A |
| 7,326,210 B2 | 2/2008 | Jahng et al. |
| 7,591,839 B2 | 9/2009 | Biedermann et al. |
| 7,686,833 B1 | 3/2010 | Muhanna et al. |
| 7,736,380 B2 | 6/2010 | Johnston et al. |
| 7,803,174 B2 | 9/2010 | Denis et al. |
| 7,806,913 B2 * | 10/2010 | Fanger et al. ............ 606/260 |
| 7,867,255 B2 | 1/2011 | Miller et al. |
| 7,931,675 B2 | 4/2011 | Panjabi et al. |
| 7,935,134 B2 * | 5/2011 | Reglos et al. ............ 606/257 |
| 7,935,137 B2 | 5/2011 | Gorhan et al. |
| 7,981,141 B2 | 7/2011 | Morrison et al. |
| 7,981,142 B2 | 7/2011 | Konieczynski et al. |
| 8,002,806 B2 | 8/2011 | Justis |
| 8,002,808 B2 | 8/2011 | Morrison et al. |
| 8,007,523 B2 | 8/2011 | Wagner et al. |
| 8,012,188 B2 | 9/2011 | Melkent et al. |
| 8,048,123 B2 | 11/2011 | Mitchell et al. |
| 8,062,338 B2 | 11/2011 | McBride et al. |
| 8,062,341 B2 | 11/2011 | Binder et al. |
| 8,062,367 B2 | 11/2011 | Kirschman |
| 8,092,498 B2 | 1/2012 | Samudrala et al. |
| 8,092,501 B2 | 1/2012 | Mitchell et al. |
| 8,172,885 B2 | 5/2012 | Songer et al. |
| 8,197,519 B2 | 6/2012 | Schlaepfer |
| 8,216,285 B2 | 7/2012 | Markworth |
| 8,221,476 B2 | 7/2012 | Paul |
| 8,236,033 B2 | 8/2012 | Paul |
| 8,236,034 B2 | 8/2012 | Binder et al. |
| 8,262,708 B2 | 9/2012 | Michelson |
| 8,277,493 B2 | 10/2012 | Farris et al. |
| 8,323,283 B2 | 12/2012 | Michelson |
| 8,348,982 B2 | 1/2013 | Baynham et al. |
| 8,361,125 B2 | 1/2013 | Taylor et al. |
| 8,361,126 B2 | 1/2013 | Perrow et al. |
| 8,372,152 B2 | 2/2013 | Kirschman |
| 8,382,809 B2 | 2/2013 | Kaufman et al. |
| 8,403,970 B1 | 3/2013 | Bedor |
| 8,403,971 B2 | 3/2013 | Barrus et al. |
| 8,409,259 B1 | 4/2013 | Bedor |
| 8,409,260 B2 | 4/2013 | Biedermann et al. |
| 8,425,514 B2 | 4/2013 | Anderson et al. |
| 8,425,576 B2 | 4/2013 | Anderson et al. |
| 8,435,266 B2 | 5/2013 | Richelsoph |
| 8,439,923 B2 | 5/2013 | Won et al. |
| 8,480,716 B2 | 7/2013 | Perrow et al. |
| 8,652,176 B2 | 2/2014 | Ramadan et al. |
| 8,652,178 B2 | 2/2014 | Abelgany |
| 8,672,978 B2 | 3/2014 | Dant et al. |
| 8,672,984 B2 | 3/2014 | Lindemann et al. |
| 8,764,804 B2 | 7/2014 | Rezach |
| 8,771,319 B2 | 7/2014 | Prajapati |
| 8,795,340 B2 | 8/2014 | Weiman |
| 8,840,649 B2 | 9/2014 | de Coninck |
| 2001/0012937 A1 | 8/2001 | Schaffler-Wachter et al. |
| 2001/0047173 A1 | 11/2001 | Schlapfer et al. |
| 2002/0032443 A1 | 3/2002 | Sherman et al. |
| 2002/0052603 A1 | 5/2002 | Nichols et al. |
| 2003/0023240 A1 | 1/2003 | Amrein et al. |
| 2003/0023243 A1 | 1/2003 | Biedermann et al. |
| 2003/0093078 A1 * | 5/2003 | Ritland .................. 606/73 |
| 2003/0216735 A1 | 11/2003 | Altarac |
| 2004/0049190 A1 | 3/2004 | Biedermann et al. |
| 2004/0097933 A1 | 5/2004 | Lourdel et al. |
| 2004/0127899 A1 | 7/2004 | Konieczynski et al. |
| 2004/0143264 A1 | 7/2004 | McAfee |
| 2004/0225289 A1 | 11/2004 | Biedermann et al. |
| 2004/0260284 A1 | 12/2004 | Parker |
| 2005/0080415 A1 | 4/2005 | Keyer et al. |
| 2005/0085812 A1 * | 4/2005 | Sherman et al. ............ 606/61 |
| 2005/0096653 A1 | 5/2005 | Doubler et al. |
| 2005/0143737 A1 | 6/2005 | Pafford et al. |
| 2005/0171537 A1 | 8/2005 | Mazel et al. |
| 2005/0171542 A1 | 8/2005 | Biedermann et al. |
| 2005/0203516 A1 | 9/2005 | Biedermann |
| 2005/0203517 A1 | 9/2005 | Jahng et al. |
| 2005/0215001 A1 | 9/2005 | Okada |
| 2005/0216003 A1 | 9/2005 | Biedermann et al. |
| 2005/0222570 A1 | 10/2005 | Jackson |
| 2005/0228379 A1 | 10/2005 | Jackson |
| 2005/0261687 A1 | 11/2005 | Garamszegi |
| 2005/0267472 A1 | 12/2005 | Biedermann et al. |
| 2005/0267485 A1 | 12/2005 | Cordes et al. |
| 2005/0277924 A1 | 12/2005 | Roychowdhury |
| 2005/0277927 A1 | 12/2005 | Guenther |
| 2006/0004357 A1 | 1/2006 | Lee |
| 2006/0009767 A1 | 1/2006 | Kiester |
| 2006/0036240 A1 * | 2/2006 | Colleran et al. ............ 606/61 |
| 2006/0036242 A1 | 2/2006 | Nilsson et al. |
| 2006/0036252 A1 | 2/2006 | Baynham |
| 2006/0058788 A1 | 3/2006 | Hammer |
| 2006/0058789 A1 | 3/2006 | Kim et al. |
| 2006/0074419 A1 | 4/2006 | Taylor et al. |
| 2006/0084979 A1 | 4/2006 | Jackson |

(56) References Cited

U.S. PATENT DOCUMENTS

| | | |
|---|---|---|
| 2006/0095038 A1 | 5/2006 | Jackson |
| 2006/0100621 A1 | 5/2006 | Jackson |
| 2006/0100622 A1 | 5/2006 | Jackson |
| 2006/0149233 A1 | 7/2006 | Richelsoph |
| 2006/0149240 A1 | 7/2006 | Jackson |
| 2006/0149241 A1 | 7/2006 | Richelsoph |
| 2006/0155279 A1 | 7/2006 | Ogilvie |
| 2006/0161152 A1 | 7/2006 | Ensign et al. |
| 2006/0173456 A1 | 8/2006 | Hawkes et al. |
| 2006/0200133 A1 | 9/2006 | Jackson |
| 2006/0200147 A1 | 9/2006 | Ensign et al. |
| 2006/0229606 A1 | 10/2006 | Clement et al. |
| 2006/0233597 A1 | 10/2006 | Ensign et al. |
| 2006/0235385 A1 | 10/2006 | Whipple |
| 2006/0235392 A1 | 10/2006 | Hammer |
| 2006/0235393 A1 | 10/2006 | Bono |
| 2006/0241594 A1 | 10/2006 | McCarthy et al. |
| 2006/0241599 A1 | 10/2006 | Konieczynski |
| 2006/0241603 A1 | 10/2006 | Jackson |
| 2006/0247635 A1 | 11/2006 | Gordon et al. |
| 2006/0264937 A1 | 11/2006 | White |
| 2006/0265074 A1* | 11/2006 | Krishna et al. ............ 623/17.15 |
| 2006/0271047 A1 | 11/2006 | Jackson |
| 2006/0276789 A1 | 12/2006 | Jackson |
| 2007/0010817 A1 | 1/2007 | de Coninck |
| 2007/0016204 A1 | 1/2007 | Martinez et al. |
| 2007/0055235 A1 | 3/2007 | Janowski |
| 2007/0055242 A1 | 3/2007 | Bailly |
| 2007/0093817 A1 | 4/2007 | Barrus et al. |
| 2007/0093820 A1 | 4/2007 | Freudiger |
| 2007/0093832 A1 | 4/2007 | Abdelgany |
| 2007/0118122 A1* | 5/2007 | Butler et al. .................... 606/61 |
| 2007/0118123 A1 | 5/2007 | Strausbaugh et al. |
| 2007/0123867 A1 | 5/2007 | Kirschman |
| 2007/0157543 A1 | 7/2007 | Metz-Stavenhagen |
| 2007/0161999 A1 | 7/2007 | Biedermann |
| 2007/0167948 A1 | 7/2007 | Abdou |
| 2007/0167949 A1 | 7/2007 | Altarac et al. |
| 2007/0173817 A1 | 7/2007 | Sournac et al. |
| 2007/0173818 A1 | 7/2007 | Hestad et al. |
| 2007/0173819 A1 | 7/2007 | Sandlin |
| 2007/0173833 A1 | 7/2007 | Butler |
| 2007/0225707 A1 | 9/2007 | Wisnewski et al. |
| 2007/0233080 A1 | 10/2007 | Na et al. |
| 2007/0233086 A1 | 10/2007 | Harms |
| 2007/0233087 A1 | 10/2007 | Schlapfer |
| 2007/0239159 A1* | 10/2007 | Altarac et al. ................. 606/61 |
| 2007/0270818 A1 | 11/2007 | Rezach |
| 2008/0015588 A1 | 1/2008 | Hawkes |
| 2008/0027436 A1 | 1/2008 | Cournoyer et al. |
| 2008/0077139 A1* | 3/2008 | Landry et al. .................... 606/61 |
| 2008/0119853 A1 | 5/2008 | Felt et al. |
| 2008/0172093 A1 | 7/2008 | Nilsson |
| 2008/0177321 A1 | 7/2008 | Drewry |
| 2008/0183212 A1 | 7/2008 | Veldman et al. |
| 2008/0183213 A1 | 7/2008 | Veldman et al. |
| 2008/0195153 A1 | 8/2008 | Thompson |
| 2008/0195159 A1 | 8/2008 | Kloss et al. |
| 2008/0208260 A1 | 8/2008 | Truckai et al. |
| 2008/0243189 A1 | 10/2008 | Purcell et al. |
| 2008/0262553 A1 | 10/2008 | Hawkins et al. |
| 2009/0093820 A1* | 4/2009 | Trieu et al. ................... 606/103 |
| 2009/0204155 A1 | 8/2009 | Aschmann |
| 2009/0204156 A1* | 8/2009 | McClintock et al. ......... 606/278 |
| 2009/0248088 A1 | 10/2009 | Biedermann |
| 2009/0254123 A1 | 10/2009 | Pafford et al. |
| 2009/0287260 A1 | 11/2009 | Zehnder |
| 2009/0326584 A1* | 12/2009 | Slivka et al. ................. 606/261 |
| 2010/0036423 A1* | 2/2010 | Hayes et al. .................. 606/260 |
| 2010/0057126 A1 | 3/2010 | Hestad |
| 2010/0063551 A1 | 3/2010 | Richelsoph |
| 2010/0087865 A1 | 4/2010 | Biedermann et al. |
| 2010/0114318 A1 | 5/2010 | Gittings et al. |
| 2010/0137913 A1* | 6/2010 | Khatchadourian et al. .. 606/258 |
| 2010/0185247 A1 | 7/2010 | Richelsoph |
| 2010/0217319 A1* | 8/2010 | Todd ............................. 606/246 |
| 2010/0331884 A1 | 12/2010 | Hestad |
| 2010/0331886 A1 | 12/2010 | Fanger et al. |
| 2011/0004251 A1 | 1/2011 | Sweeney et al. |
| 2011/0077691 A1 | 3/2011 | de Coninck |
| 2011/0196423 A1 | 8/2011 | Ziolo et al. |
| 2011/0230916 A1 | 9/2011 | Richelsoph |
| 2011/0245873 A1* | 10/2011 | Winslow et al. ............. 606/254 |
| 2011/0270314 A1 | 11/2011 | Mueller et al. |
| 2012/0130427 A1 | 5/2012 | Hoffman et al. |
| 2014/0228895 A1 | 8/2014 | Ziolo et al. |

FOREIGN PATENT DOCUMENTS

| | | |
|---|---|---|
| WO | 2005/074823 A1 | 8/2005 |
| WO | 2006060430 | 6/2006 |
| WO | 2006065607 | 6/2006 |
| WO | 2007082019 A2 | 7/2007 |
| WO | WO2007082019 A2 | 7/2007 |
| WO | 2008/078163 A2 | 7/2008 |

OTHER PUBLICATIONS

International Search Report of PCT App. No. PCT/US2009/056343 dated Nov. 25, 2009.

Japanese Notification of Reasons for Refusal for Japanese Patent Application No. 2011-526300 dated Sep. 9, 2013.

Japanese Notification of Reasons for Refusal, Final, for Japanese Patent Application No. 2011-526300 dated Aug. 4, 2014.

International Search Report and Written Opinion of The International Searching Authority, Issued Jan. 16, 2015 by The International Searching Authority, in reference to PCT Application No. PCT/US2014/059475.

Stryker, Techtonix Surgical Protocol, Stryker Spine, Literature No. TLTCTSTIA, Feb. 2006, Allendale, New Jersey.

European Search Report of European App. No. 12 16 7524 dated Jan. 31, 2013.

Patent Examination Report of Australian Patent App. No. 2008317087 dated Feb. 14, 2013.

* cited by examiner

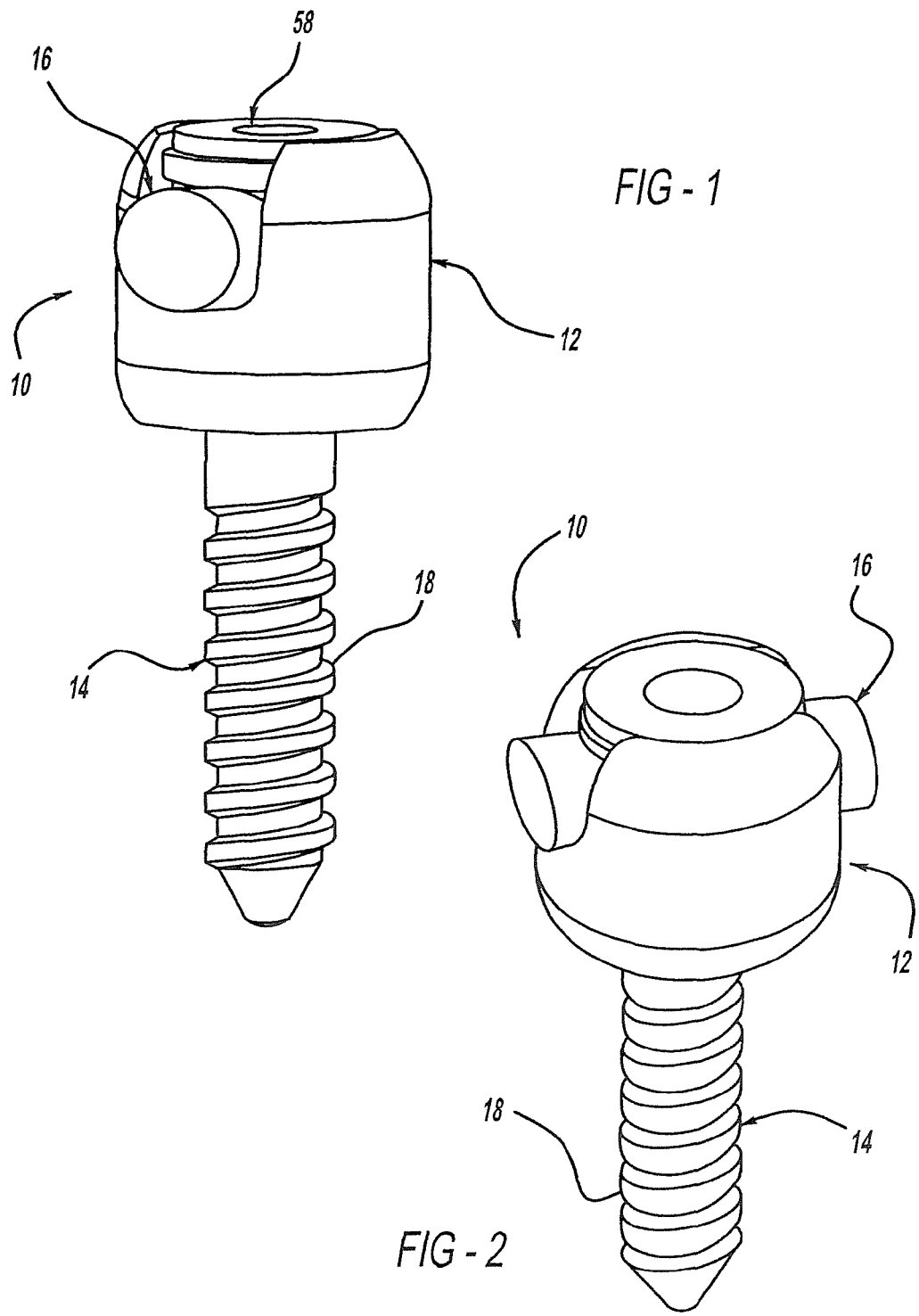

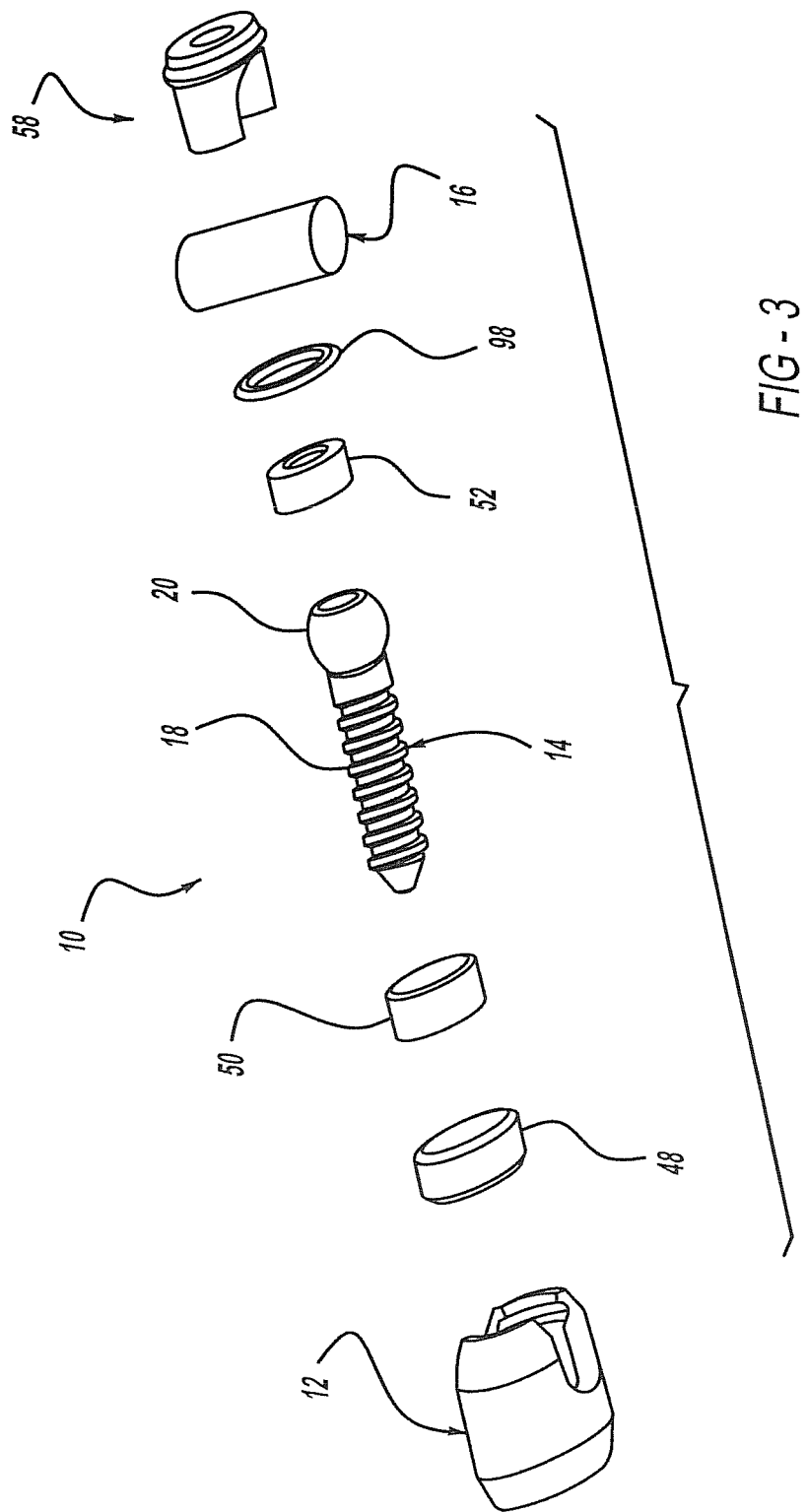

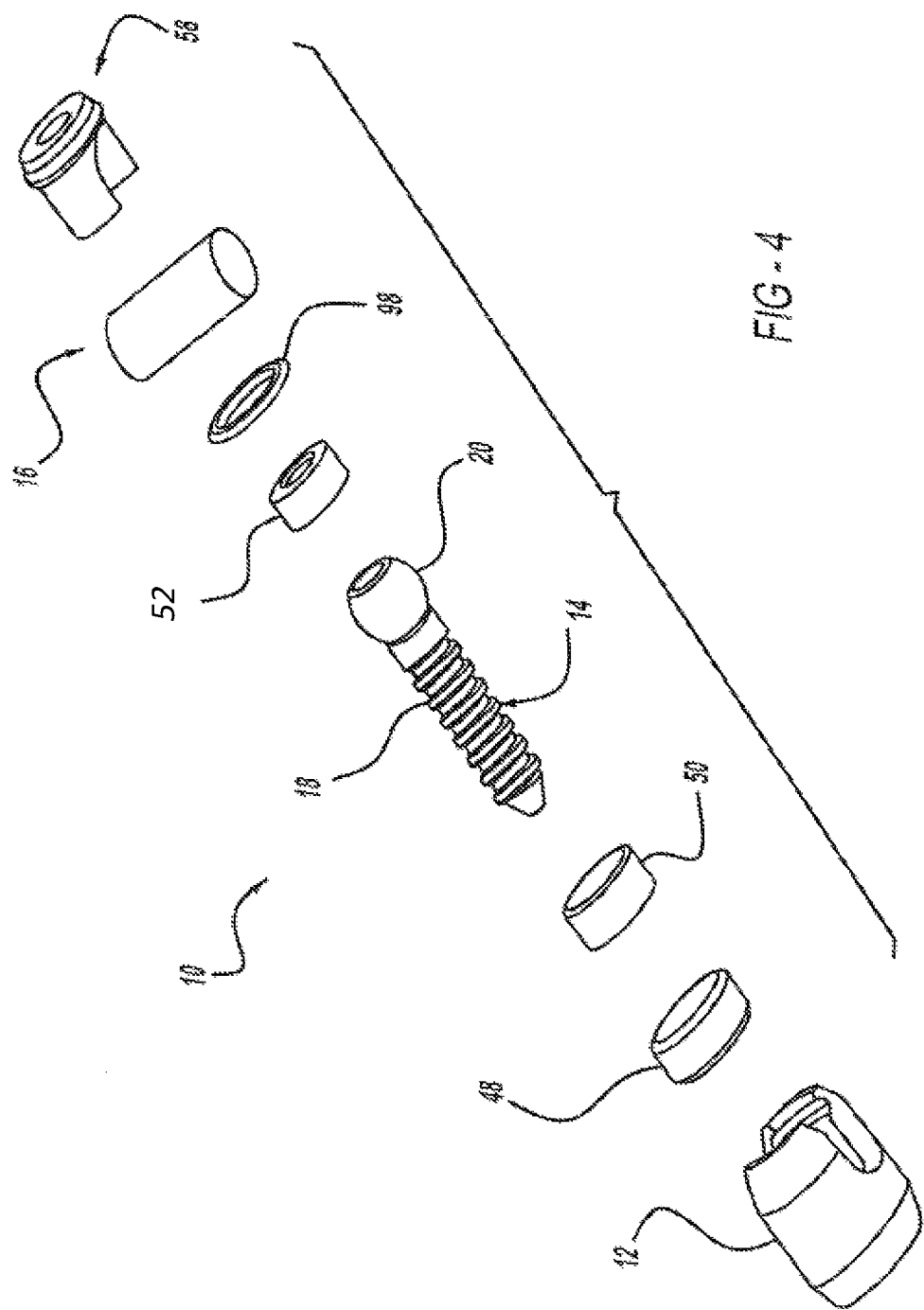

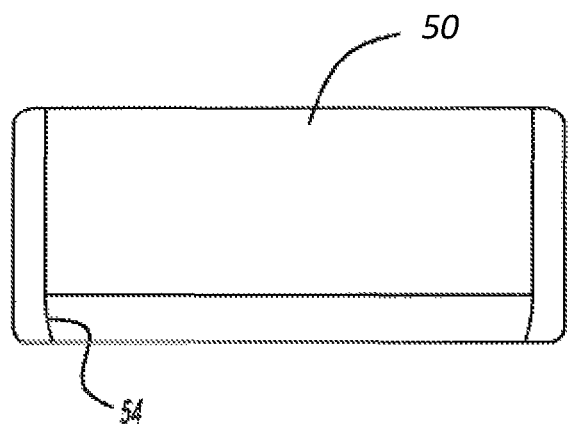
FIG-7
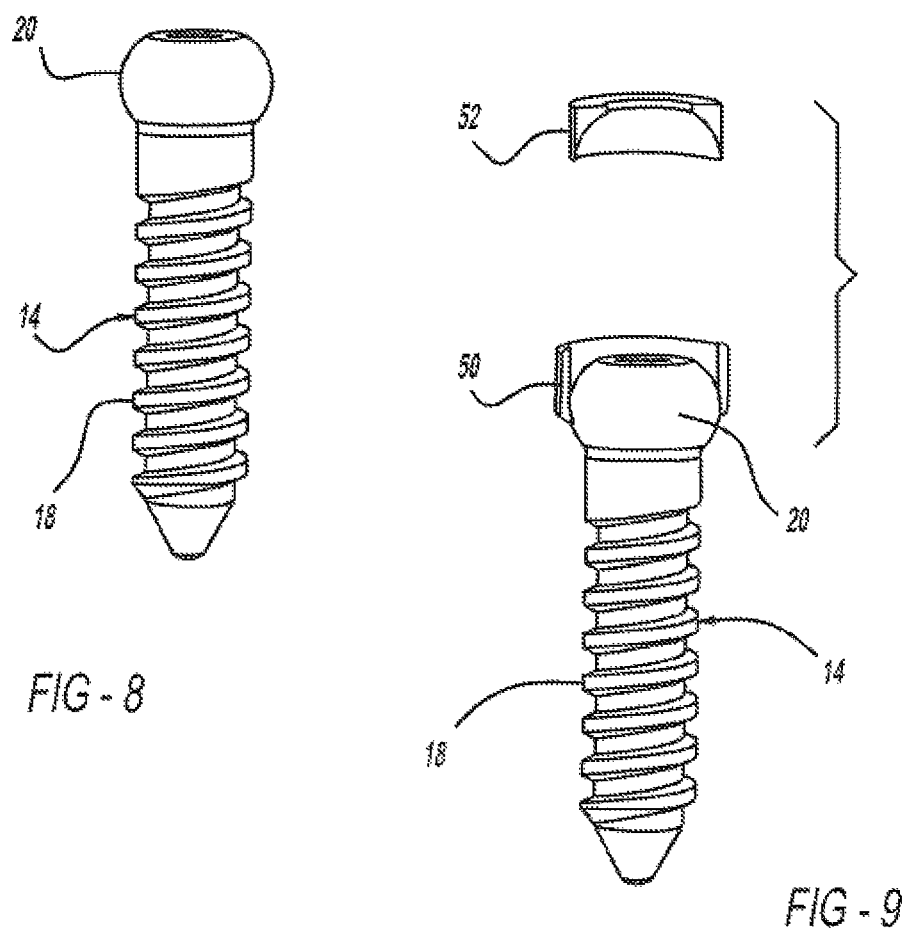
FIG-8
FIG-9

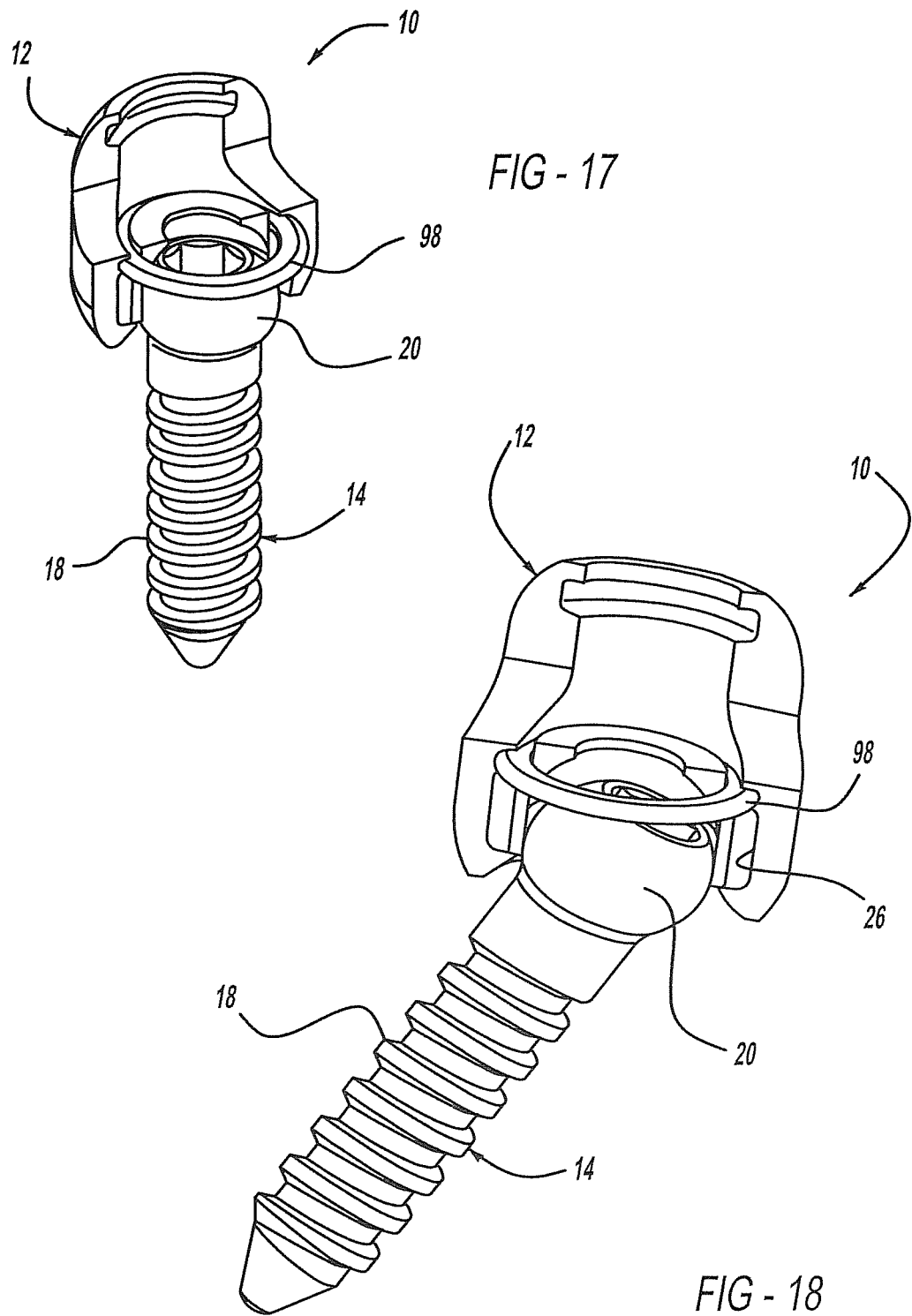

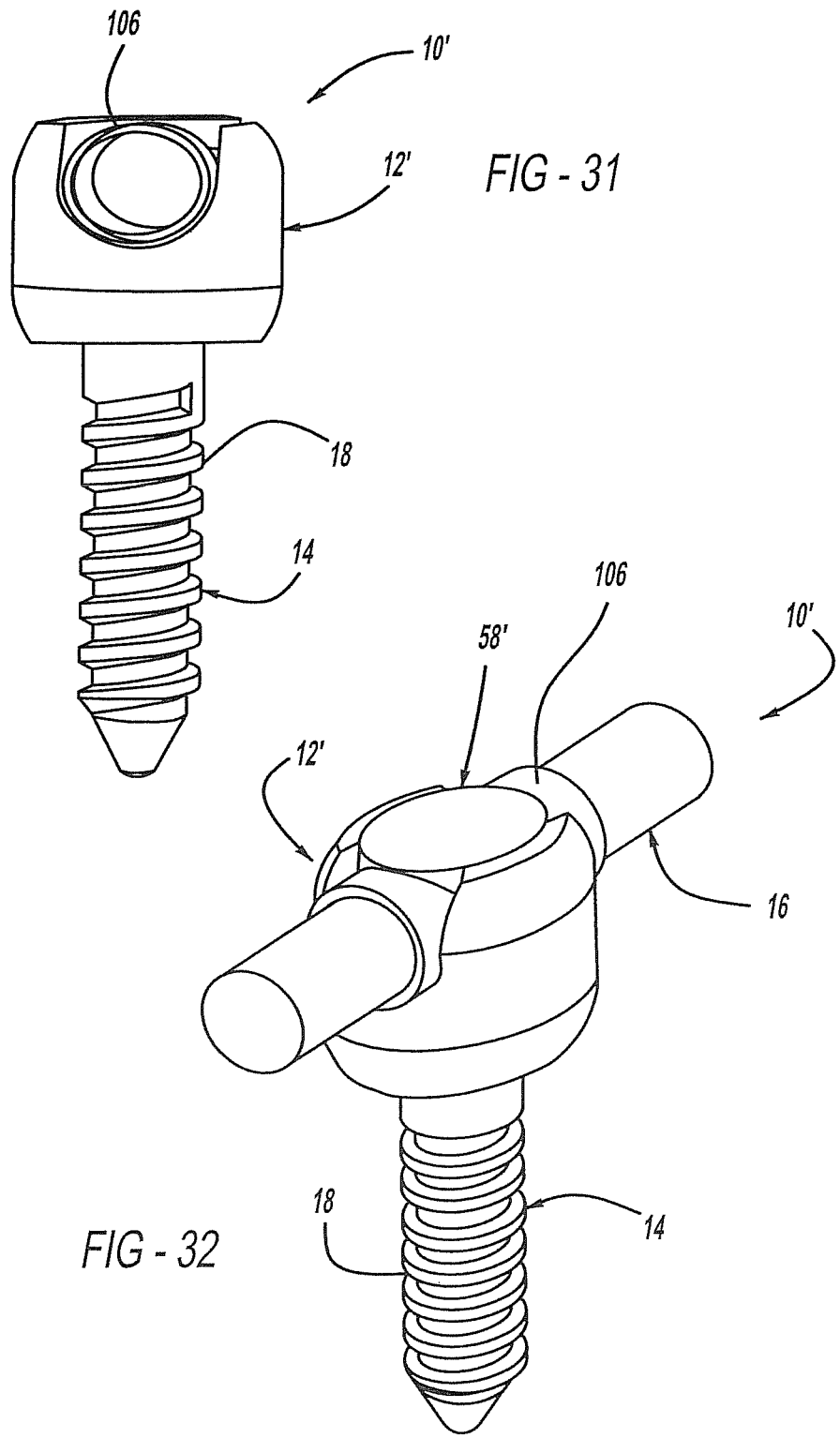

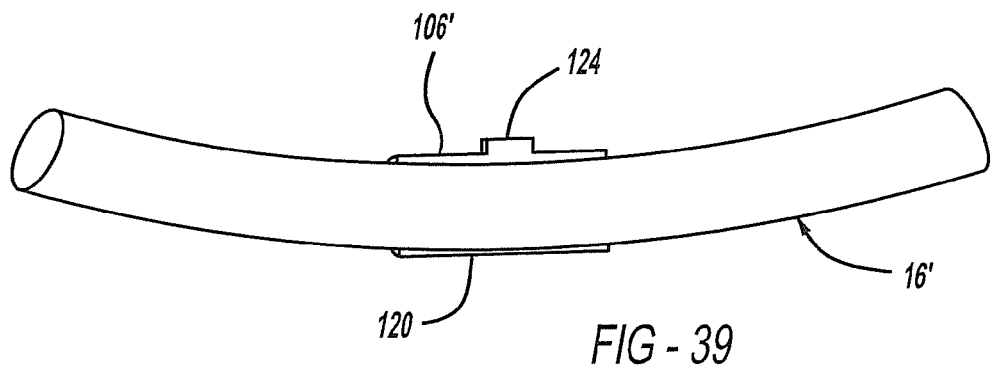
FIG - 39
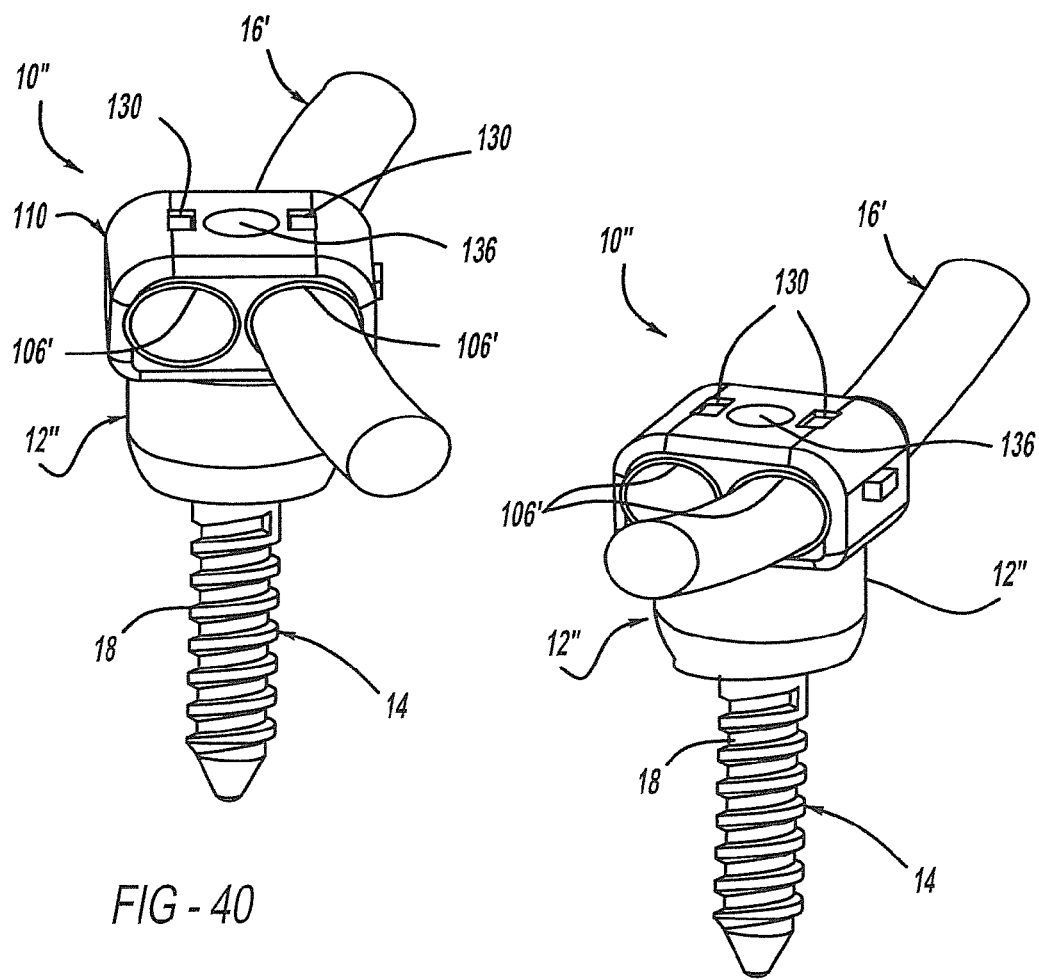
FIG - 40
FIG - 41

POLYAXIAL SCREW ASSEMBLY

CROSS-REFERENCE TO RELATED APPLICATIONS

This application claims the benefit of priority to U.S. Provisional Patent Application Ser. No. 61/095,485, filed Sep. 9, 2008, which is incorporated herein by reference.

BACKGROUND OF THE INVENTION

1. Technical Field

The present invention relates to orthopedic devices and, more specifically, to spinal stabilization systems which can particularly be used in the therapeutic correction of scoliosis. The present invention generally relates to polyaxial screw technology and, more specifically, load sharing and its application in polyaxial screw technology for the spine. In a preferred embodiment, the technology can be applied to the treatment and correction of scoliosis.

More specifically, polyaxial screw technology has been in existence for a number of years. While the technology has advanced, the focus of key advances have been on providing smaller and stronger means for fixing a screw that fixes a body member and rod assembly to vertebrae, with each screw assembly having the basic structure of a body with pivot means around the screw head and a rod slot. If the rod to be disposed in the rod slot is not centered relative to the screw head, the body can pivot over to adjust for the misalignment. Examples of such systems are abundant in the art.

2. Background Art

Once the polyaxial screw is connected to the rod, the assembly is locked such that the screw angulation is fixed relative to the body portion. For example, U.S. Pat. No. 6,740,086 to Richelsoph, issued May 25, 2004, shows one such system.

In a more uncommon approach, U.S. Pat. No. 4,805,602 to Puno, et al., issued Feb. 21, 1989 discloses micromotion between a round screw head and a seat of a body member such that the screw is allowed to rotate in the seat. More specifically, the assembly includes a rod and plurality of vertebral anchors that are positioned on the spine on either side of the spinous process spanning the portion of the spine to be immobilized. The rod is secured to the vertebral laminae by the vertebral anchors. The anchor includes a transpedicular screw member which is secured to a vertebrae. A rod support or body member includes a cup which captures the screw and optionally permits micromotion between the rod support and the screw. This type of approach leads to other issues, as the surgical correction to the spine cannot be effectively controlled and issues of the head rotating in the socket producing failure of the system. Therefore, this type of approach is not common. Of course, the locking strength of the spherical head of the screw in the body portion varies from design to design, as well as a locking mechanism.

A more specific issue related to polyaxial screw technology is the application of load sharing, which has various advantages, including reduction of adjacent segment degeneration and improved fusion quality. The term "load sharing" in spine relates to the ability of a spinal stabilization device to share loads otherwise placed solely upon the spine. Conventional methods of spinal fixation utilize a relatively rigid spinal fixation device to support an injured spinal segment or segments being surgically corrected. Such fixation limits movement of the injured segment. These conventional spinal fixation devices connect and couple rods or plates to fixing screws such that the injured spinal segment is supported and held in a relatively rigid and fixed position by the rods or plates. The connection units, such as the rods and plates, are used during fusion, whereby bone graft s inserted into the space and the implants act as internal braces to stabilize the spine during the bone healing and fusion process. The connection units also reduce pain and further injury to the patient by substantially restraining the movement of the spinal column. However, because the connection interferes with normal movement of the spinal column, negative effects, such ad degradation of other healthy segments or pseudoarthrosis can occur causing further complications and issues associated with the spinal column. More specifically, and in the case of large diameter rods, high rigidity of the rods and/or plates used in conventional fixation devices, the patient's fixed joints are not allowed to move after the surgical operation. Consequently, such spinal fixation devices cause decreased mobility of the patient and increased stress on the remainder of the spinal column joints adjacent to the operated area. Such excessively rigid spinal fixation can result in what is termed "stress shielding", whereby the bone graft used for fusion does not receive sufficient loading to allow for solid fusion. By altering this approach and allowing load sharing in the spine, we now have a reduction of adjacent segment degeneration and improved fusion quality.

An early approach for load sharing was a basic system change from a larger diameter rod to a smaller diameter rod. Newer techniques use more flexible rods or complex mechanisms placed as connectors between rod segments.

For example, U.S. Pat. No. 6,241,730 to Alby, issued Jun. 5, 2001, oses a complex link with moveable parts. More specifically, the Alby patent loses an intervertebral link device including at least one damper element constituted by a cage and a pin designed to be connected to bone anchor elements. The pin is engaged in a housing of the cage and is fitted with two elastically deformable members operating in opposition to an applied traction force or compression force. The damper element is a pin that is mounted inside the cage by a joint allowing multi-directional relative pivoting between the pin and the cage, at least about the axis contained in a plane perpendicular to the pin and angular abutment between the cage and the pin enables the multi-directional relative pivoting to be limited in amplitude to a predetermined value of about 4°.

U.S. Pat. No. 7,326,210 to Jahng, et al., issued Feb. 5, 2008, loses a flexible rod constructed from two different materials. More specifically, the flexible connection unit disclosed for use in a spinal fixation device includes a longitudinal member having first and second ends and at least one spacer located between the first neck and second ends wherein the spacer includes a first portion made from a first material and a second portion made from a second material and at least one flexible member located in a longitudinal axial channel of the spacer wherein the first and second ends substantially limit motion of the spacer in the longitudinal axial direction with respect to the flexible member.

Both of the above techniques have drawbacks due to the complexity, size, strength, or inability to integrate into effective spinal stabilization systems. Their use is substantially directed to fusion techniques. Stabilization of the spine for non-fusion is a totally different matter raising totally different issues. Flexion of the spine creates very high loads on the screw-bone interface and often causes loosening of the screws from the vertebrae. Common complications are for the screw to be pulled loose or screw failure, thereby totally destabilizing the fixation device.

The present invention provides a much simpler device from an engineering point of view yet effective in both fixation during fusion and non-fusion techniques. This allows for many options in the treatment of the spine with the same basic system. In addition, the present invention can be utilized for stabilization and reduction during the treatment of scoliosis.

Scoliosis is the medical term for curvature of the spine. Scoliosis occurs in approximately 2% of women and less than ½% of men. It usually starts in the early adolescence and may gradually progress as rapid growth occurs. However, scoliosis can occur at any age from juvenile to adult. Persons with a curve of 10° or less are often thought to have just an asymmetry of the spine, but in children who end up with significant curves, a 10° curve can progress to a 50° curve and a significant deformity if there is enough growing time remaining. Persons with curves measuring under 30° entering adulthood are considered having a mild curve while those over 60° are considered severe. Treatment is recommended, depending on the severity and the age of the person. It would be advantageous to be able to correct the severity before it progresses while the spine is still growing, and various techniques along with various devices, such as the one covered by U.S. Pat. No. 6,554,831 by Rivard et al. have been develop, but these devices and techniques are not well developed and have complications. Adapting a rigid prior art system to the treatment of early onset scoliosis would result in degenerative growth of the spine due to the fixed nature of prior art systems or repetitive surgeries.

There are generally three options to the treatment of scoliosis. The first option is doing nothing. This may be a reasonable decision depending on the age of the patient and the predicted outcome. If the person is a teen or pre-teen and the prediction is that this curve will worsen, then doing nothing may not be appropriate. As the curve progresses, torso deformities occur. In the more severe curves, internal organs are compressed. Without surgery, such patients risk organ damage or failure. On the other hand, if the person has reached maturity, then if the curve is mild, below 40°, it may not increase any more. A second option is to wear a brace. Bracing has been shown to be a somewhat effective method of controlling the curve progression, but it does not cure scoliosis. From a practical aspect though, this treatment is reserved for children and adolescents in whom the prediction of a rapid increase in the curve needs to be thwarted. However, a brace worn even 23 hours per day and worn properly does not guarantee that the curve will not continue to increase.

The third option of treatment is surgery. For those persons who already have a significant curve with a significant deformity, surgery can reduce the curve and significantly reduce the deformity.

The usual scoliosis curve is a thoracic curve. In these curves, the general procedure is a posterior spinal fusion. The fusion is a procedure wherein the individual vertebra are fused to the one above and below. Typically, ten or more segments are included.

It should also be noted that scoliosis a three-dimensional problem, with the curvature of the spine occurring not only in the coronal plane, but usually in angles relative to the coronal plane. One of the aims of surgery is to try to restore the normal contour of the back from both the front view and the side view to restore normal fuction, balance, and cosmetics.

The spine has normal curves when looking from the side but it should appear straight when looking from the front. Kyphosis is generally a curvature of the upper spine, which when seen from the side the spine is bent forward. Lordosis is a curve that has its convexity anteriorly and concavity posteriorly. People with scoliosis develop additional curves to either side and the vertebrae of the spine twist on each other like a corkscrew.

The present invention addresses various issues encountered in the prior art. Generally, angulation of a polyaxial screw is a means of compensating for a rod that is offset relative to a screw that is inserted into the pedicile, as used above. However, angulation is not the key issue. Rather, the offset is the key issue. With regard to the issue of the rigidity of prior art systems, the present invention allows for locking of a polyaxial screw rigidly at a desired angulation but the present invention also provides load sharing. Hence, the two aspects of the design are not mutually exclusive as in the prior art. Accordingly, combining angulation of the polyaxial screw with additional offset capability allows an increase in the amount of angulation over the prior art. Likewise, combining load sharing of external components into an internal mechanism within the polyaxial screw while still utilizing standard rods eliminates complex external mechanisms or materials subject to failure. Thus, the present invention provides a polyaxial screw that can moderate loads relative to the direction of the load exerted by the force on the rod from adjacent levels.

SUMMARY OF THE INVENTION

In accordance with the present invention, there is provided a polyaxial screw assembly including internal load dampening means for sharing and dampening loads between at least one screw member and at least one rod member interconnected by the assembly.

The present invention further provides a method of interconnecting an orthopedic screw with a rod by load dampening with a body member interconnecting the screw to the rod.

DESCRIPTION OF THE DRAWINGS

Other advantages of the present invention are readily appreciated as the same becomes better understood by reference to the following detailed description when considered in connection with the accompanying drawings wherein:

FIG. 1 is a elevational view of a polyaxial screw assembly made in accordance with the present invention;

FIG. 2 is a perspective view of the polyaxial screw assembly;

FIG. 3 is an exploded view of the polyaxial screw assembly;

FIG. 4 is a line drawing of an exploded view of the polyaxial screw assembly;

FIG. 7 is a cross-sectional view of a locking ring member;

FIG. 8 is an elevational view of a screw member made in accordance with the present invention;

FIG. 9 is an elevational view partially exploded of the screw member and locking assembly of the present invention;

FIG. 17 is a perspective view, partially broken away, of the present invention wherein the screw member is aligned with the longitudinal axis of the body member;

FIG. 18 is an elevational view, partially broken away and in perspective of the present invention wherein the screw member is angled relative to the longitudinal axis of the body member;

FIG. 31 is an elevational view of the embodiment shown in FIG. 30;

FIG. 32 is a perspective view of the embodiment shown in FIGS. 30 and 31 including a rod retained therein;

FIG. 39 is a fragmentary, perspective and partially cross-sectional view of the rod bearing of FIG. 34 retaining a portion of a rod member therein;

FIG. 40 is an elevational perspective view of the present invention retaining a curved rod therein;

FIG. 41 is a perspective view of the present invention including a rod retained therein rotated 90° from the position shown in FIG. 40;

FIG. 47b is a line drawing of the assembly shown in FIG. 47a;

FIG. 48b is a line drawing of the assembly shown in FIG. 48a;

FIG. 49b is a line drawing of the assembly shown in FIG. 49a;

FIG. 52a is a top perspective view exploded of the present invention;

FIG. 52b is a line drawing of the assembly shown in FIG. 52a;

FIG. 54b is a line drawing of the assembly shown in FIG. 54a;

DETAILED DESCRIPTION OF THE INVENTION

A polyaxial screw assembly made in accordance with the present invention is generally shown at 10 in the Figures. Primed numbers indicate like structure amongst the several embodiments. Each of the assemblies 10 shown can include an internal load dampening mechanism for sharing and dampening loads between at least one screw member and at least one rod member interconnected by the assembly 10. The term "load dampening mechanism" means that the assembly within a body member thereof described below, includes an absorptive mechanism for dampening loads transmitted between the articulating vertebrae, through the screw member, into the body member, along a rod, and passing to another body member. As explained below in greater detail, this allows for articulation of vertebrae interconnected by the present invention while loads transmitted through the system are dampened. This internal load dampening is accomplished through a compact efficient assembly and is effective to prevent deleterious stresses placed on the system, and especially the screw members. It also allows, in a fusion, for dampening of otherwise unnatural stresses imposed on the non-fused segments by the rigidity of the fused sections. This internal dampening ability, in combination with the ability of the present invention to articulate in a novel manner and, the body members to allow sliding along interconnected rod members results in a sophisticated system for allowing growth of the system concomitant with vertebrae growth. The present invention is well suited for the treatment of spinal deformities, such as scoliosis. The ability of the system to grow with the growth of the vertebrae makes the present invention particularly well suited for the treatment of prepubescent patients whose spines will grow yet require early onset therapeutic manipulation by the system.

Figure 46:
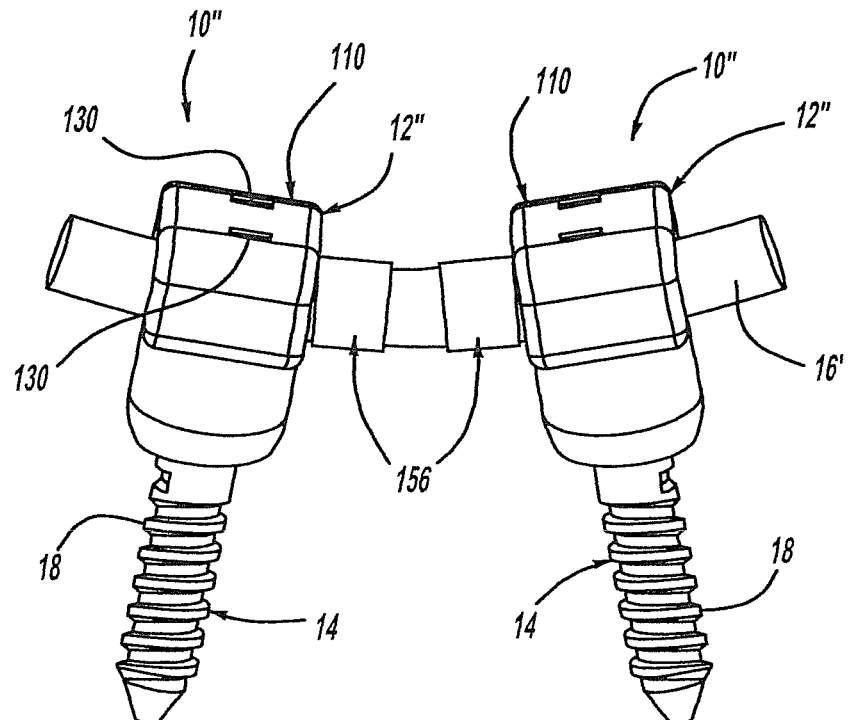
FIG. 46 is a side elevational view of the present invention showing a rod retained between two body members.
Figure 47A:
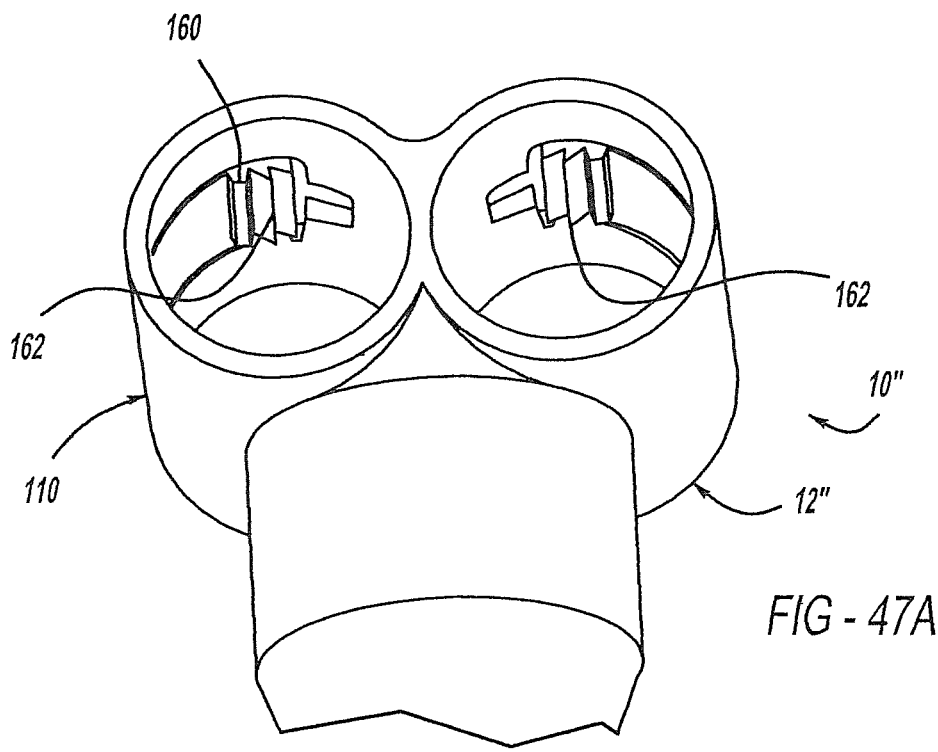
FIG. 47a is a perspective view of a dual rod retaining body member
Figure 47B:
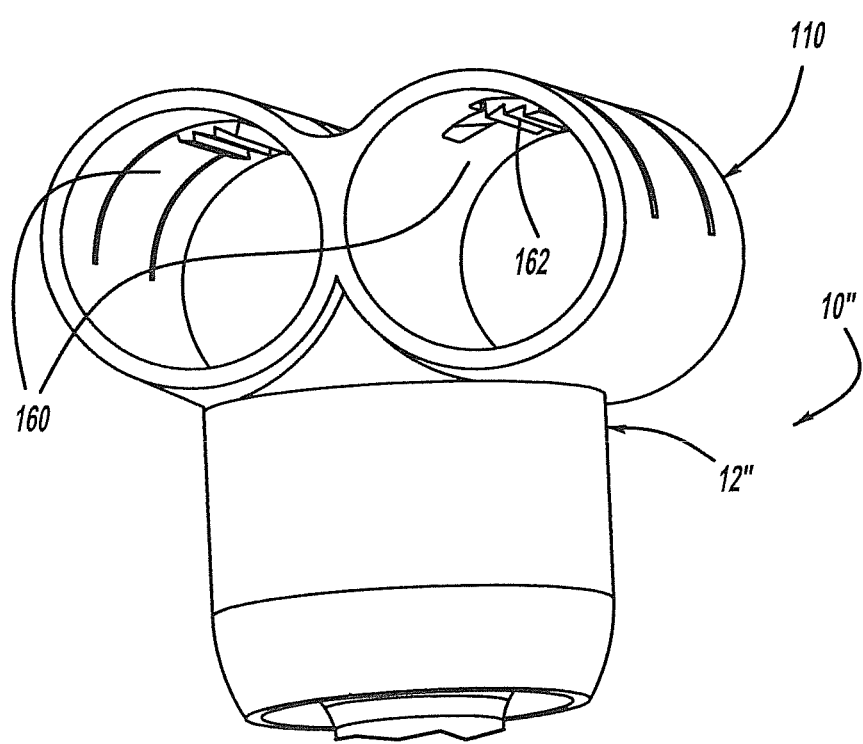
Figure 48A:
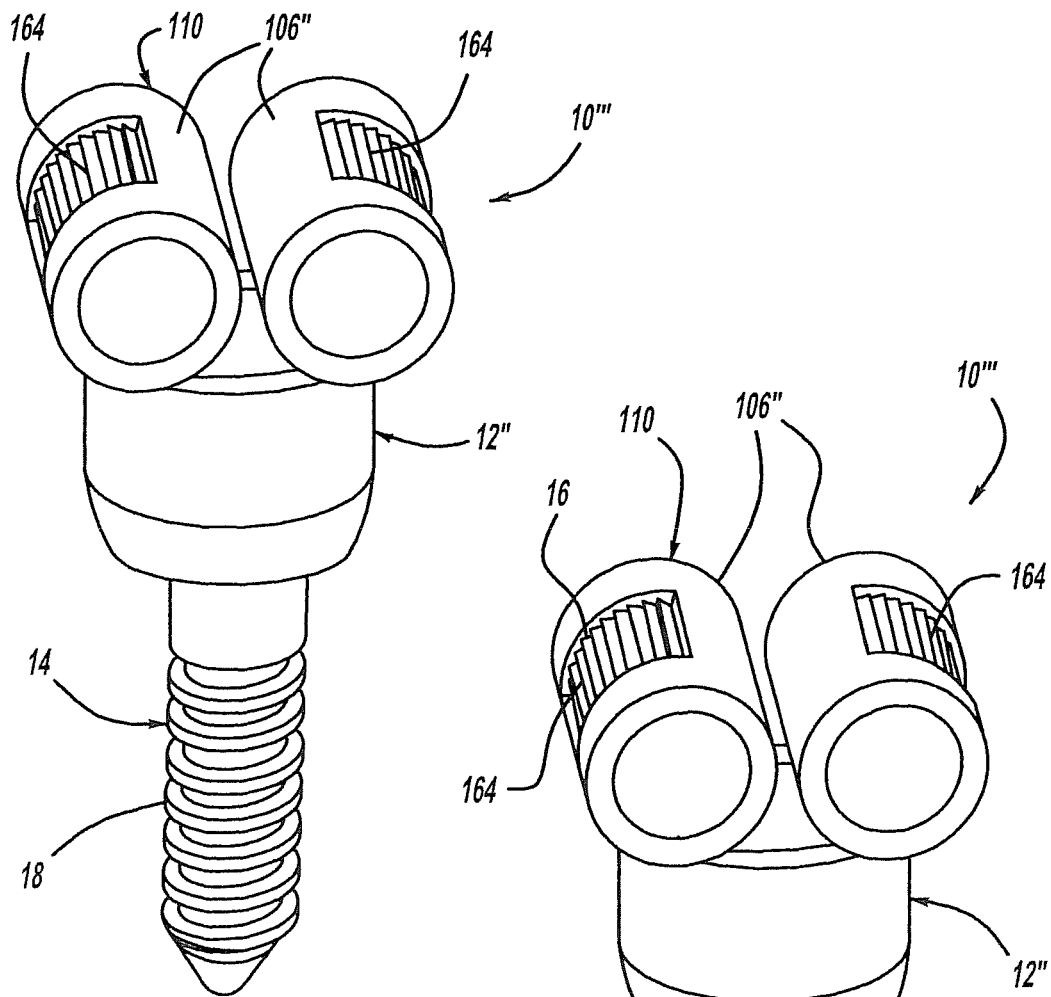
FIG. 48a is a top perspective view of a dual rod retaining assembly made in accordance with the present invention.
Figure 48B:
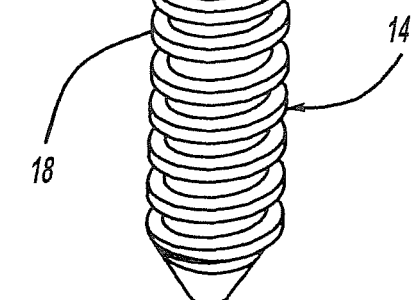
Figure 49A:
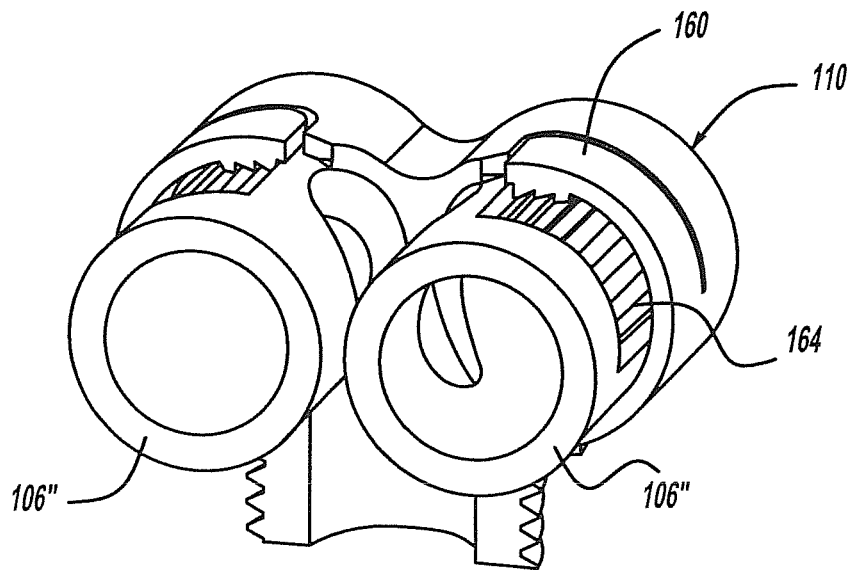
FIG. 49a is a top perspective view of a dual rod retaining assembly made in accordance with the present invention.
Figure 49B:
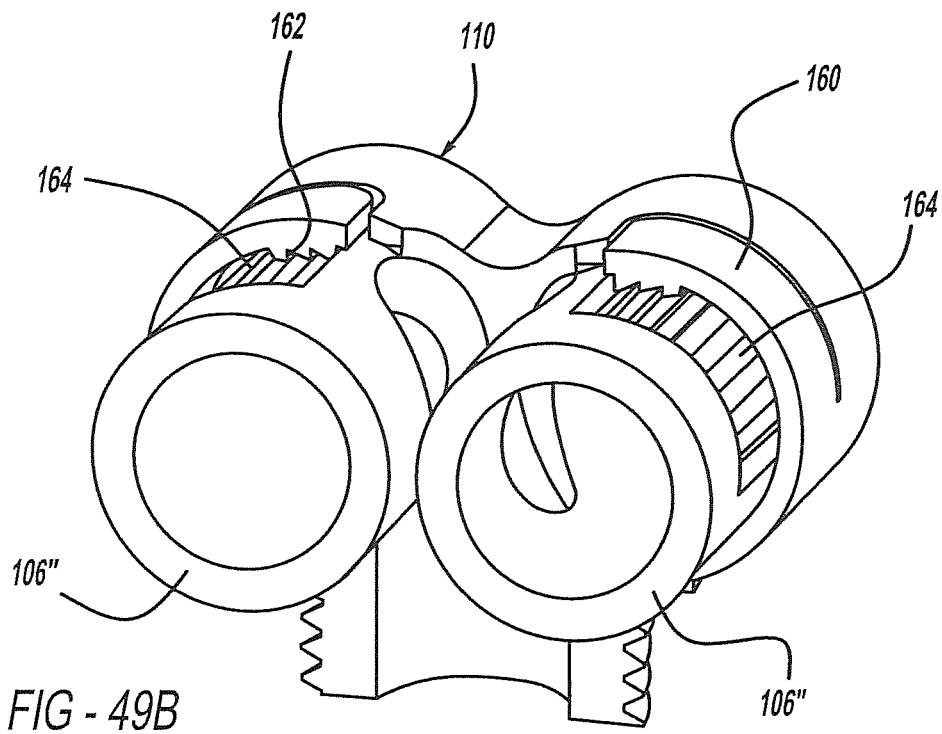
Figure 55A:
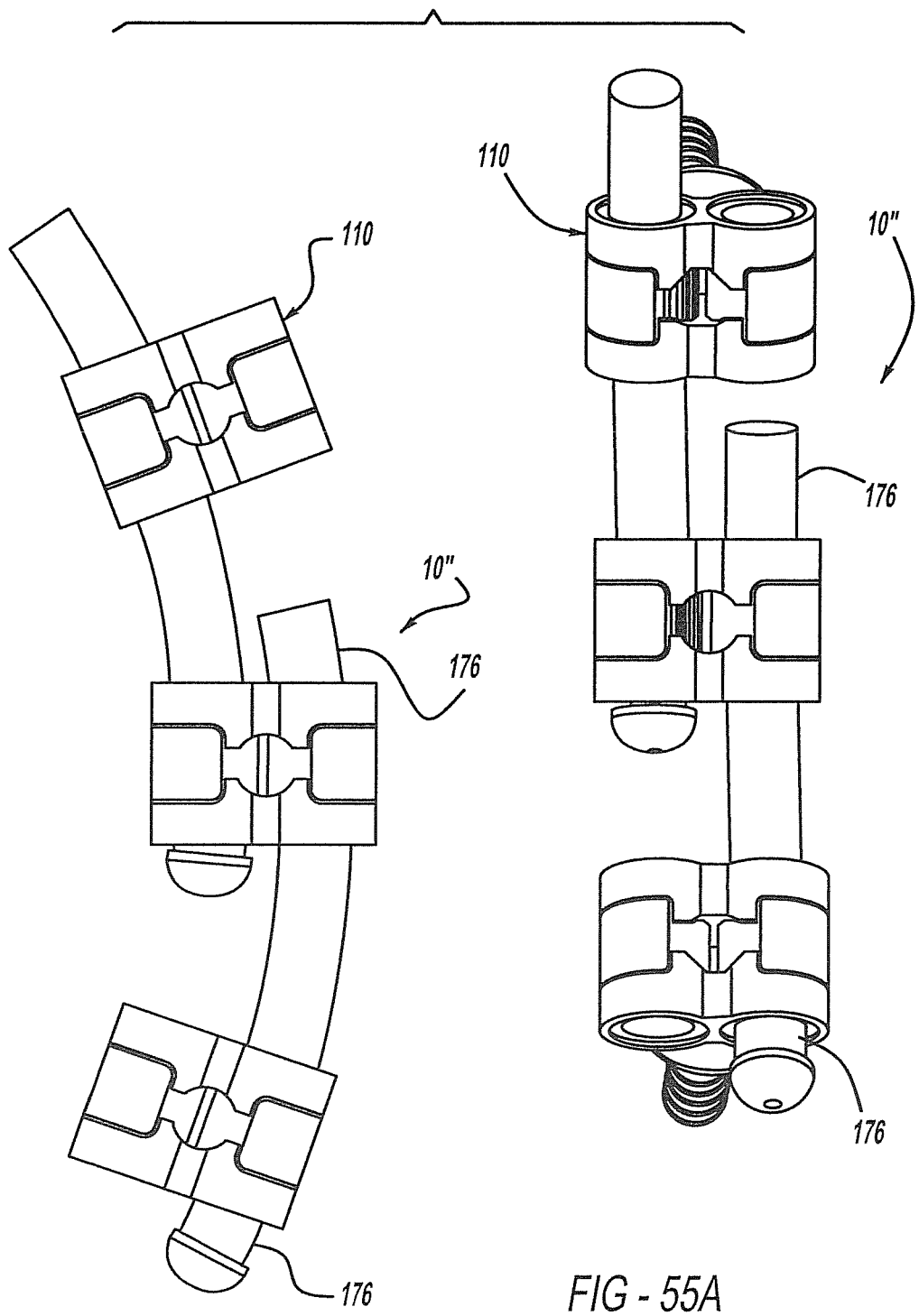
FIGS. 55a and b are plan views of a multi-segment system of the present invention in an initial position (left) and with the rods rotated 90° (right)
Figure 55B:
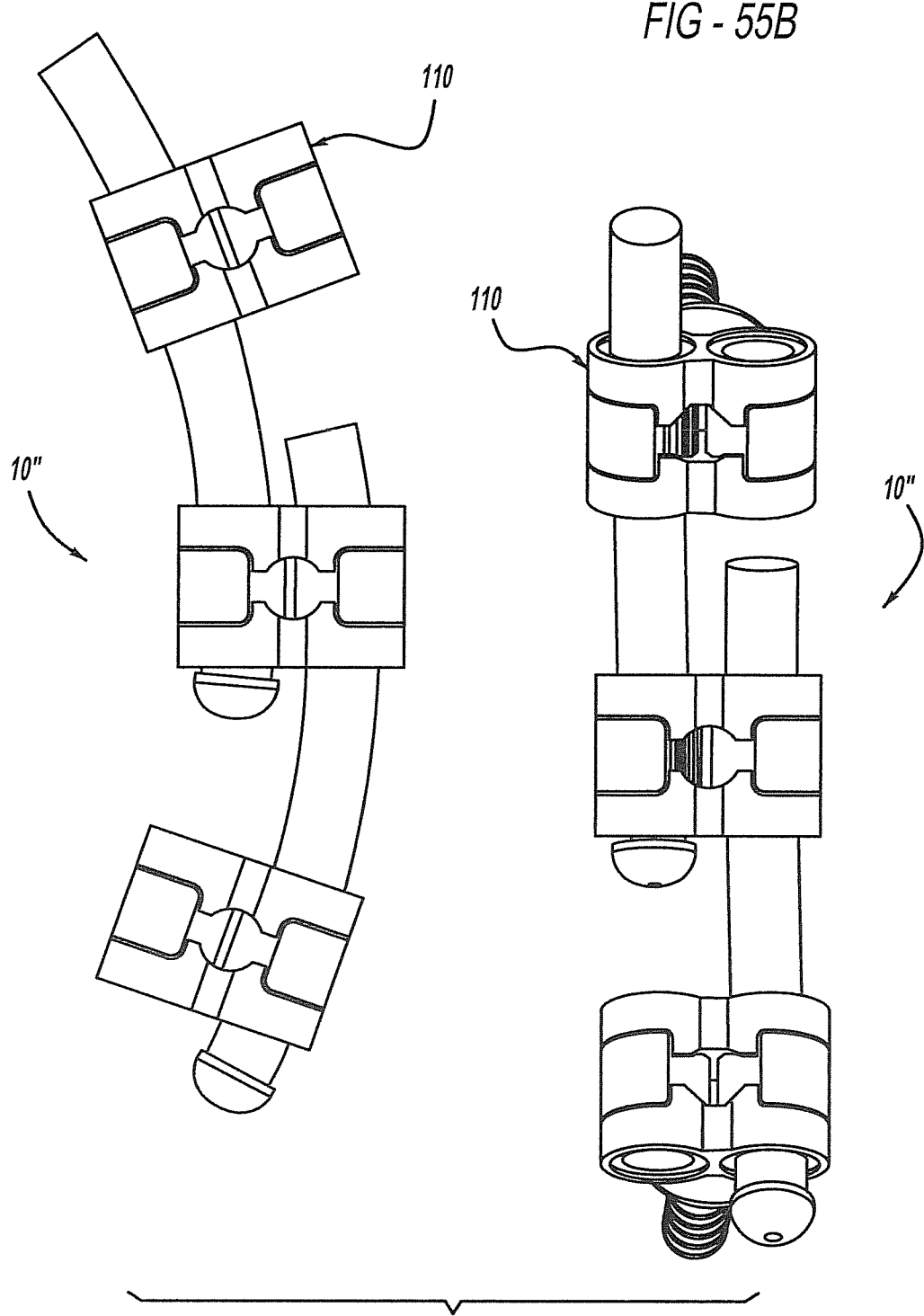

Referring more specifically to the drawings, and in particular at FIGS. 1-4, the polyaxial screw assembly 10 includes a body member generally shown at 12 for interconnecting a screw member generally shown at 14 to a rod member generally shown at 16. The body portion 12 interconnects the screw member 14 which is fixedly secured to a vertebra and to a rod member 16. The rod member 16 is used to interconnect the body member 12 with another body member 12 which would itself be fixedly secured to another vertebra via another screw 14. Examples of such interconnections are shown in FIGS. 46 and 55a and 55b. Such assemblies can be constructed with other devices known in the art, such as plates, fusions, etc.

Generally referring to the components of the assembly 10, the screw member 14 includes a threaded body portion 18 and a head portion 20. As best shown in FIGS. 3 and 4, the head portion 20 can be frusto-spherical, having a flat end portion generally including a hexagonal recess for insertion purposes by an appropriate hex tool.

Figure 6:
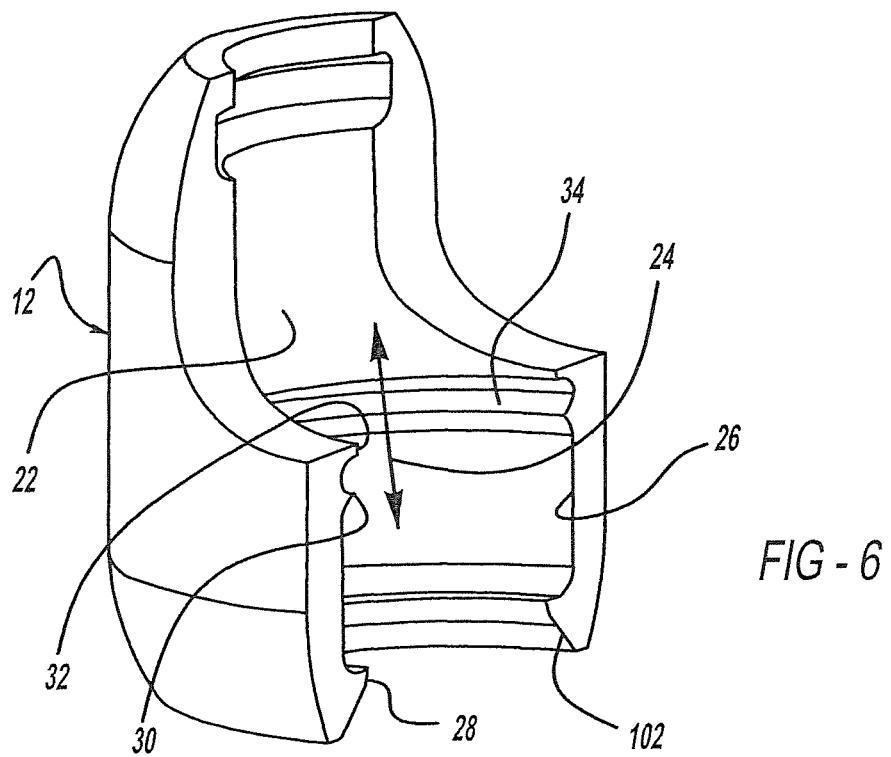
FIG. 6 is a cross-sectional view in perspective of the body member.
Figure 10:
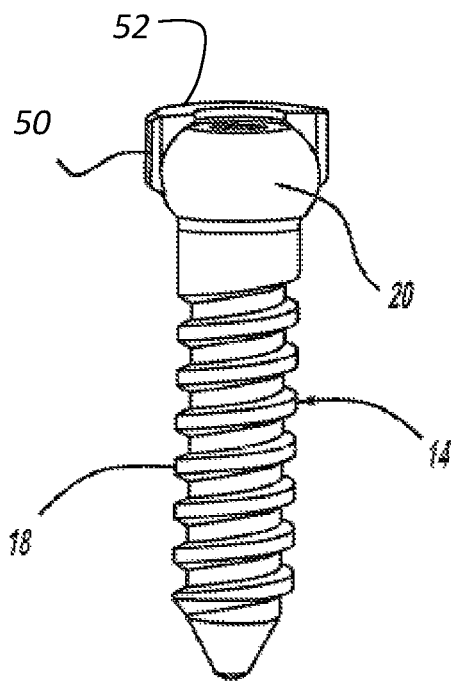
FIG. 10 is an elevational view, partially in cross-section, of the screw member and locking assembly in the locked position.
Figure 11:
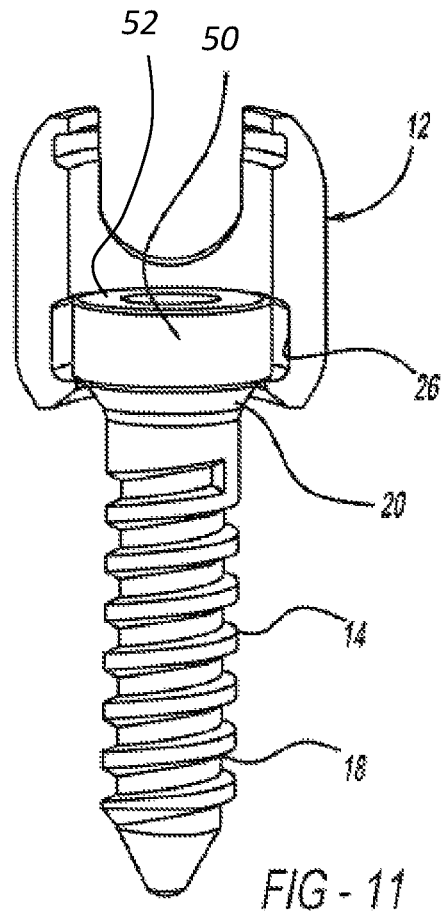
FIG. 11 is an elevational view, partially in cross-section, of the screw member and locking assembly in the locked position inside the body member.
Figure 12:
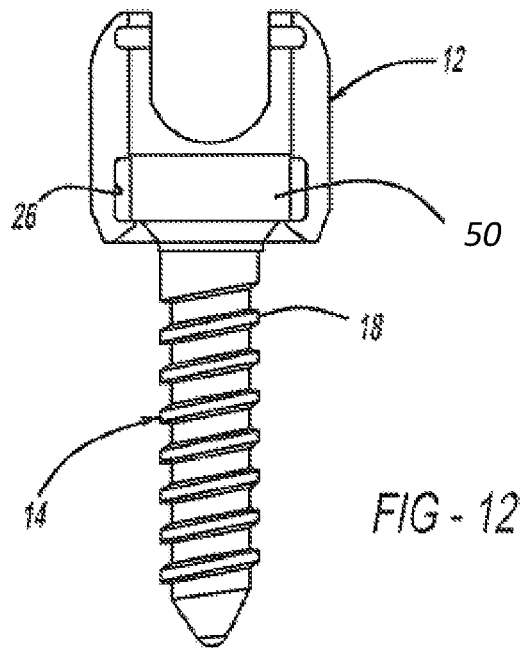
FIG. 12 is an elevational view of the screw member within the locking assembly in a locked position inside the body member.
Figure 13:
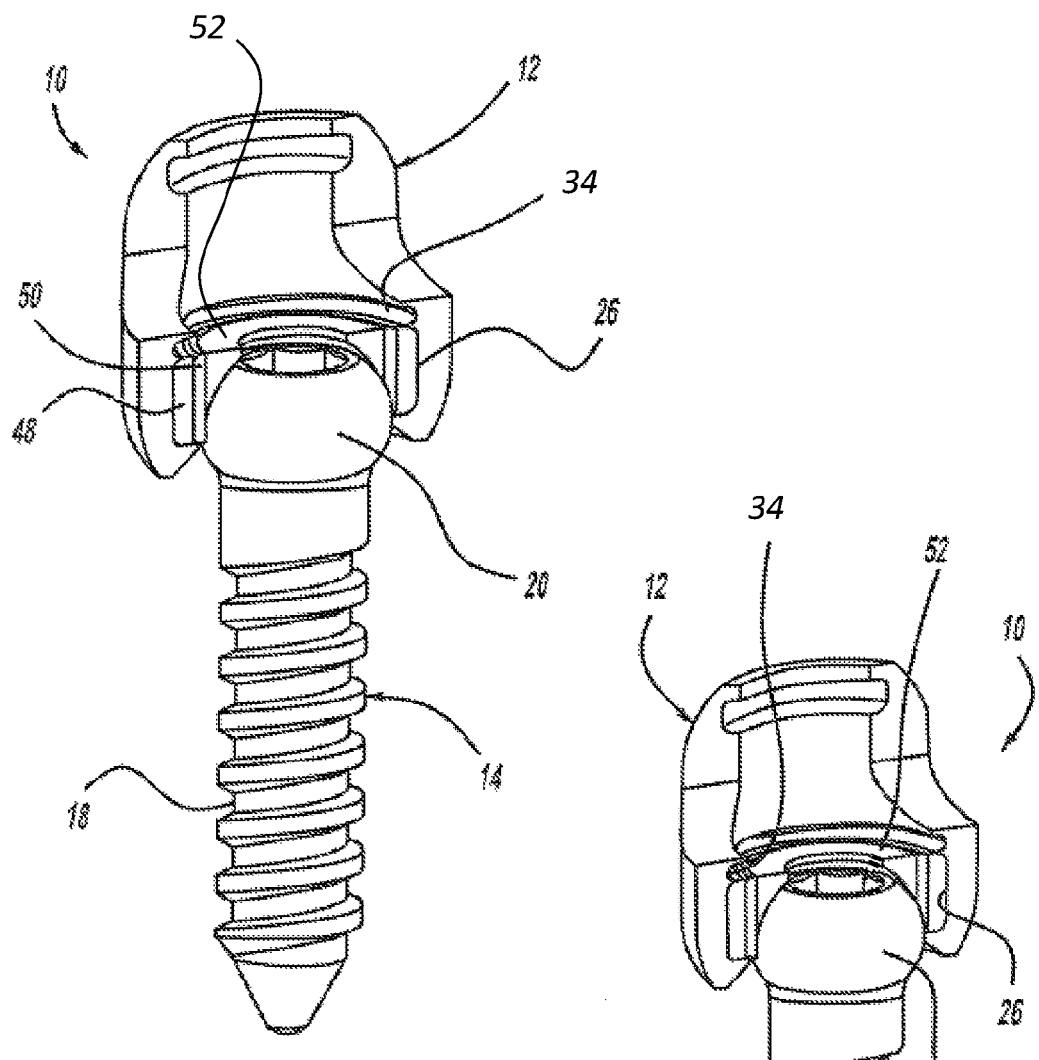
FIG. 13 is an elevational view in perspective, partially broken away of the screw member and locking assembly in the locked position inside the body member also including the load sharing damper of the present invention.
Figure 14:
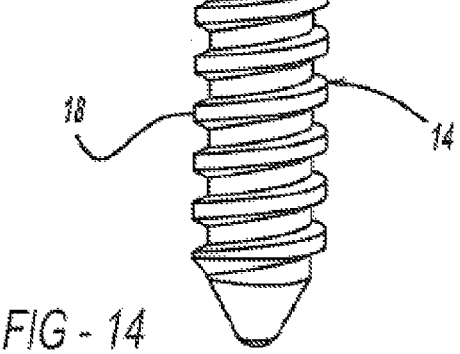
FIG. 14 is an elevational view in perspective, partially broken away of the locking assembly in the locked position inside the body member including the load sharing damper.
Figures 15, 16:
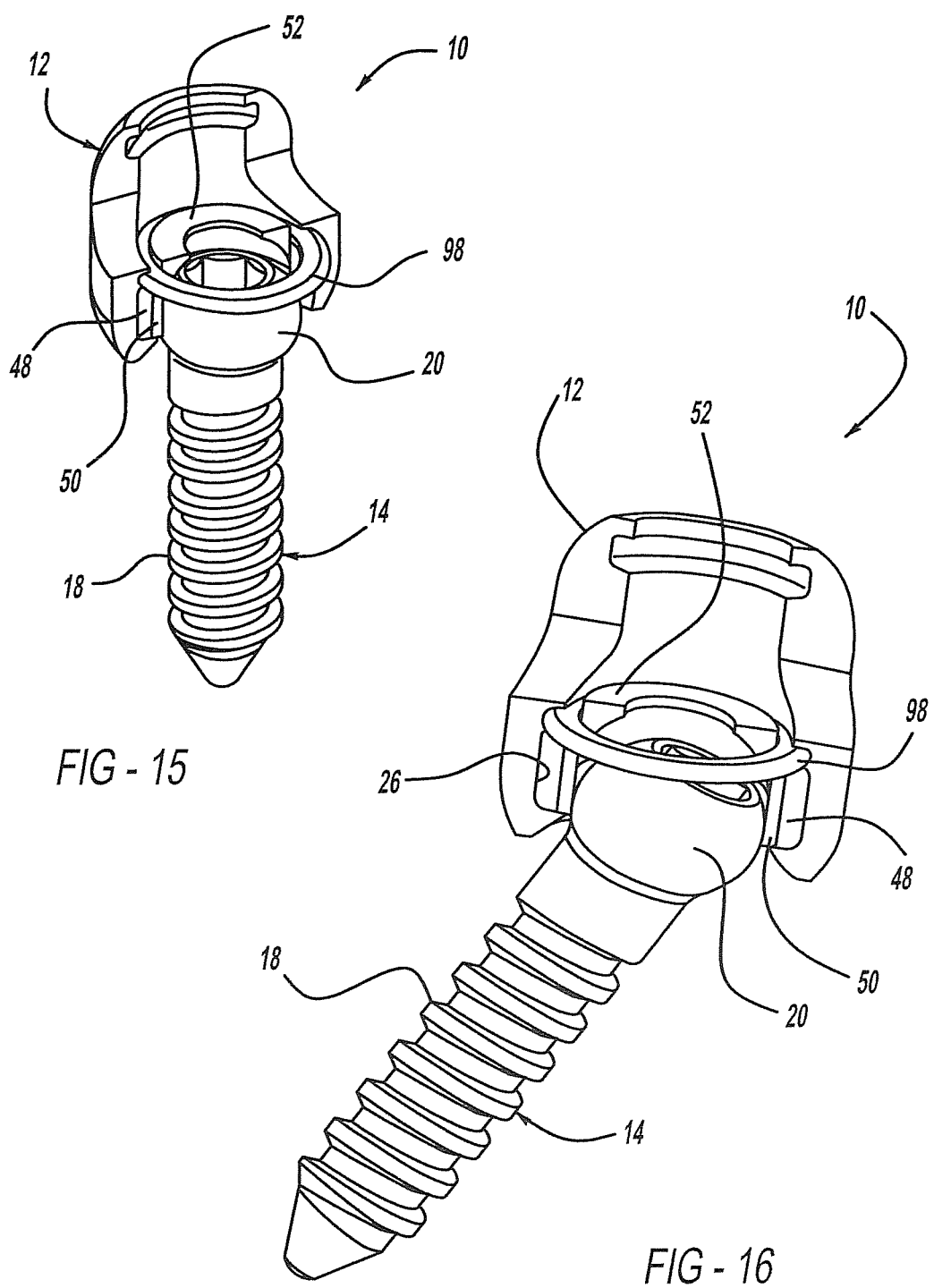
FIG. 15 is a perspective view showing the assembly, with the body member partially broken away.
FIG. 16 is an elevational view, partially broken away of the invention showing the screw member relative to the body member locked and angled.

The body member 12, as best shown in FIG. 6, includes an opening 22 extending therethrough defining a longitudinal axis indicated in FIG. 6 at 24.

The body member 12 can be divided into two subportions, a first subportion for retaining the head 20 of the screw 14 therein and a second portion for retaining the rod member 16 therein. The first portion for retaining the head portion 20 of the screw member 14 therein includes a recessed portion or surface 26 between a first lip 28 and second lip 30 which extend both radially inwardly into the opening 22. A third radially inwardly extending lip 32 defines a pocket 34 therebetween. The function of these recesses or pockets will be explained below.

Figure 5:
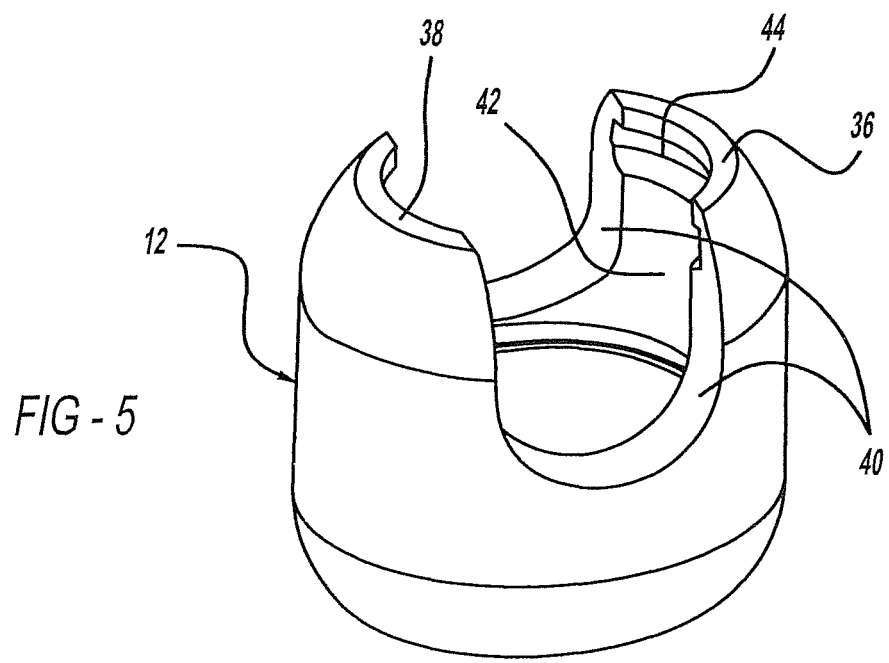
FIG. 5 is a perspective view of a body member made in accordance with the present invention.

The rod retaining portion of the body member 12 includes a pair of arms 36, 38, as best shown in FIG. 5. Between each of the arms 36, 38 is defined a U-shaped pocket or seat 40 such that a rod member 16 can be disposed within the pocket 40. The inner wall 42 of each arm 36, 38 includes a groove 44 for retaining a locking member therein as described in greater detail below.

The head 20 of the screw member 14 can be locked within the lower portion of the body member 12 by various means well known in the art. For purposes of illustration, the present invention includes a locking mechanism, the components of which are shown in exploded view in FIGS. 3 and 4. Specifically, an internal load dampening ring member 48 is retained within recess 26 of the body member 12 and prevented from escape by lip 28. Collar or locking ring 50 is disposed within the dampening ring member 48 and retained therein as the screw threaded portion 16 is disposed through each of the dampening ring member 48 and the collar 50 and the screw head 20 is seated against collar 50. Screw locking member 52 is disposed within opening 26 and retained therein by lip portion 30 thereby locking the screw head 20 in a substantially fixed position in the body member 12. The angle of the threaded portion 18 of the screw member 14 relative to the axis 24 of the body member 12 can be adjusted prior to locking of the screw head 20 thereby creating desired angulation, in its simplest form. Greater adjustment will be discussed below.

FIG. 7 shows an enlarged cross-sectional view of the locking ring 50 having an internal surface which is tapered at 54. As compression is applied against the screw head 20 between the locking member 52 and locking ring 50, the locking member 52 is driven into the locking ring 50 against the taper or curved surface 54 to compress against and lock in position the screw head 20. Another preferred variation is that the internal surface of locking ring 50 has an engagement portion that is smaller than the screw head 20. Compressing the screw head 20 downward into this smaller diameter area creates force on the screw head 20, thereby locking the angle of the screw. Again, other variations of locking mechanisms can be utilized in accordance with the present invention. FIGS. 9-12 illustrate the screw head 20 and the various components used above locking the screw member 14 relative to the body member 12. It is also possible to adjust the locking ring 50 and screw head 20 such that the screw can be locked at specific loads and when those loads are exceeded, the screw head 20 moves in the locking ring 50.

Figure 19:
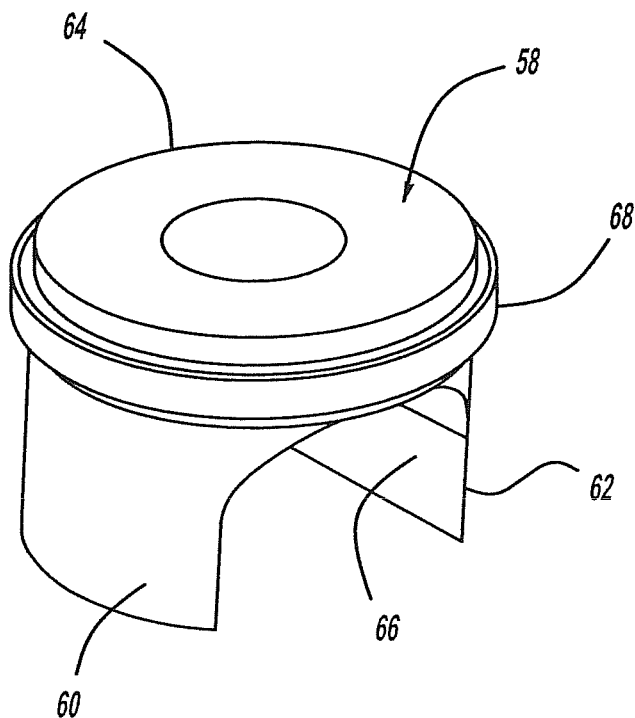
FIG. 19 is a top perspective view of the rod locking member of the present invention.
Figure 20:
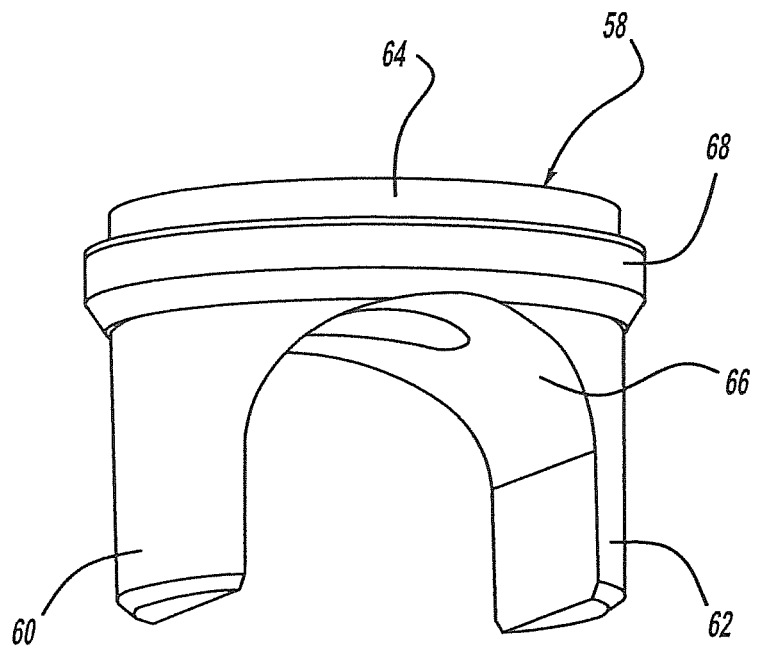
FIG. 20 is a bottom perspective view of the locking member.
Figure 22:
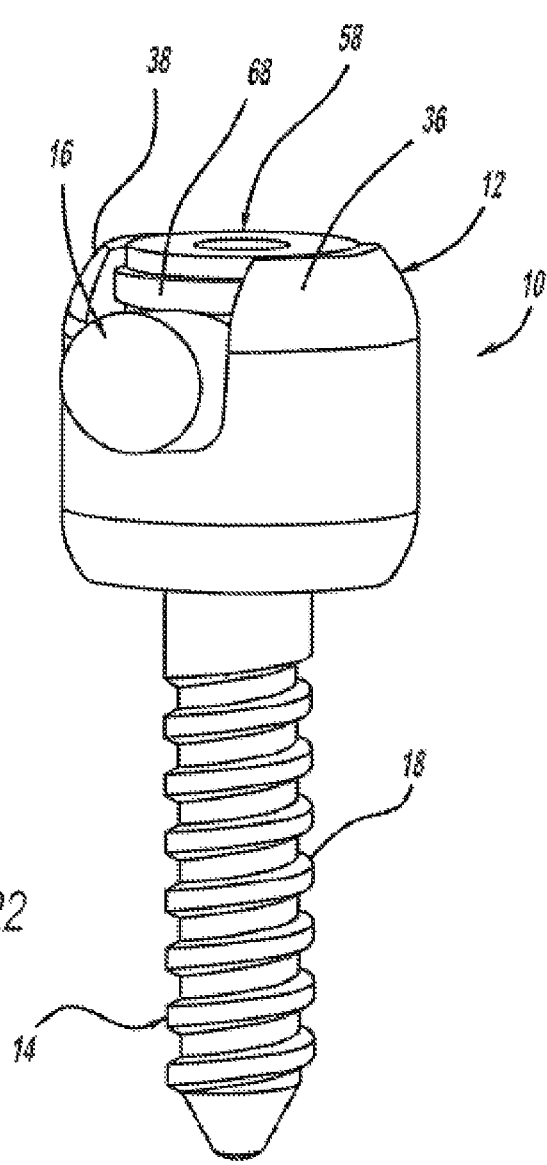
FIG. 22 is an assembled perspective view of the present invention with the rod member locked therein.
Figure 23:
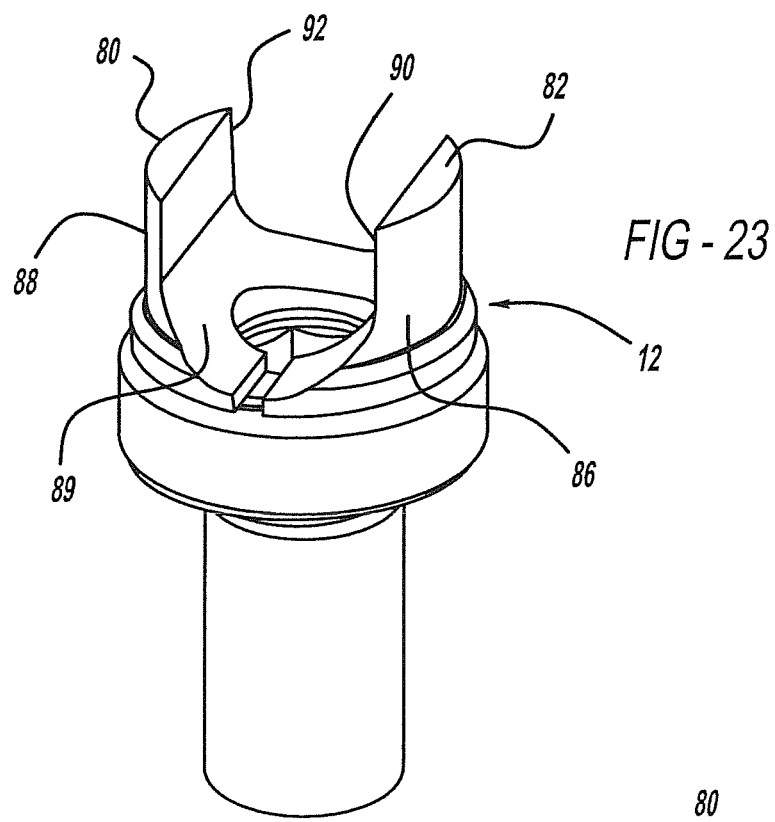
FIG. 23 is a top perspective view of the body member of the present invention.
Figure 24:
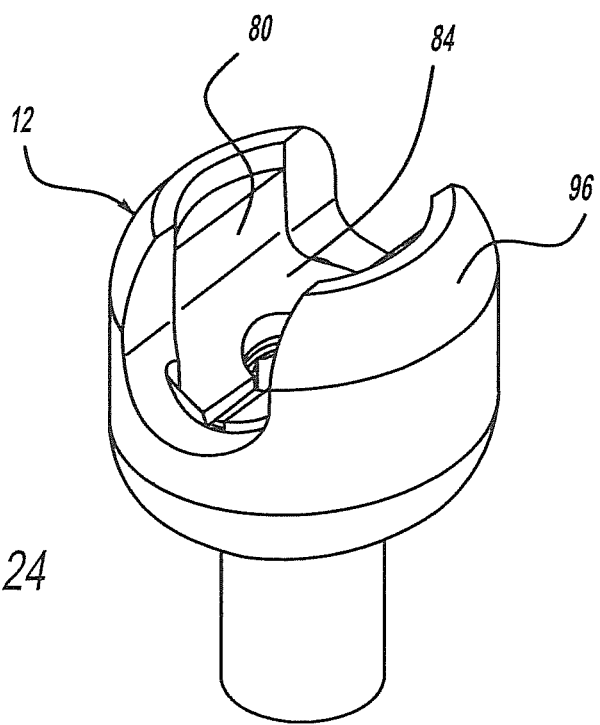
FIG. 24 is a top perspective view of the body member of the present invention including the locking ring for locking a rod therein.
Figure 25:
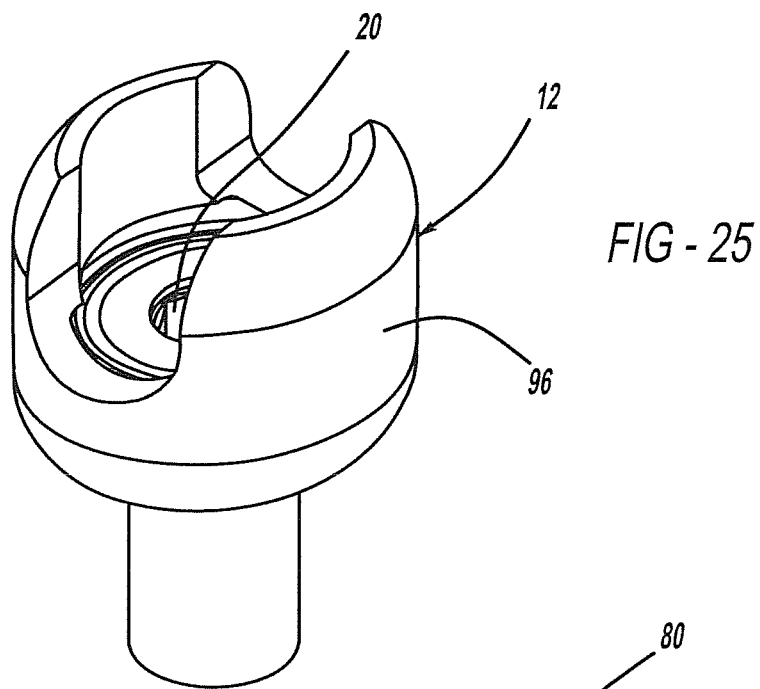
FIG. 25 is a side perspective view of the assembly shown in FIG. 24.
Figure 26:
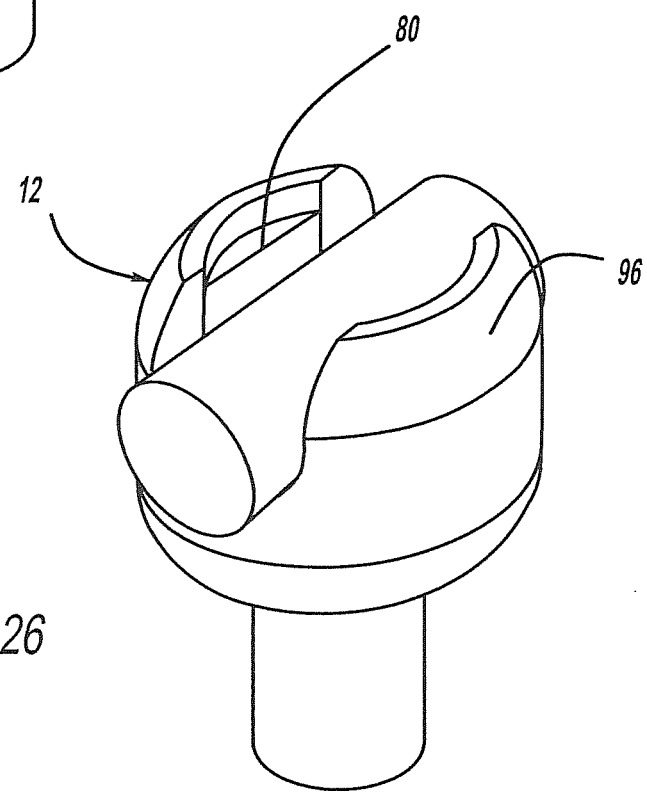
FIG. 26 is an alternative embodiment of the present invention.
Figure 27:
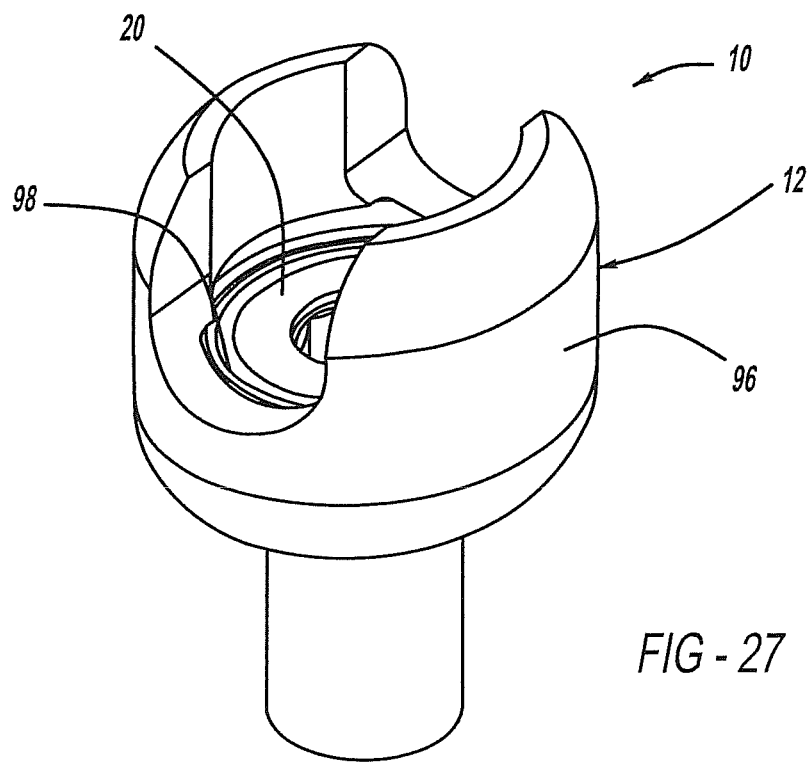
FIG. 27 is a top side perspective view of the present invention.

As discussed above, the arms 36, 38 form a U-shaped recess or pocket 40 for receiving a rod member 16 therein, as shown in various views, for example, FIGS. 1, 2, and 22. The rod member 16 is fixedly retained in the pocket 40 by means of a locking member, generally shown at 58 in various figures. FIGS. 19 and 20 show the locking member 58 in a top and bottom perspective view, respectively, the locking member 58 being a substantially U-shaped member when viewed in elevation, including leg portions 60 and 62 and base portion 64 combining to form a substantially U-shaped pocket 66. A radially outwardly extending rib 68 projects from an annular peripheral surface of the base portion 64.

Figure 21:
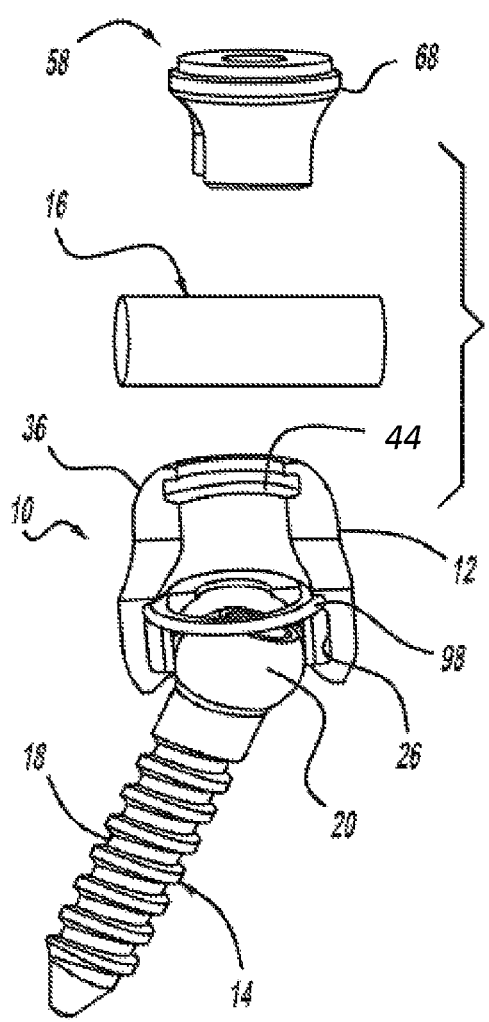
FIG. 21 is a partially exploded view of the present invention with the rod member not locked within the present invention.

FIG. 21 shows an exploded view of the screw member 14 secured within the body portion 12, the details of which will be described below. The rod member 16 is disposed above the portion of the body member 12 that will receive the rod member 16, the locking member 58 being separate from the assembly. FIG. 22 shows the rod member 16 captured within the substantially U-shaped pocket 40 of the body member 12 with the locking member 58 capturing the rod member 16 between the substantially U-shaped pocket 66. The pockets 40 and 66 engage the rod member 16 to fixedly secure it in place as the rib 68 of the locking member 58 is engaged and secured within recess 44 formed in each of the arms 36, 38 of the body member 12.

Figure 29:
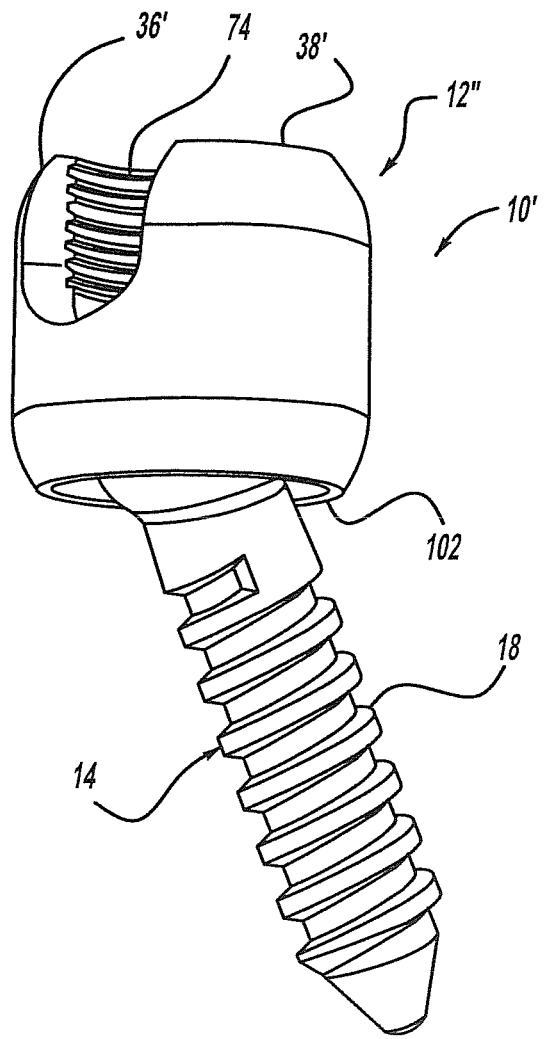
FIG. 29 is an elevational view of a further embodiment of the body member of the present invention retaining a screw member therein.
Figure 30:
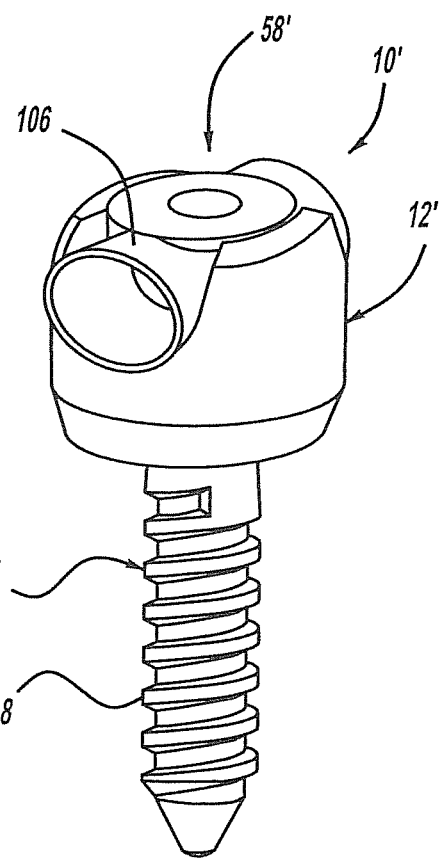
FIG. 30 is a perspective view of a further embodiment of the present invention.

The structure of the body member 12 relative to the locking member 58 can be modified, such as the body member 12 including an inwardly radially projecting rib, which would mate with a recess formed in the locking member 58. Likewise, other locking member configurations can be contemplated and executed in accordance with the present invention. For example, FIG. 29 shows arms 36', 38' including a threaded inner surface 74. As shown in FIGS. 30-32, the locking member 58' includes a threaded outer surface for threadingly engaging the threaded inner surface of the arms 36', 38' and thereby locking down upon the rod member 16 disposed therein. Again, there are other locking mechanisms either known in the art or not yet contemplated that can be used in accordance with the present invention in order to fixedly secure the rod member 16 within the body portion 12 thereby interconnecting the rod member 16 to the vertebrae in which the screw member 14 is implanted.

For example, FIGS. 23-27 show an alternative locking mechanism, which is a collet type locking device that eliminates the requirement of a retaining ring within the assembly. Such a system is shown in U.S. patent to Richelsoph et al., issued Mar. 12, 2002, which loses a body member 12 including a pair of flexible arms 80, 82 defining a U-shaped flexible seat 84. The flexible arms 80, 82 allow for free slidable adjustment of a rod 16 disposed within the seat. The rod is in an uncompressed condition when the rod is seated within the seat thereby allowing for movement of the rod within the seat. The arms 80, 82 have a smooth outer surface 86, 88 and an outwardly flared end portion 90, 92 which is compressed in a rod receiving member 96 for locking the rod 16 in position relative to the body member 12. Again, the construction can be reversed such that the collet is smooth on the arms without an outward flare and the body member includes a ridge, such that the arms are pushed further against the rod as the collet is pushed into the body. In other words, various aspects of the general structure described above can be modified within the contemplation of the present invention.

A significant aspect of the present invention is internal load dampening means which share and dampen loads between at least one screw member 14 and at least one rod member 16 interconnected by said assembly 10. More specifically, the body member 12 includes the screw seat 26, which seats a screw head 20 therein. The load dampening mechanism includes at least a portion of the screw head seat, the screw head seat being defined as the walls containing the screw head seated within the body member 12. In the specific embodiment shown in the Figures, and presently specifically referring to FIGS. 3 and 4, the screw head 20 is disposed between locking ring 50 and locking member 52 within the recess 26 of the body member 12. Washer or snap-ring member 98 shown in the exploded views of FIGS. 3 and 4, is fixedly disposed within recess 34 of body member 12. Assembled views are shown in FIGS. 13-18 and 22. The load dampening ring member 48, when positioned in abutting engagement against the locking ring 50 provides a load absorbing mechanism against which forces generated by moving vertebrae through screw member 14 can be absorbed within the assembly 10. The recess 34 provides ring retainer means for retaining the snap ring member 98 therein. The snap ring member 98 defines an upper wall against which the screw head 20 and screw head locking mechanism 50, 52 abuts thereby allowing the resilient retainer ring 48 to flex and absorb loads within the assembly 10. Of course, the resilient ring 48 absorbs loads traveling both ways through the assembly 10 such that loads placed on rod member 16 through the body member 12 are absorbed and dampened as they are transmitted to the screw member 14. This allows for greater adjustments of rod position during reduction, while preventing loads from being transmitted wholly to a single screw or multiple screws. Rather, loads are transmitted through the rod member 16 through the various screws interconnected to the rod by the various body members 12 including the load dampening mechanism of the present invention.

Alternative configurations of the load dampening mechanism can be contemplated, such as wherein various walls 26 of the body member are flexible thereby also dampening loads transmitted from a rod member 16 to a screw member 14 or vice versa. For example, the entire wall of the body member 12 can form a cup around the head 20 of the screw member 14 and locking mechanism thereof to provide load dampening in all directions about the screw head 20. Alternatively, the entire locking mechanism can be a load absorbing material so as to be able to dampen loads placed on the screw head 20 or the body member 12 which are transmitted therebetween. The dampening member would be a lining entirely covering a surface of the screw head 20 within the screw head seat.

The rod member 16 can be made from various materials, such as titanium alloys, cobalt chrome, and stainless steels. These materials can also be coated for additional strength and/or lubricity.

Consistent with the alternative embodiments discussed above, the body member could be made from a load absorbing material or the seat portion of the body member can be made from a load dampening material, such as metals and plastics well known in the art. Likewise, the body portion 12 can be made from a dual durometer material wherein the screw head seat can be made from a more absorptive load dampening material and the rod retainer portion can be made from a more inflexible material. Such methods of making dual durometer parts are well known in the art.

The screw head 20 seated with the body member 12 but not locked experiences a self-centering effect due to the biasing of the load dampening ring 48. Thus, the present invention further provides a self-centering mechanism for self-centering a screw in the body member 12 in an unlocked condition.

Figure 28:
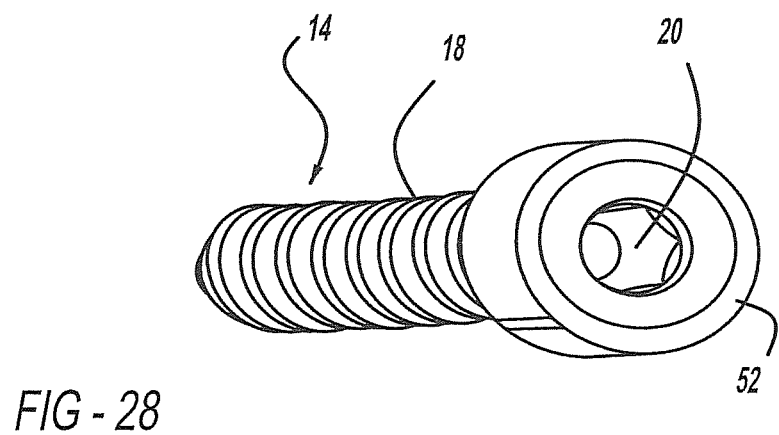
FIG. 28 is a perspective view showing the screw head top portion.

FIG. 28 shows a further inventive aspect of the present invention. Having a round load sharing/dampening element 48 around a round internal locking mechanism will lock the screw 14 at an angle (an angular lock screw as shown in FIG. 29) but can still rotate in the body 360° along the long axis 24 (shown in FIG. 6) of the body member 12. The lower face 102 (shown in FIG. 6) of the body member 12 and the retaining ring or lower end of the collet in the embodiments discussed above, prevent motion that is not sliding perpendicular to the axis of rotation. In this case, the friction of the load sharing/damper ring 48 against the inside of the body member 12 controls the force required for rotation. This rotation is controllable by a variety of means.

In one embodiment, if the external surface of the locking mechanism comprising rings 50 and 52, shown in FIGS. 3 and 4, are not round, and the load sharing dampening element 48 is not round, then this changes the ability of the entire combined mechanism 48, 50, 52 to freely rotate within the body member 12. For example, as shown in FIG. 28, the outside surface of the locking mechanism 52 in combination with rings 48, 50 (not shown in FIG. 28) is oval. The larger the oval, the more force is required for rotation. If the internal body recess 26 (as shown in FIG. 6) is also oval, and the oval of the locking mechanism 52 is large enough such that one edge of the oval contacts the side of the internal body wall 26 when rotated, then the amount of rotation can be directly controlled to the desired amount. This geometry can be in other shapes, including square or rectangular, or a combination to accomplish the same effect. Thus, this geometry provides a screw rotation control mechanism for controlling the force required to rotate a screw along an axis perpendicularly to an axis defined by the length of the body member 12 retaining the screw 14 therein. This is accomplished by the inner surface 26 of the body member 12 and the outer surface of the seating mechanism comprising the locking rings 48, 50 and 52 having the oval cross-sectional shape. As stated above, this cross-sectional shape could be square, hexagonal, or other shapes.

What is key to greater adaptability of the present invention to various final configurations and needs for reduction is not the rotation of the screw member 14 relative the body member 12, but rather the overall motion parallel to the loads exerted on the rod 16. By allowing controlled motion as used above, the loads to the pedicle and spine can be moderated in multiple directions. This is done with standard spine rods and without the need for PEEK rods, or a complex motion mechanisms of the prior art. Such an approach has advantages.

For example, it is well understood that a level that is fused alters the spine loads exerted on the levels above and below the fusion. By allowing the loads at the unaffected levels to be moderated and reduced, the healthy or relatively healthy disks are much better preserved. Hence, problems of the prior art wherein fusion results in eventual degradation of adjacent disks is minimized or avoided.

In addition, if motion in all planes is required for a perpendicular load sharing and dynamic system, then the load sharing damper mechanism of the present invention can encapsulate the locking mechanism 52, as used above. In this manner, all surfaces of the internal locking mechanism are suspended away from the internal recess 26 of the body member 12. Thus, motion is allowed in all directions, but the amount of motion based on the distance or gap between the internal locking mechanism 48, 50, 52 and the internal body wall 26.

The present invention allows the above-discussed sliding mechanism to be locked in place by direct pressure or mechanical engagement with the rod locking mechanism used above. While this does not allow for load sharing and dampening as there is direct locking force from the rod to the screw head, it does provide a benefit, especially in cervical spine applications. By allowing the screw 14 to slide, the amount of screw angulation increases (screw angulation being defined as the angle between the long axis of the screw member 14 and the axis 24 of the body member 12.) For example, as the screw 14 slides to the right, a larger gap between the lower edge of the body member 12 and the screw 14 on the left side occurs. The screw can now rotate further to the left without hitting the lower edge 102 of the body member 12 as shown in FIG. 29. Thus, the present invention provides a seat mechanism for seating a head 20 of a screw 14 therein and includes an outer surface seated within an inner surface of the body member 12 and a mechanism for locking the screw within the body member such that a gap between the inner and outer surfaces allows motion of the screw 14 relative to the body member 12 when the screw is locked within the body member thereby increasing angulation of the screw long axis relative to the axis 24 of the body member 12.

In cervical spine manipulations, a high angulation screw is often required. The load sharing damper of the present invention allows some increased angulation already by the present approach and it is possible to adjust this combination of load sharing damping with increased screw angulation according to requirements.

If all of the benefits of the above-described system are considered, then it can be seen that there are benefits to using such a polyaxial screw assembly 10 with a pediatric scoliosis system. In such a system, the spine elements are generally present and intact, but the curve of the spine requires means to straighten it. Fusion of the spine is normally the treatment of choice as used above in detail, and pedicle screw fixation with rigid rods to hold the spine straight during the fusion process is the preferred treatment. However, it would be far better to utilize the present invention that shares the load with the spine, allows for correction, and does not require fusion, but is allowed to grow with the patient. A completely rigid screw, as is common in the current art, would not be effective in accomplishing this goal. The rods are contoured to match what the spine curve should be and the screws are rigidly fixed to the pedicles and rods. If a rigid screw were to slide along the rod, it would have infinite difficulty in moving along the curves. In addition, the change of the curvature would create extremely high loads on the pedicle, risking not only fracture, but abnormal changes in the desired curvature. This is because as the spine grows, the screw would be pushed into a different location on the rod that may have a different curvature. However, utilizing the present invention, the load is moderated and the assembly can be moved relative to the rod to maintain relative alignment without being rigidly fixed to the rod.

To accomplish the above goal in a scoliosis manipulation or other manipulation where there would be spinal growth during treatment, the amount of motion is controlled by the gap between the body member 12 and the internal locking mechanism 48, 50, 52 and the load sharing damper material properties. The more gap, the more potential motion. It is therefore possible to make the body member 12 larger or larger only in one direction, such as oval or rectangular, such that the screw member 14 can move greater distances in one direction, such as along the rod.

Secondly, if there is no rod locking mechanism, but a sliding mechanism, the height of the assembly is significantly reduced and the system will literally grow with the spine. An example of such a mechanism is shown in FIGS. 30, 31, and 32. These Figures show a body member 12' for interconnecting the screw member 14 to at least one rod member 16 wherein the body member 12' includes a slidable rod retaining mechanism for retaining a rod member therein while allowing sliding movement of the body member 12 relative to the rod 16. More specifically, the rod member 16 is retained within a sliding tube 106 disposed over the rod member 16. The sliding tube can be made from various materials such as titanium, cobalt chrome, stainless, or one of these materials treated or coated to improve wear properties. Treating the surface with nitrides or coating in titanium nitride, or diamond like coatings are just a few of the possibilities. The sliding tube can also be lined with a plastic, such as polyethylene.

Figures 33, 34:
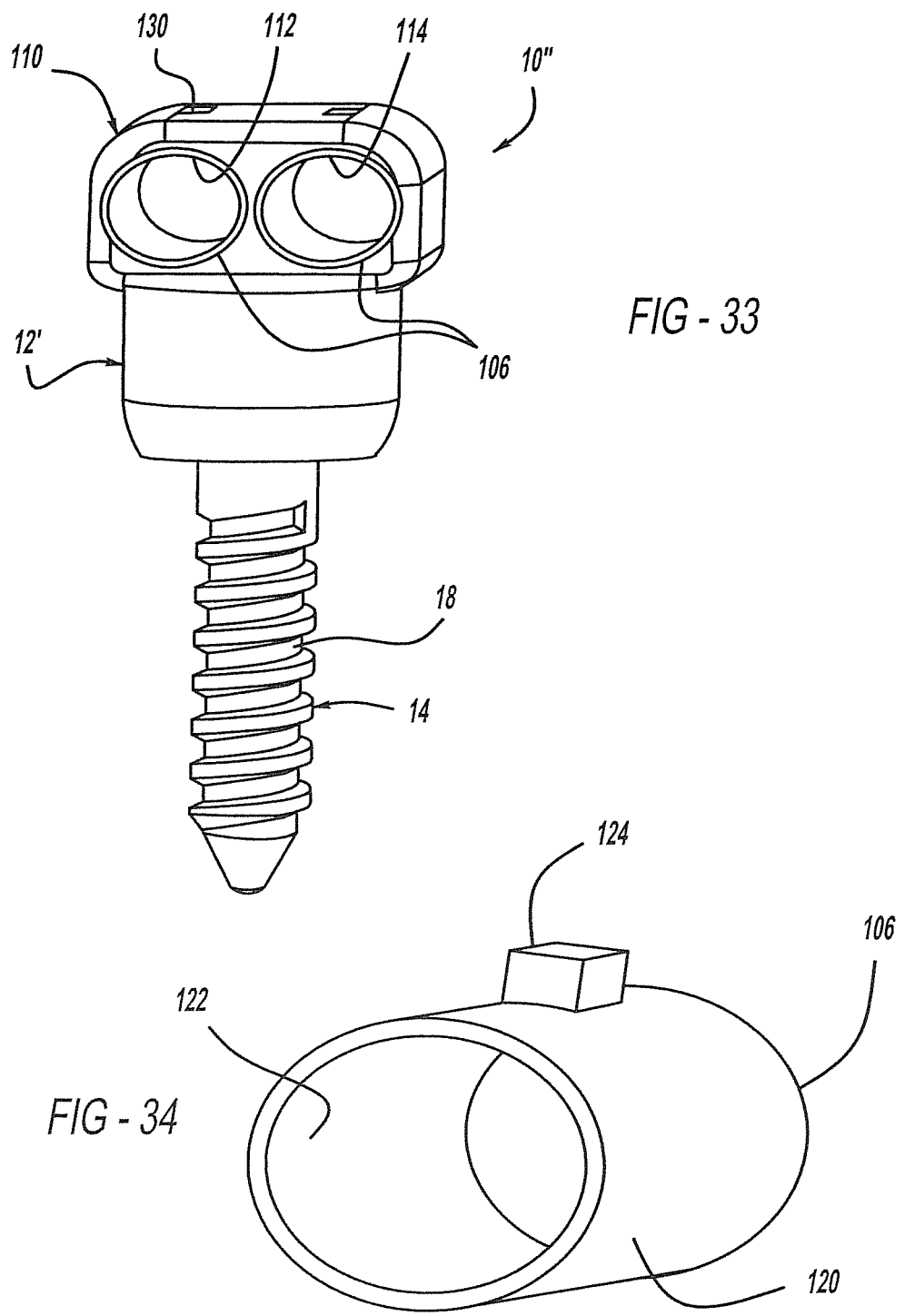
FIG. 33 is a perspective view of a further embodiment of the present invention.
FIG. 34 is a perspective view of a rod retaining bearing made in accordance with the present invention.

FIG. 33 shows an alternative version 10" of the present invention primarily for the treatment of pediatric scoliosis or, again, other pediatric manipulations wherein there will be growth of the spine during treatment. This version allows for minimally invasive reduction of scoliosis by allowing for smaller rod segments to be effectively connected by a dual sliding mechanism generally indicated at 110. The dual sliding mechanism 110 includes two ports 112, 114. Disposed within each port is a slidable sleeve 106. The dual port sliding mechanism 110 is also constructed so as to rotate 90° relative to the long axis of the screw member 14 to enable reduction.

By way of background, there are two basic forms of scoliosis reduction. Derotation involves creating the correct curvature for the spine in one plane and then rotating it 90° such that the curve forces the spine back into a normal shape. The rod is used as a cam for this purpose. The second method is a cantilever approach, wherein the rod is not rotated, but the rod is formed with the correct curvature and the screw brought to the rod or vice versa at each level that is secured to the rod. As a system in the earlier figures can easily accomplish the cantilever approach, the following approach is a unique method for derotation.

As best shown in FIG. 33, the body portion 12' includes the retainer portion 110 having internal bearings 106 attached thereto. The bearings 106 include an outer wall, as best shown in FIG. 34 at 120 in an inner wall 122. Projecting radially outwardly from the outer surface 120 is a locking tab 124. Two of the bearings 106 slide within the rod retainer portion 112, 114 and are held in place by the tabs 124. The tabs 124 are depressible such that the bearing members 106 can rotate within the rod retainer portion when the tab 124 is not aligned with and inserted into openings 130.

Figure 35:
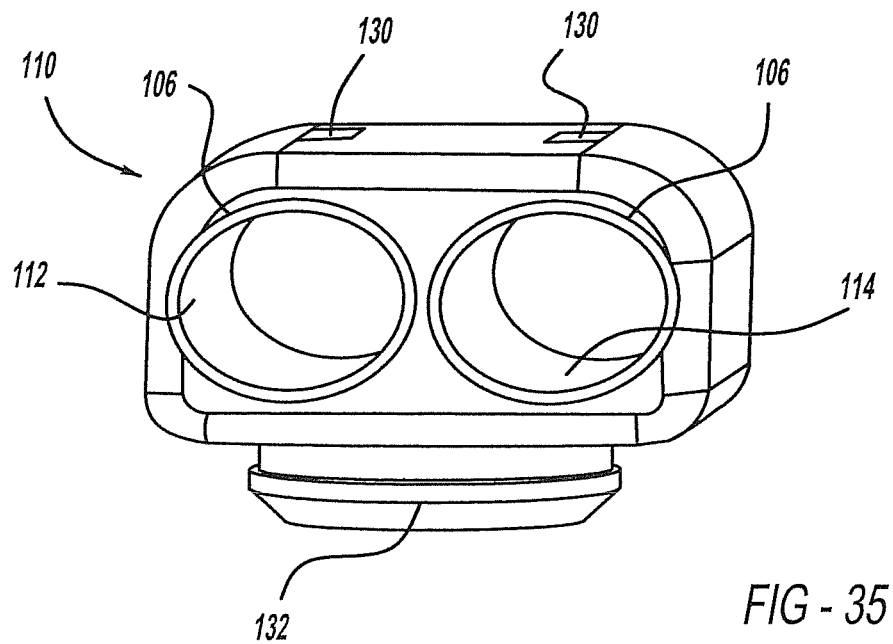
FIG. 35 is a perspective view of a rod bearing retaining assembly made in accordance with the present invention.
Figure 36:
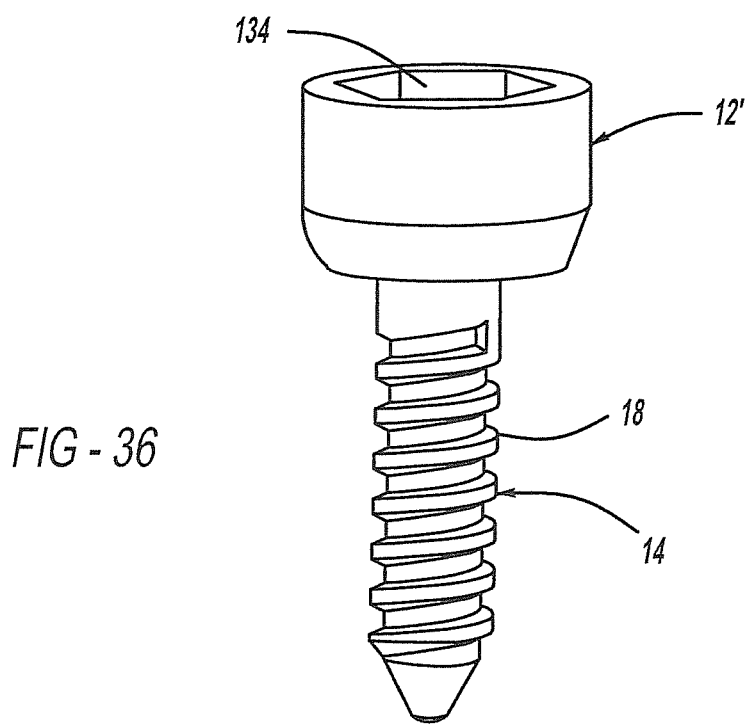
FIG. 36 is a perspective view of the body member retaining a screw including means for retaining the rod bearing retaining assembly.

In FIGS. 35 and 36, one embodiment of securing the rod retainer portion 110 to the body portion 12' is shown. The rod retainer portion 110 includes a radially outwardly protecting hex portion 132, which can be fixedly seated within a groove 134 within an inner surface of the body portion 12'. The body member 12' captures and aligns the head to the body member 12'. An opening 136, as best shown in FIGS. 40, 41, and 42, allows access to locking the screw portion.

Figure 37:
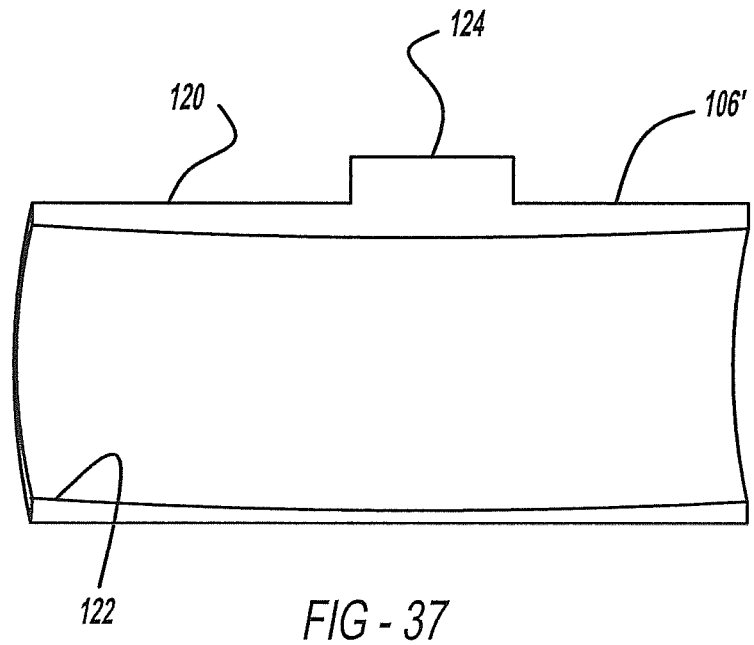
FIG. 37 is an elevational, cross-sectional view of the rod bearing of FIG. 34.
Figure 38:
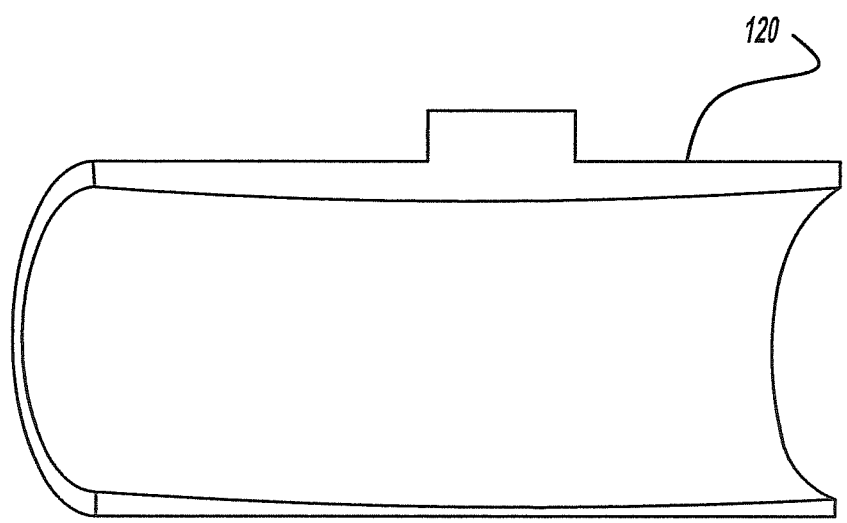
FIG. 38 is a perspective, cross-sectional view of the rod bearing of FIG.34.

FIGS. 37 and 38 show the inside of the bearing 106' for use with a curved rod. The inside of the bearing 106' is formed with a curve matching the curve of the preferably pre-bent rod. FIG. 39 shows the bearing 106' fit with a curved rod 16'.

Figure 42:
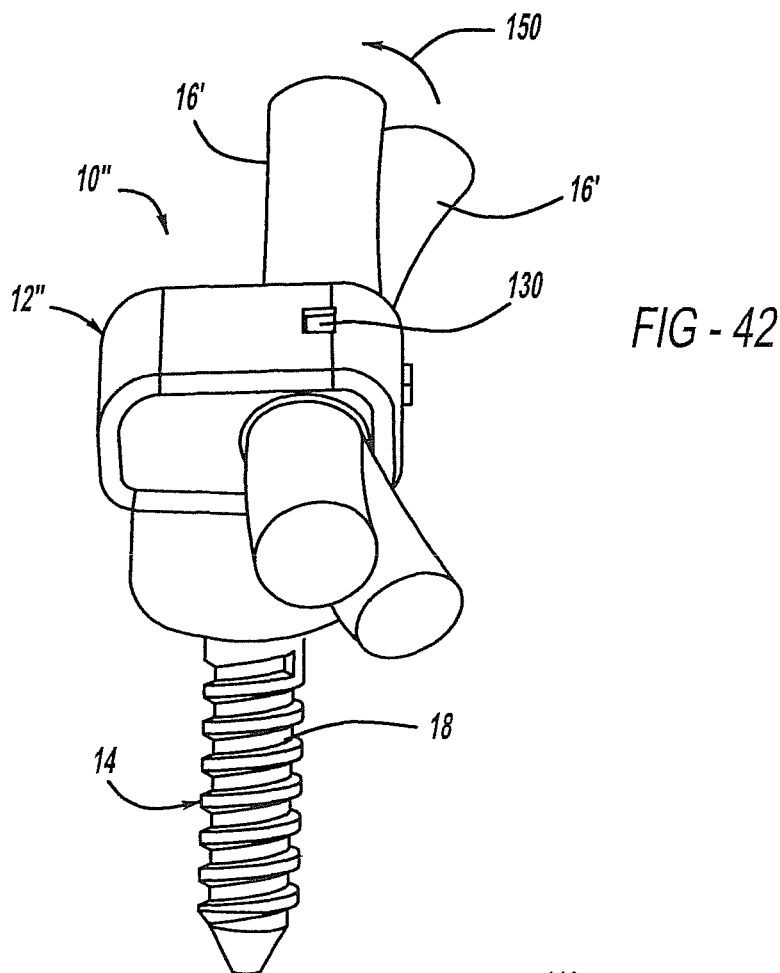
FIG. 42 shows a perspective view of the present invention indicating rotation of the rod member within the assembly 90°.
Figure 43:
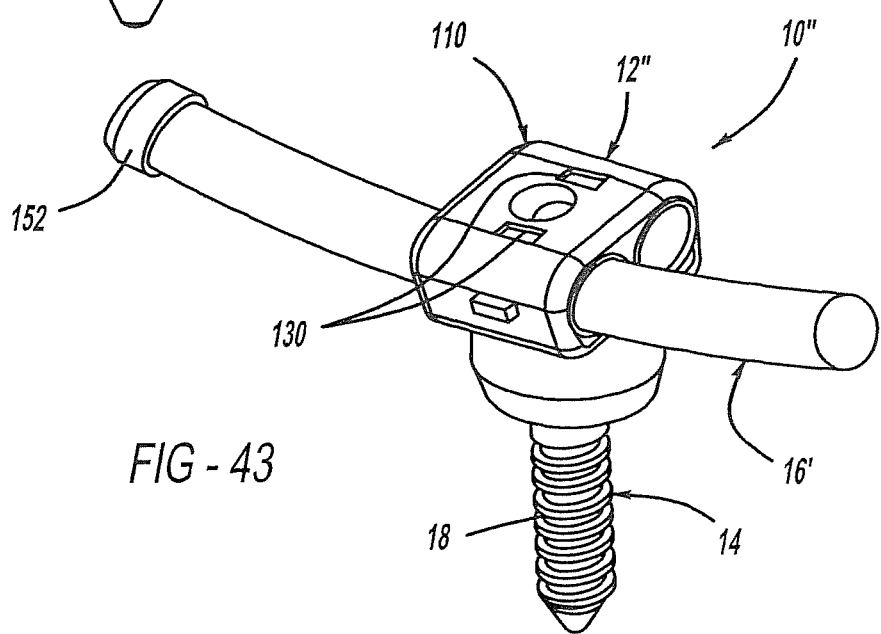
FIG. 43 is a side perspective view of a further embodiment of the present invention retaining a curved rod therein.
Figure 44:
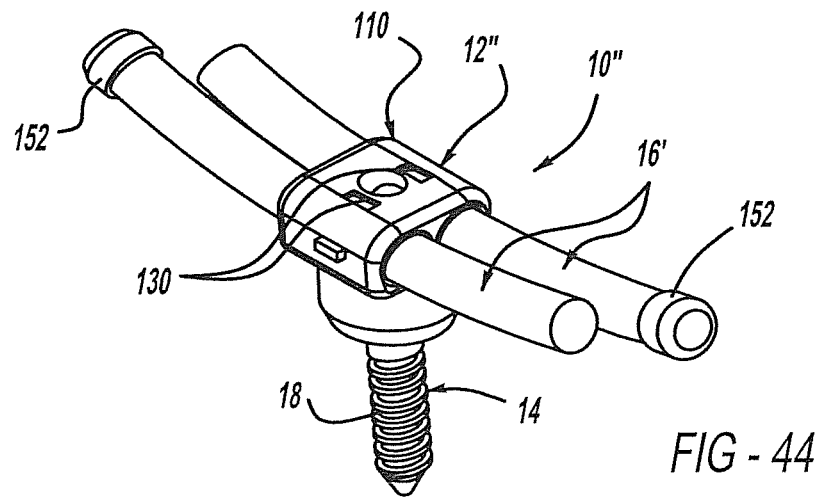
FIG. 44 is a perspective view of the assembly made in accordance of the present invention retaining two rod members therein.
Figure 45:
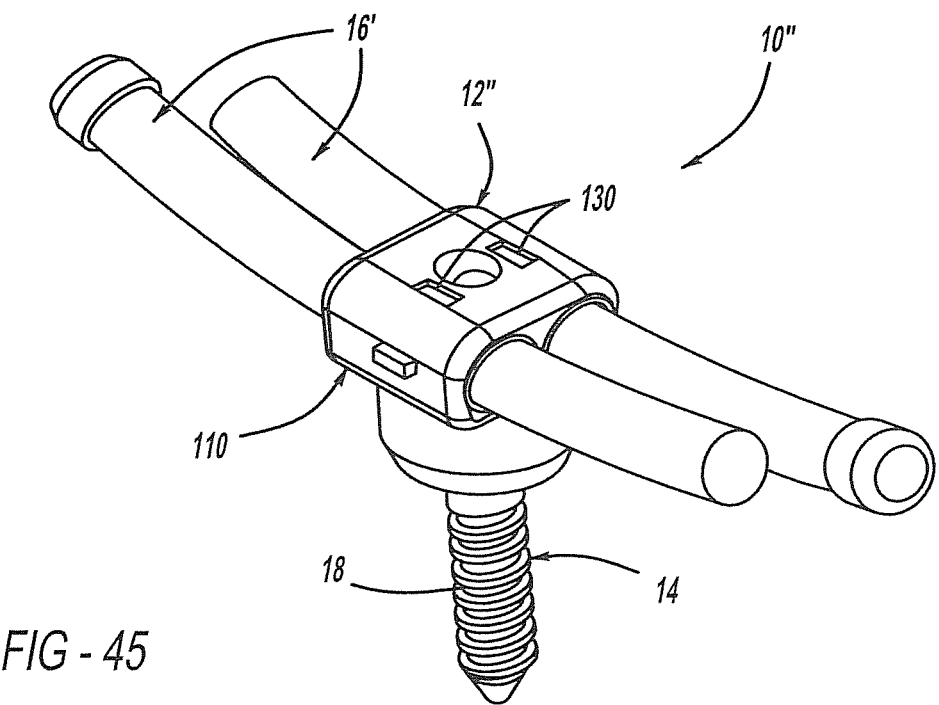
FIG. 45 is a perspective view of the present invention also showing two rod members retained therein.

For scoliosis reduction via derotation, the curved rod 16' is inserted into the bearing 106' such that the curve is aligned on the coronal plane, as shown in FIG. 42. Upon rotating the rod, as shown in FIG. 42 by arrow 150, a bearing moves in the rod retainer portion until the curve is aligned with the sagital plane. When the bearing reaches the 90° rotation, the locking tab 124 engages the rod retainer portion and locks into place. This can be best seen in FIGS. 40, 41, and 42. FIGS. 43, 44, and 45 show the rods with the addition of end caps 152 such that the rod 16' cannot slide out of the retainer 110. FIGS. 44 and 45 show the dual rod construct to connect multiple levels and allow derotation at each level individually.

FIG. 46 shows a stop mechanism for preventing further movement of the body members 12" along the rod 16' beyond the rod stop mechanism. The rod stop mechanism shown is a pair of collets 156 crimped or otherwise fixedly secured to rod 16' at a predetermined distance apart which abut against the body members 12" to prevent the body members from sliding closer to each other than the predetermined fixed distance defined by the collets 156. Such collets or locking collars 156 can be utilized to decompress a nerve. For example, the locking collars 156 can be placed on the rod 16'. These collars 156 can be either slid on the rod beforehand (closed round rings) or after the rods are placed via a C or U-shaped collet. The collets 156 can be crimped or fastened by other means, such as by a set screw. This technique allows for a set distance to be maintained between the body members 12", but still allows outward sliding along the rod 16'. The body members 12" fixed to vertebrae (not shown) can spread apart from each other as the vertebrae grow. The present locking mechanism for the screw head 20 in combination with the sliding rod retaining members 110 allow for growth of the assembly 10" with the growing spine. Such a system is extremely well suited for pediatric use, especially in the treatment of scoliosis.

An alternative approach to the above is a spacer tube (not shown) which is effectively a length of tubing that simply slides along the rod 16'. The tube is placed between the screw bodies thus maintaining space therebetween. This allows both screws 14 to effectively slide along the rod 16' without any stops, but the distance between the screws is always held apart at least a minimum amount no matter where the screw or screws slide.

Figure 50:
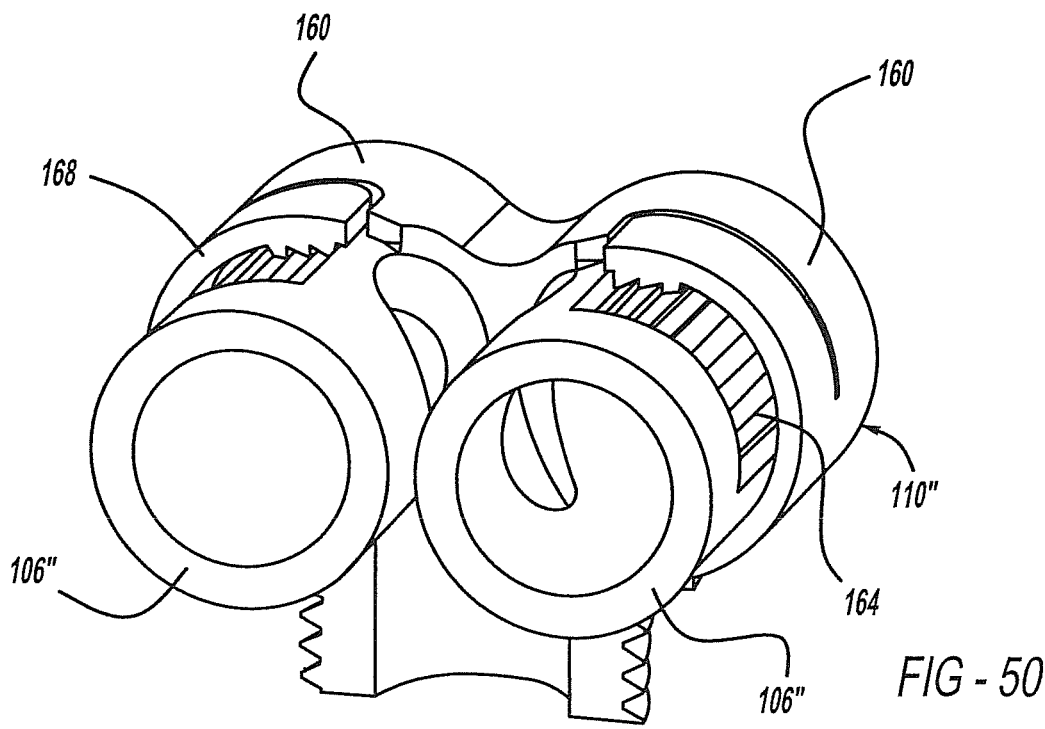
FIG. 50 is a further embodiment of a dual rod retaining body member assembly.
Figure 51:
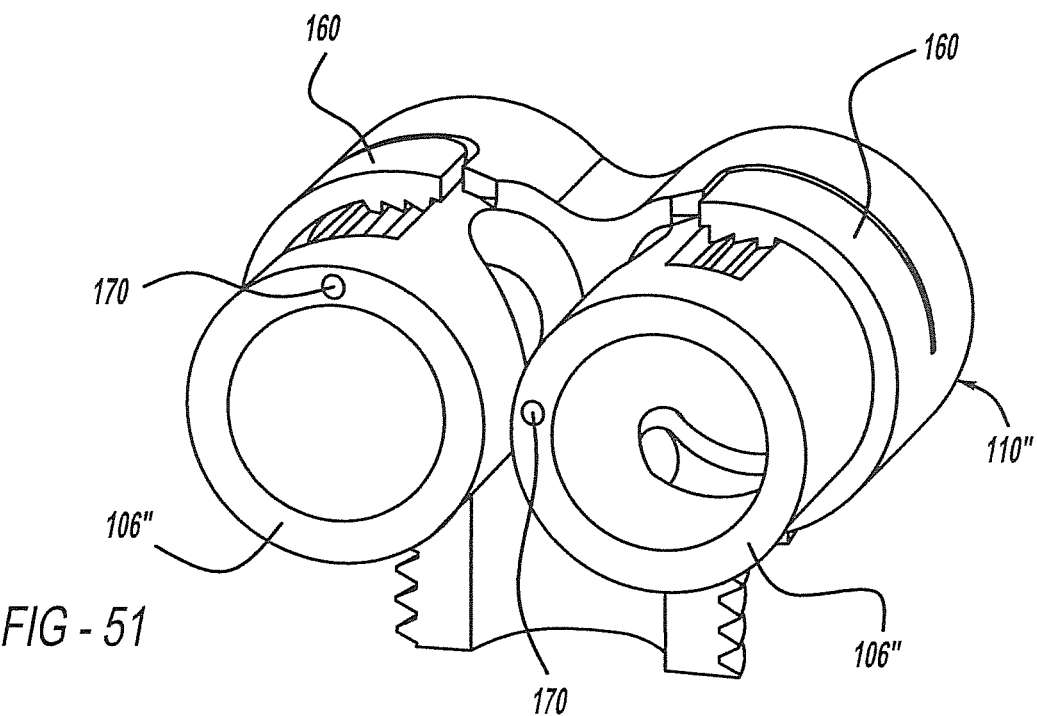
FIG. 51 is another embodiment of the rod retaining body member including bearing members rotated therein.
Figure 52:
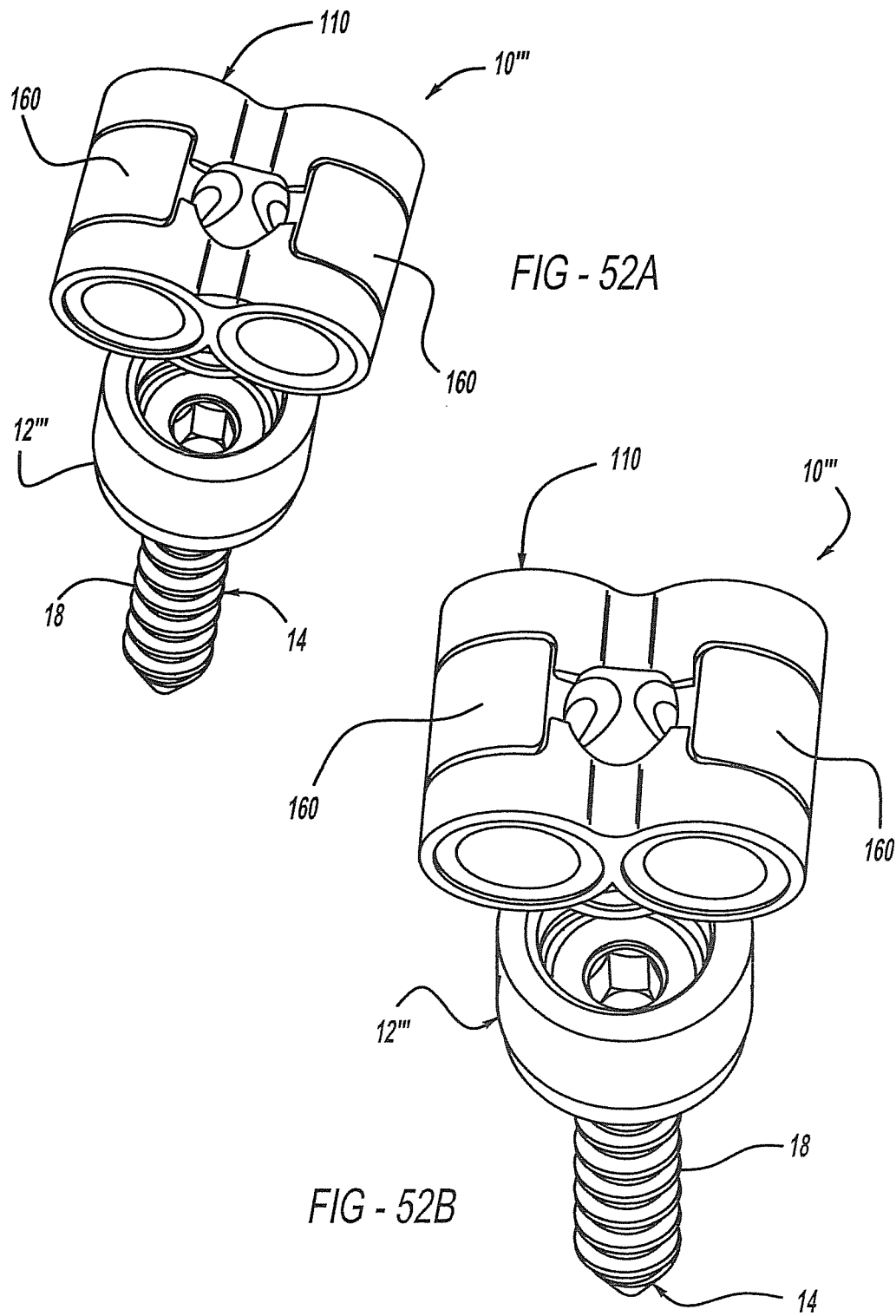

FIGS. 47-53 show an alternative mechanism for allowing or preventing rotation of the rods 16 within the rod retainer. As shown in FIGS. 47a and 47b, the bearing holder 110' includes at least one bearing 160 (two are shown in each figure) each having a flexible portion with internal teeth 162. The bearing holder 160 is flexible so as to be able to bias outwardly to a non-lock position and radially inwardly to a locking position. Each bearing member 106", as shown in FIGS. 48a and 48b include indentation or teeth 164 machined into the outer surface thereof. Thus, as best shown in FIG. 49b, the engagement of teeth 162, with teeth 164 can prevent relative rotation therebetween. Outward flexing of arms 160 releases the teeth 162, 164 from each other thereby allowing relative rotation in both directions. The teeth can be configured, as shown best in FIG. 49b, to allow rotation in one direction while blocking rotation in the other unless in the unlocked, outwardly biased condition. Thus, the rod can be rotated in one direction during reduction yet prevented from derotating or vice versa. FIGS. 50 and 51 show the bearing member 106 including the tooth configuration preventing reverse rotation. The teeth configuration 164 on the outer surface of the bearing members 106" also allows for the bearing member 106" to be inserted within the bearing retainer member 110" and held without any other additional components. Opening 168 allows for instrument access to the polyaxial mechanism. This opening also allows easy observation of the rotation of the bearing members 106.

FIG. 51 shows the relative rotation of the two bearing members 106", two dots 170 being placed at the normal non-rotated position. The bearing on the right in FIG. 51 is then rotated. Once rotated, the flats of the teeth 154, 166 engage and will not allow the bearing to rotate back. For revision of adjustment, the springs 160 can be moved upward to disengage the teeth to allow rotation.

The use of multiple positions for teeth engagement allows for locking during derotation at various points. Thus, if the spinal curve is reduced to an acceptable level at partial rotation of the bearing, it is not necessary to rotate further. In addition, in a minimally invasive approach, it is ideal to do the curve reduction incrementally and without the need for locking the rod to the assembly and having to unlock it to make adjustments. The use of multiple position self locking allows for the implant system to hold position without extra surgical steps. In addition, the relative position of the bearing can be relayed by an instrument to the surgeon, such that the surgeon knows by degrees the amount of derotation that has been done without having to see the implants under the skin and muscle. This is very important for a minimally invasive approach.

Figures 53, 54A:
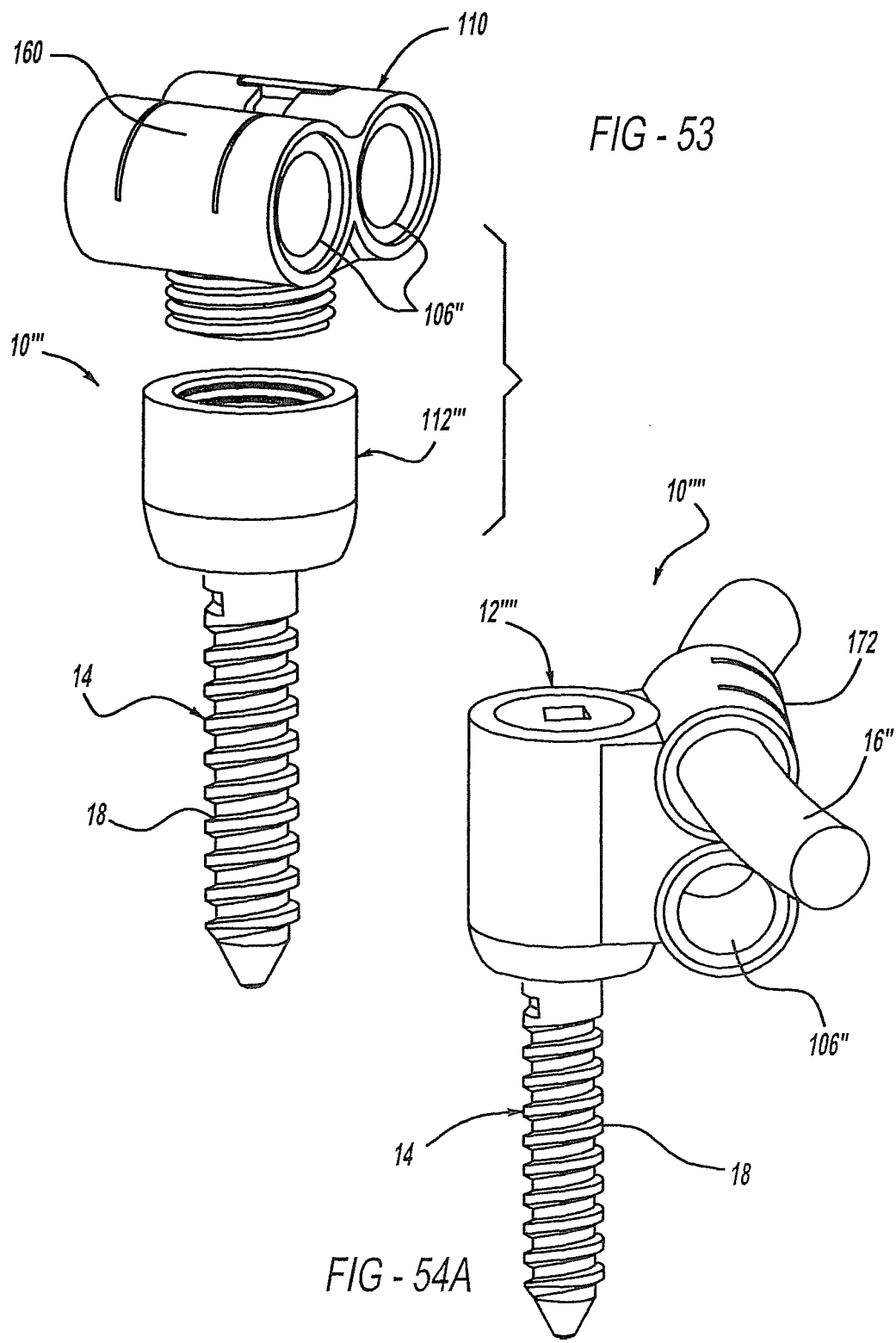
FIG. 53 is a side perspective view exploded of the present invention.
FIG. 54a is a side elevational view in perspective of a further embodiment of the present invention.
Figure 54B:
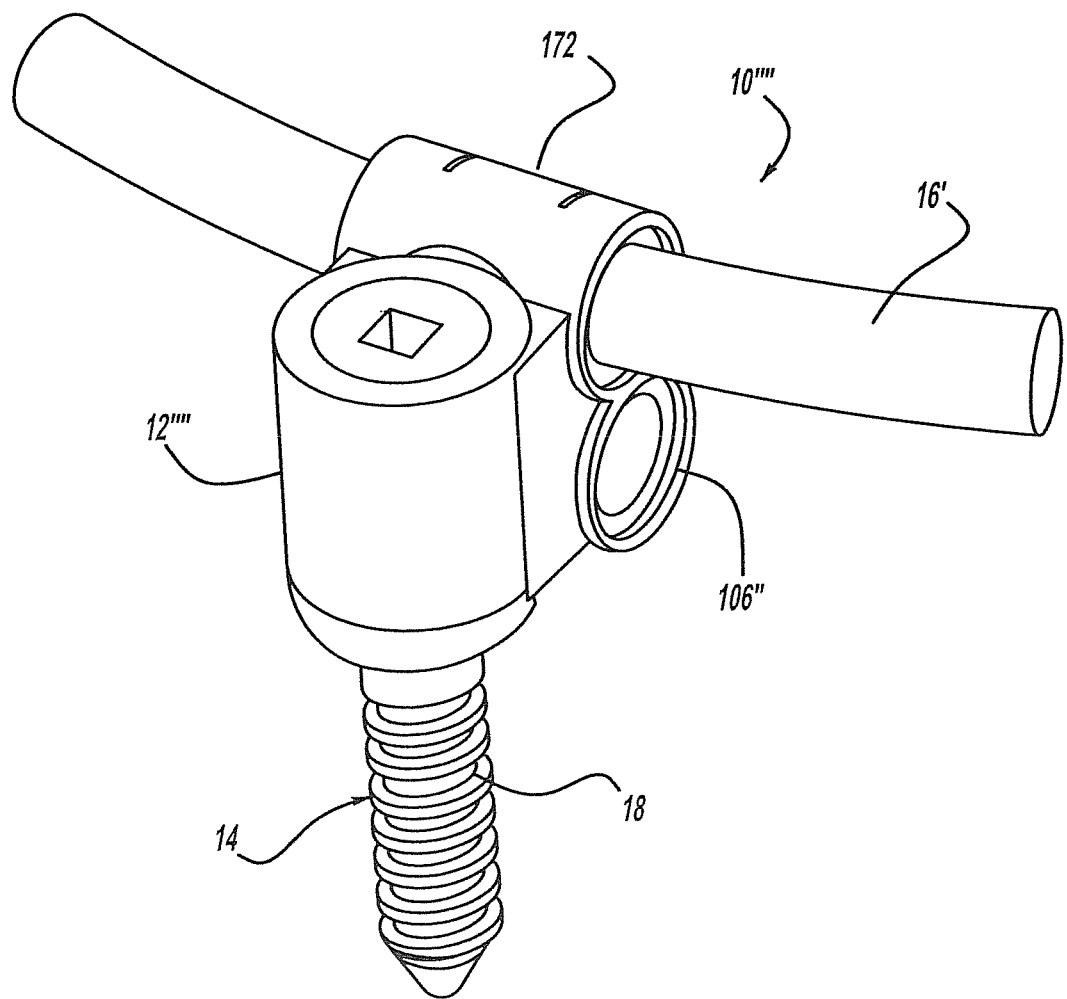

FIGS. 54*a* and 54*b* show a further version 10''' of the same concept described above. The body member 12'''' and bearing holder 172 are a single unit with rods 16' and bearings 106" disposed on the side of the body member 12''''. The polyaxial angulation is locking in the load sharing bearing by a locking means, such as a set screw. The rod and rod bearings are now parallel to the body. The rods can also be angled, such that the rods are at a 45° angle relative to the body. This reduces height for an increase in width, or vice versa.

FIGS. 55*a* and 55*b* show the assembly at multiple connecting points of the vertebrae. The left-hand figure shows the rods in the coronal plane while the right-hand figure shows the rods rotated during spinal adjustment in the sagital plane. A multi-segmented assembly is shown which allows for individual segmental adjustment along the assembly. Hence, segmental adjustments can be individually made during the surgical process. It should also be noted that excess rod 176 allows for sliding movement and thereby growth of the vertebrae adapting the present invention to a pediatric use.

Figure 56:
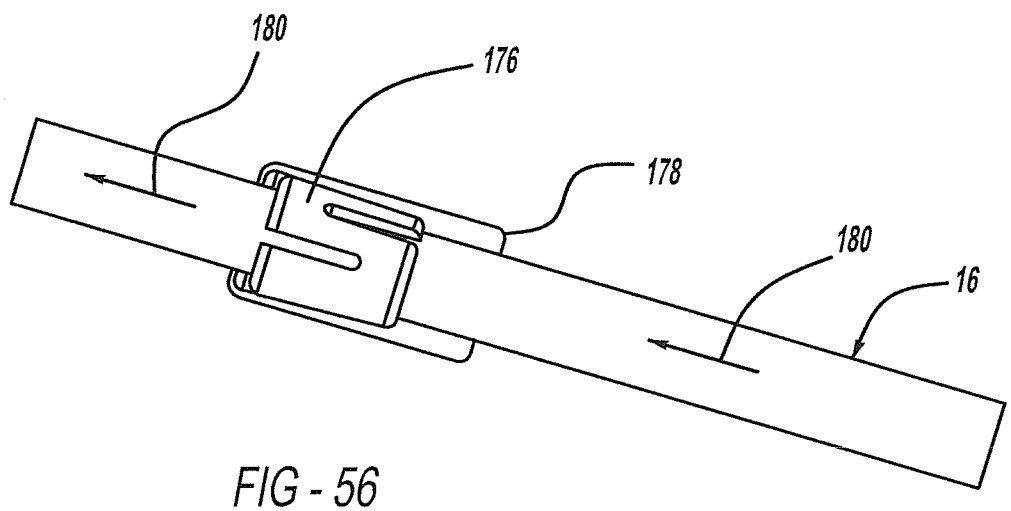
FIG. 56 is a side plan view line drawing of a slidable housing and collet on a rod.
Figure 57:
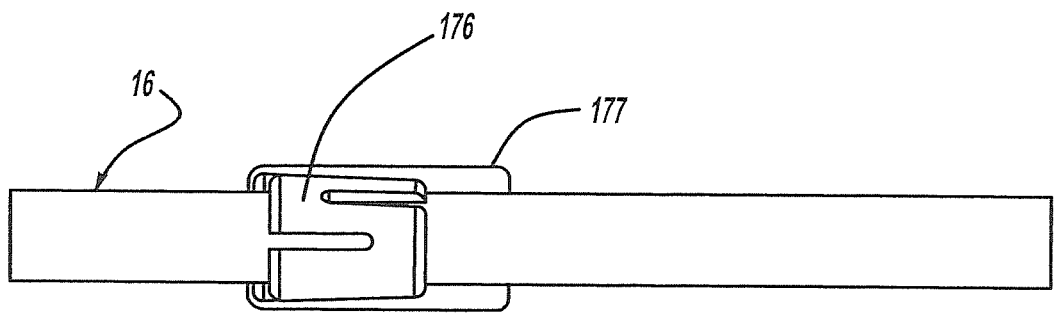
FIG. 57 is a plan view of the assembly shown in FIG. 56.

FIGS. 56 and 57 demonstrate the concept of a growing rod whereby a rod in pediatric scoliosis is forced in the direction of the growing spine to assist in curve correction. This general concept has been previously used wherein surgeons begin the growing rods program with patients at about 7 or 8 years old by attaching adjustable, stainless steel rods to the spine. These rods are fixed to the screws and locked to control the deformity and gradually expanded to straighten the spine while enabling it to grow as a result of periodic surgeries in which doctors lengthen the rods over several years. Although the novel invention disclosed within along with a sliding approach may eliminate the needs for such growing rods, it is very possible to utilize such rods within the present invention. In addition, the present invention provides a novel approach for doing this with higher strength materials than stainless steel.

As materials become higher strength, they often become more notch sensitive or subject to crack propagation from a stress riser. In stainless steel, which is less sensitive to this, a collet can be used that grabs features on the rod, such as indentations. As the body members 12 are advanced on the rod 16, the collet grabs another indentation. Ideally, with higher strength materials, it is not desirable to create indentations, but rather utilize smooth rods and still be able to index the rod in the direction of growth. Thus, the present invention provides means for grabbing the rod securely only in one direction while allowing the device to release the rod during the expansion process and relock after the expansion is completed.

In the preferred embodiment shown in FIGS. 56 and 57, a tapered collet 176 and a housing 178 is utilized. The collet 176 compresses securely against the rod 16 when the rod 16 is seated in the collet and the collet taper engages the taper in the housing 178. A gap towards the large end of the taper between the end of the collet 176 and the inside edge of the housing 178 allows the collet 176 to slide into this gap when forced to do so, thus freeing the tapers. The rod 16 is then relatively free (there is still friction which can be set at the time of manufacturing at different levels depending on what is ideal for the given surgical situation) to move in the direction shown by arrows 180 in FIG. 56. Backwards motion relocks the collet tapers thereby locking the assembly. An advantage to this is that very little motion is required to unlock and relock the tapers. The ideal taper is what is termed a self-releasing taper or greater than 3°, as anything less would be very hard to disengage.

In view of the above, the present invention provides a uniform loading system. Normal fixation in a single level screw fusion constructs involves using at least two rods, one on either side of the spine, and two screws per rod. As the screws are fixed rigidly to the rod and the pedicle, there is not adjustment if one screw incurs a higher stress than another. Curvature of the rods, anatomical alignment, variation of screw depth from side to side, and the addition of other components, such as cross links, all contribute to variations in stress. The higher the variation in stress, the more likely the highest stressed screw or component will fail. By allowing screws to load share and distribute the stresses in accordance with the present invention, this issue becomes greatly reduced and the loads to the assembly and spine are distributed more evenly.

Figure 58:
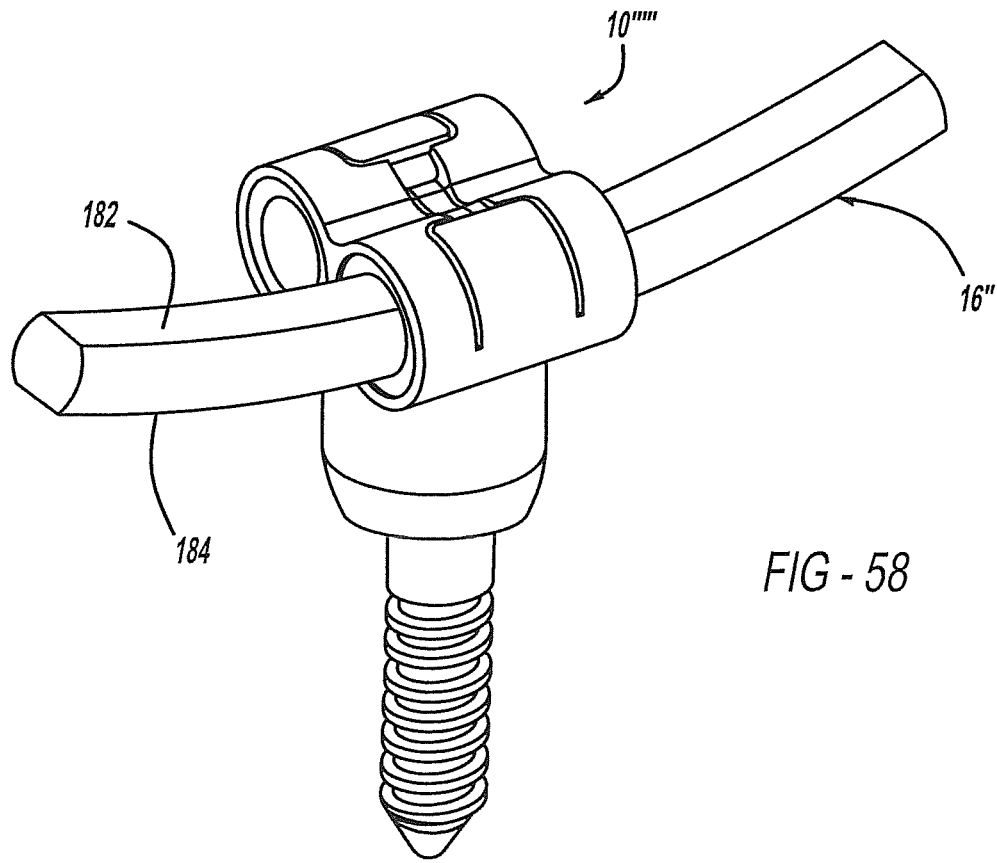
FIG. 58 is a perspective view of an alternative embodiment of the present invention.
Figure 59:
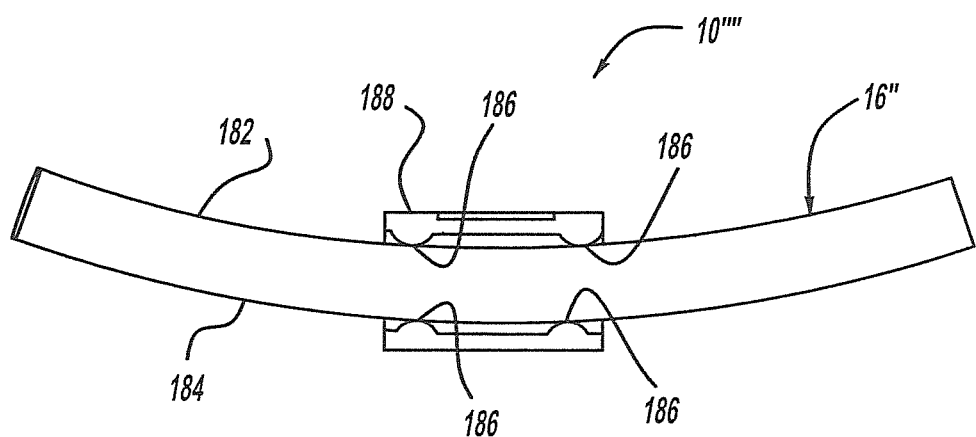
FIG. 59 is a cross-sectional view of the embodiment shown in FIG. 58.

A further embodiment of the present invention is shown in FIGS. 58 and 59 at 10''''''. In this embodiment, the rod member 16" includes at least two flat portions 182, 184. The rod is contacted by rounded bearing surfaces that allow for any degree of bend to occur with only one bearing housing. This is demonstrated in FIG. 59, in cross-section, wherein the contact points 186 of the bearing member 188 allow for curvature of the rod member 16" therebetween. Secondly, the stiffness of the rod 16" can be adjusted such that the stiffness in the coronal plane can be different than the sagital plane. For example, after derotation, it may be beneficial to have the stiffness of the rod 16" in the coronal plane but less stiff than the sagital plane. This would keep the spine straighter in the medial lateral direction but allow greater flexion anterior/posterior. In other words, selective flexion of the rod and thereby the system can be achieved in a desired plane while rigidity can be achieved in a different plane. Third, the height of the rod can be reduced to allow for a smaller height of the implant.

In operation, at least three screws would first be disposed across vertebral junctions. The middle screw would be the reference point for the attachment of the body members 12 and eventually the rods. Adjustment would be made first of the middle screw and then above and below the rod segment. Derotation would result in straightening of the spine. Sliding of the body members along the rods would allow for growth of the spine. The various locking means above would allow for one unidirectional rotation of the rods relative to the body members.

A further embodiment of a rod assembly made in accordance with the present invention is shown in FIGS. 60-71. As discussed above, the present invention as used for the treatment of scoliosis utilizes a single rod and dual rod devices, with the ability to use a dual barrel and bearing design to allow for mull rods to connect each double barrel. One rod runs from each screw assembly to the next one which staggers the rods up and down the construct. This allows these short length rods to effectively create one long rod while allowing for curve reduction incrementally one level at a time. This approach requires the dual bearing design to hold or couple two rods at each level. In other words, the interconnection is not directly between the rods, but rather at the body members that interconnect the rods to the screw members.

The embodiment shown in FIGS. 60-71 provide another approach to allow the short rods to interconnect with each other directly. This approach allows for a single bearing approach and smaller body size for interconnecting the rods to the body members, although it makes the rod per se larger in diameter and more sophisticated in construction.

Figure 60:
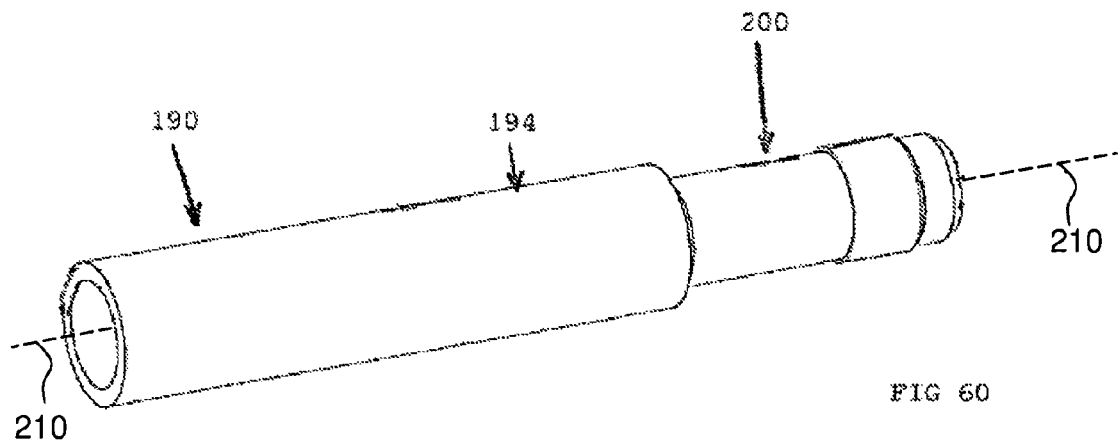
FIG. 60 is a perspective view of a rod member made in accordance with the present invention including a male portion.
Figure 61:
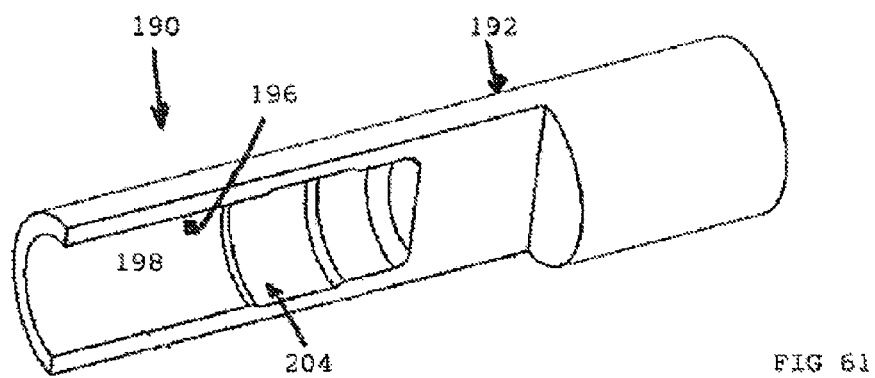
FIG. 61 is a perspective view, partially broken away, of a second rod portion including a female receiving end.

Generally, the embodiment provides an implant assembly generally shown at 190 including a first rod 192 as shown in FIG. 61 and a second rod 194 shown in FIG. 60. The first rod 192 includes an inner wall 196 defining a passageway 198 therein. The second rod 194 includes a neck portion 200 disposed within the passageway 198 for telescoping movement relative to the first rod 192. In other words, the first and second rods 192 and 194 are directly connected together, as opposed as being connected together through a body member as discussed above. The two rods have a telescoping connection between the neck portion 200 and the passageway 198 to allow for adjustment in length of the interconnected two rod assembly. Of course, each rod member could have at its opposite end another male portion or female portion (passageway) for interconnection to further rods along the length of an entire implant assembly.

Figure 62:
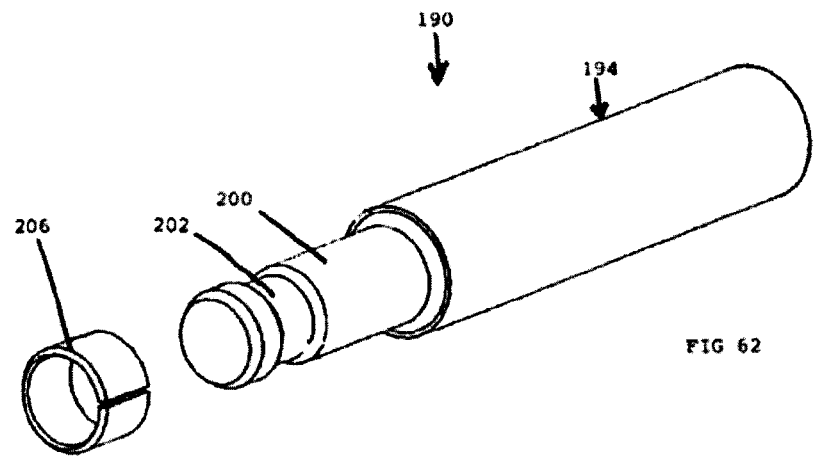
FIG. 62 is a perspective view of the rod member including the male portion and further including a retaining snap ring.

The rods 192 and 194 are interconnected by a retaining mechanism which retains the second rod 194 in at least one telescoped interconnected position relative to the first rod 192. Specifically, the neck portion 200 includes an annular recess 202 therein. The inner wall 196 of the rod member 192 also includes an annular recess 204 therein. The retaining mechanism includes a flexible snap ring 206, as shown in FIG. 62, disposed about one of the annular recesses 202, 204 for snapping engagement with the other of the recesses when the recesses are adjacently positioned as the second rod 194 telescopingly moves within the passageway 198 of the first rod 192, as shown assembled in FIG. 63. Either or both of the first and second rods 192, 194 can include multiple recesses to allow for differential extension or retraction of the length of the two rods 192, 194 and retention in various of the extended or retracted positions. Thus, the present invention provides herewith a direct rod joint connection that allows for length extension or shortening of a dual rod assembly.

Figure 63:
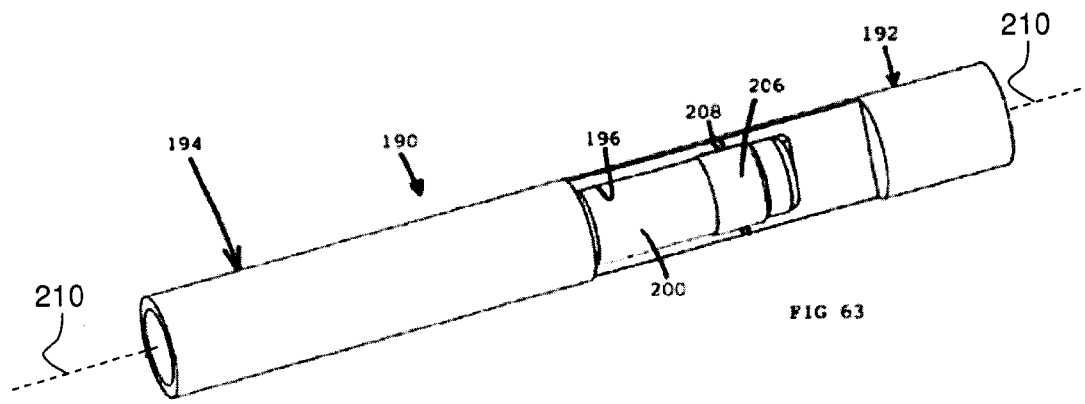
FIG. 63 is a perspective view partially broken away showing the assembled two rod portions.

As best shown in FIG. 63, the first rod 192 can include one or more small holes 208 to allow access through the rod 192 into the snap ring 206. A tool can then be used to compress the snap ring 206 to allow the two rod sections 192, 194 to be pulled apart or brought telescopingly together.

The assembly shown in FIGS. 60-63 include no rotation control of one rod relative to the other. Thus, one section can be rotated relative to the other independently of any other rod sections to allow for derotation of the spine level by level. Accordingly, the rods 192 and 194 can be straight rods or curved rods and straighter curved rods can be used in various sections selectively in a multiple rod assembly. Either or all of the rod members can rotate along the longitudinal axis 210 defined by the passageway 198, as best shown in FIG. 61, to allow for derotation of the spine level by level.

Figure 64:
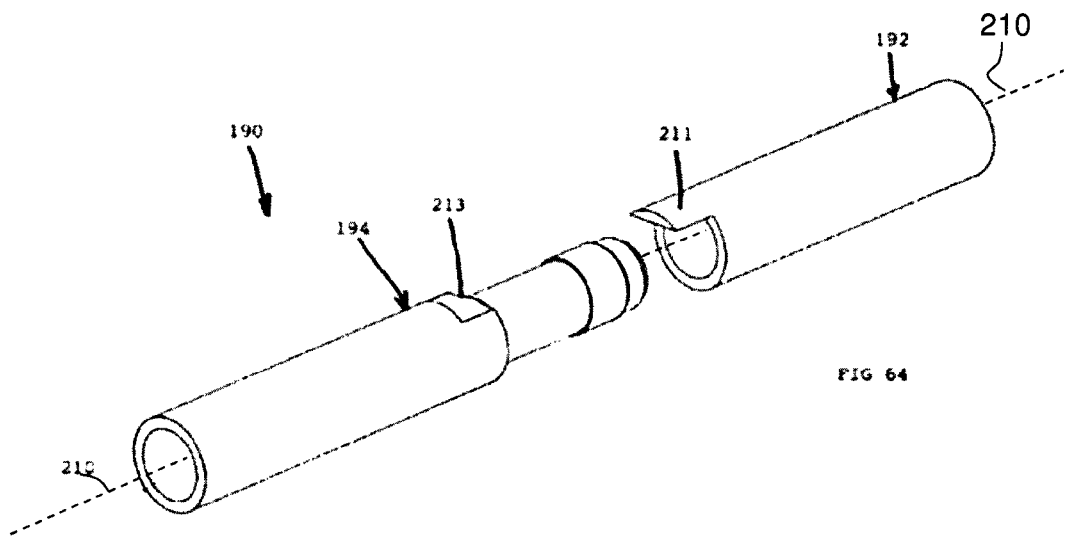
FIG. 64 is an exploded view of the two rod portions further including rotational control means.
Figure 65:
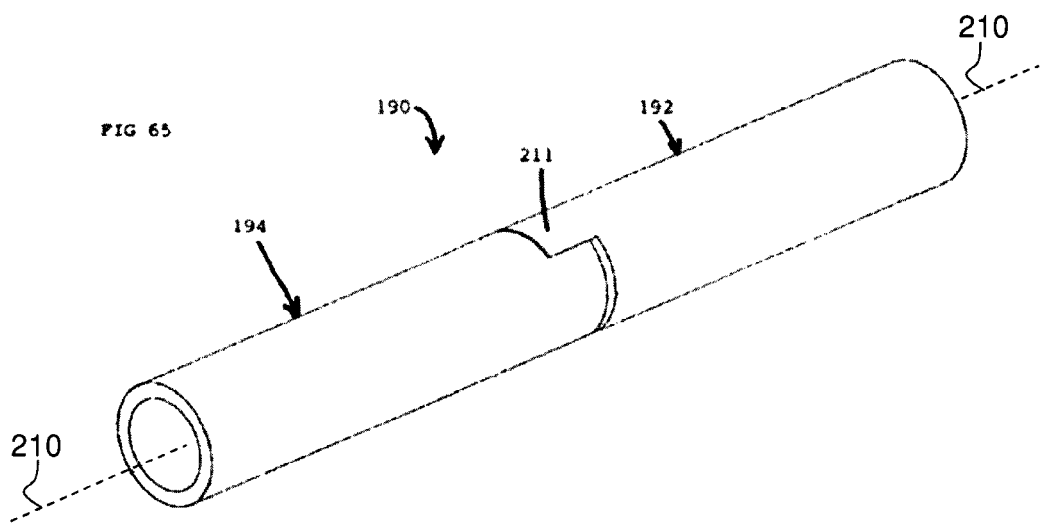
FIG. 65 is an assembled version of the two rod portions including the rotational control means.

FIGS. 64 and 65 show a mechanism for controlling relative rotation between the first and second rods 192, 194. More specifically, the rotation control mechanism includes a tab portion 211 extending from the first rod 192 along a longitudinal axis 210 defined by the passageway 198 as shown in FIG. 64 and a recess 210, as best shown in FIG. 64, extending into a recess 213, the second rod 194 for mating engagement with the tab 211 such that when one of the rods turn in the longitudinal axis 210, the other of the rods turn along the same axis. Of course, either rod 192 or 194 could include the tab 211 or recess 213 and the combination could include multiple tabs and recesses to provide further stability to prevent relative rotation therebetween.

In a multiple rod assembly, various of the rods could include the tabs and recesses 211, 213 to prevent rotation at different junctions of the assembly while other portions could include the interconnection shown in FIGS. 60-63. Accordingly, selective rotation can be chosen by the surgeon implanting the device at different levels of the spine where such rotation is needed while areas not requiring derotation can be fixed along the longitudinal axis 210.

Figure 66:
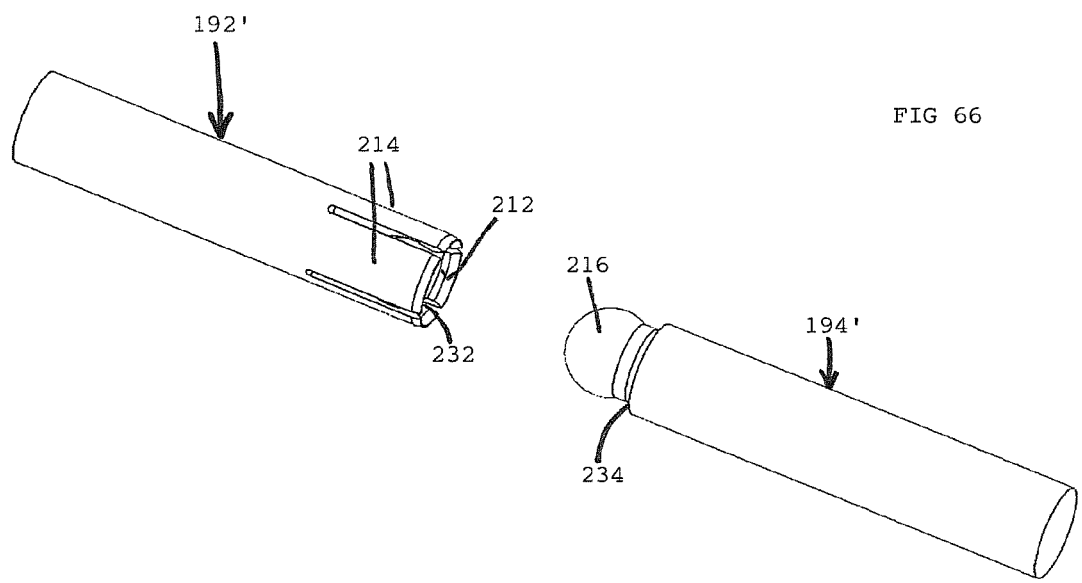
FIG. 66 is an exploded, perspective view of two rod portions including a spherical seat and socket connection.

FIGS. 66-69 show an alternative interconnection between first rod 192' and second rod 194'. The interconnection shown in FIGS. 66-68 allow for total pivoting connection for interconnecting the first and second rods 192' and 194' and allowing pivoting movement therebetween. As best shown in FIG. 66, the first rod member 192' includes a socket 212 disposed within outwardly flexible arms 214. Second rod 194' includes a spherical end portion 216 which can be snap fit and then engaged within socket 212. This interconnection allows for pivoting movement between the two rods, limited by the range of motion mechanism allowing for full or limiting range of relative motion between the first and second rods 192, 192', 194, 194' while maintaining a consistent total interconnected length of the first and second rods. This mechanism is described in further detail below.

Figure 67:
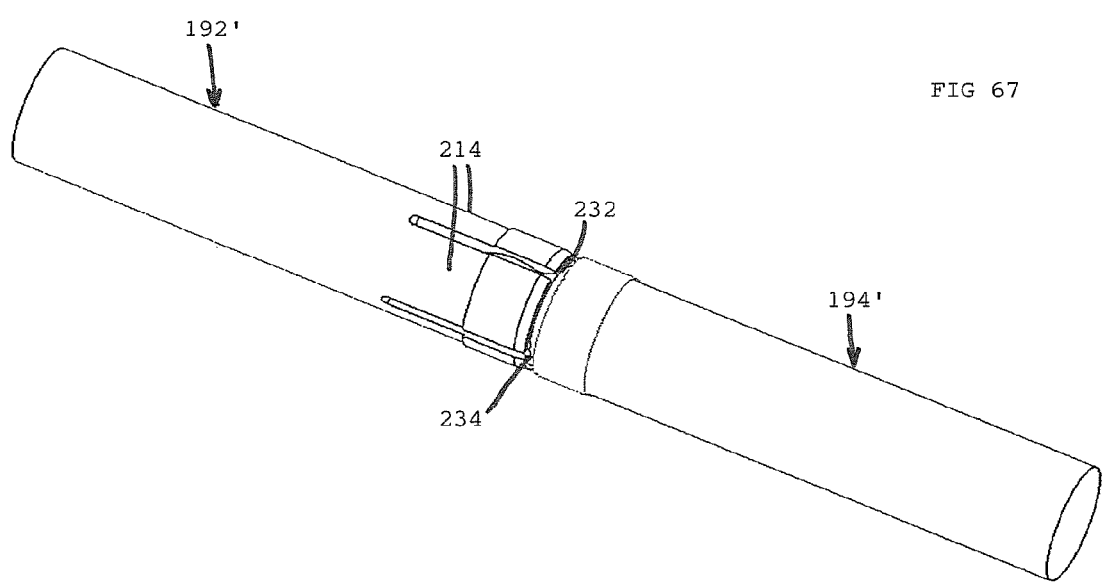
FIG. 67 is an assembled view of the two rod portions of FIG. 66.
Figure 68:
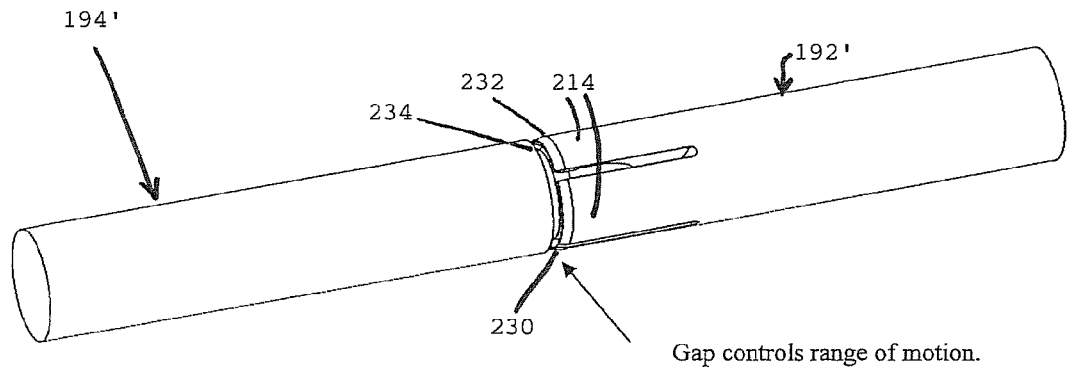
FIG. 68 is a perspective assembled view of the two rod portions including the spherical seat and socket demonstrating the gap between the rods controlling the range of motion between the two rods.
Figure 69:
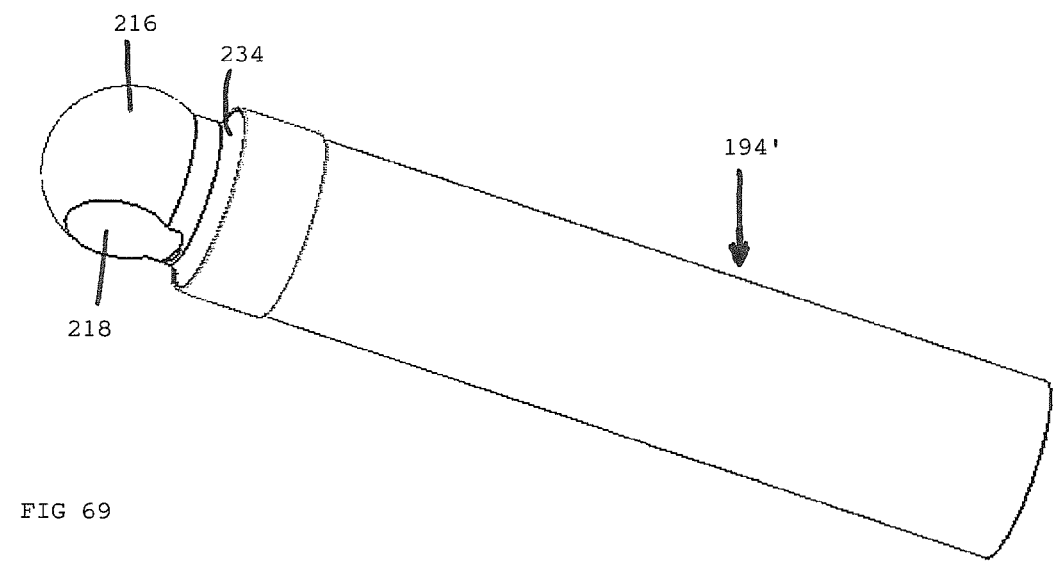
FIG. 69 is an enlarged perspective view of the rod portion including the spherical portion further including means for limiting rotation of the rod portion relative to the other rod portion.
Figure 70:
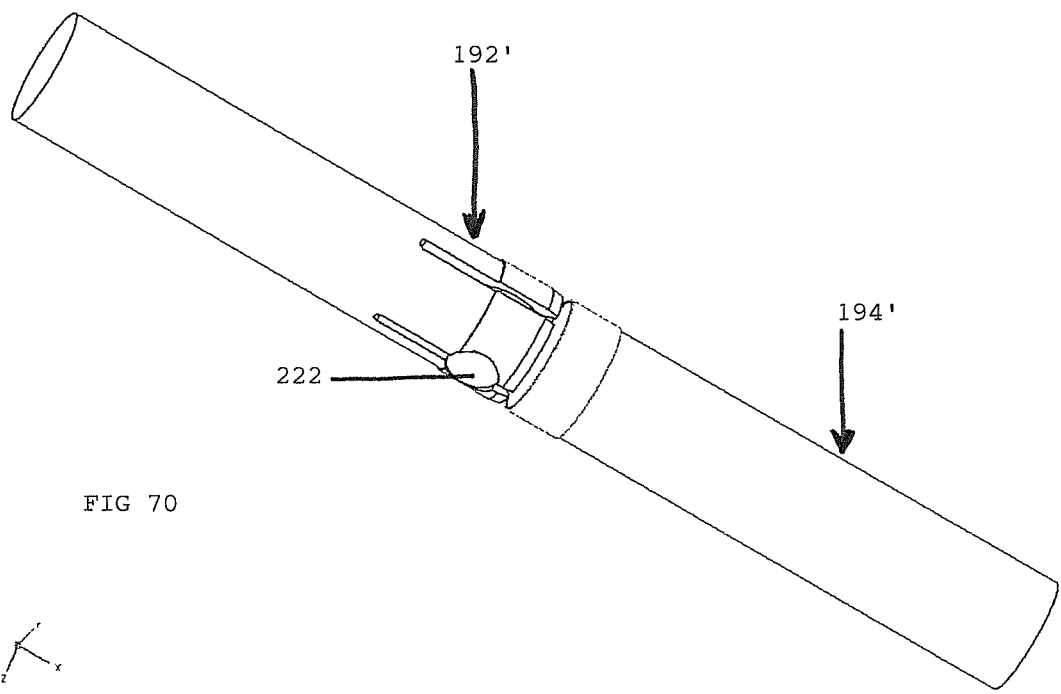
FIG. 70 is an assembled perspective view of the two rod portions further including means for preventing relative rotation in a single plane.
Figure 71:
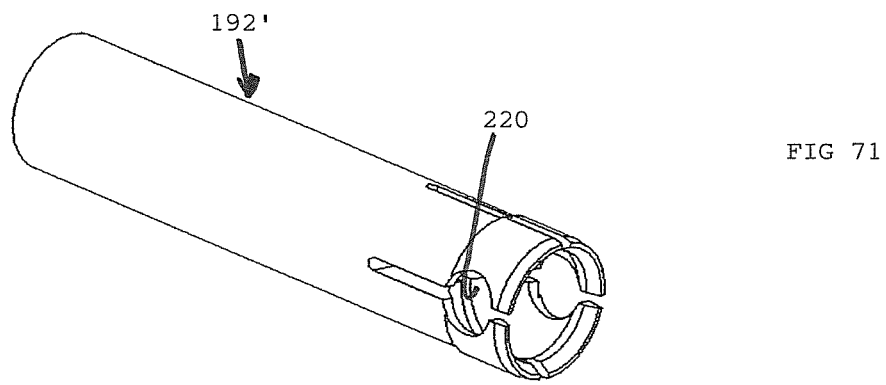
FIG. 71 is a perspective view of a rod portion including the female seat and pin type socket.

The retaining ball and socket mechanism shown in FIGS. 66-68 can further include a pivot restricting mechanism for limiting pivoting movement between the first and second rods 192' 194' to a single plane at the rod joint. The pivot restricting mechanism includes at least one flat 218 on the surface of the spherical end portion 216 for engaging a flat portion within the socket 212 (not shown). The engagement of the flats between the spherical portion 216 and the socket 212 limit pivoting movement to a single plane. An alternative embodiment of a mechanism for limiting the pivoting movement is shown in FIGS. 70 and 71. The mechanism includes a hole 220 extending through the spherical socket, as best shown in FIG. 71 and further extending through the spherical end portion. A pin member 222 extends through the openings defining a hinged portion of the rod joint. The transverse pin 222 is used as a connection mechanism such that the transverse pin snaps into the hole 220 in the socket portion 212. This simple pin connection provides a hinge. If the pin 212 has clearance in the hole 220 in either the socket 212 on the spherical surface 216, it can allow rotation around the sphere to the extent that the pin is capable while allowing one rod to control the other rod during derotation.

As best shown in FIG. 68, the rod joint assembly includes a range of motion limiting mechanism. This can be obtained by a gap 230 between an end portion 232, 234 of each of the rods 192, 194 when interconnected. The amount of the gap 230 defines a range of motion between the first and second rods 192, 194. That is, the greater the gap, the greater the range of motion between the two rods.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

The invention claimed is:

1. An implant assembly, comprising:
a first rod including an inner wall defining a first passageway therein, the first rod having a first end and a second end, the passageway of the first rod accessible from the second end of the first rod;
a first polyaxial screw having a first rod retainer, the rod retainer retaining the first end of the first rod;
at least one intermediate rod, the at least one intermediate rod telescopically disposed within the first passageway of the first rod for movement relative to the first rod, the first rod and the at least one intermediate rod configured to be retained in one of multiple telescoping positions, the at least one intermediate rod including an inner wall defining a second passageway therein;
a second rod having a first end and a second end, the first end of the second rod telescopically disposed within the second passageway of the at least one intermediate rod for movement relative to the at least one intermediate rod, the at least one intermediate rod and the second rod configured to be retained in one of multiple telescoping positions;
a retaining mechanism that retains the at least one intermediate rod in at least one telescoped interconnection position relative to the first rod, the retaining mechanism comprising a first flexible ring member disposed about one of an annular recess of the first rod and an annular recess of the at least one intermediate rod;
a retaining mechanism that retains the second rod in at least one telescoped interconnection position relative to the at least one intermediate rod, the retaining mechanism comprising a second flexible ring member disposed about one of an annular recess of the at least one intermediate rod and an annular recess of the second rod;
the first rod and the at least one intermediate rod having a telescoping connection that allows for and limits a range of relative motion between the first rod and at least one intermediate rod while maintaining a consistent total interconnected length of the first rod and the at least one intermediate rod, the first flexible ring member being compressible and allowing the first rod and the at least one intermediate rod to be pulled telescopingly apart and brought telescopingly together by adjusting a compression of the first flexible ring member;
the at least one intermediate rod and the second rod having a telescoping connection that allows for and limits a range of relative motion between the at least one intermediate rod and the second rod while maintaining a consistent total interconnected length of the at least one intermediate rod and the second rod, the second flexible ring member being compressible and allowing the at least one intermediate rod and the second rod to be pulled telescopingly apart and brought telescopingly together by adjusting a compression of the second flexible ring member; and
a second polyaxial screw having a second rod retainer, the second rod retainer retaining the second end of the second rod.

2. The implant assembly according to claim 1, wherein the telescoping connection includes a neck portion having an outer surface engaging the inner wall of the first rod to limit pivoting movement therebetween.

3. The implant assembly according to claim 2, wherein:
the neck portion includes one or more annular recesses disposed on the second rod and the inner wall of the first rod includes one or more annular recesses disposed on the first rod; and
the flexible ring member is disposed about one of the one or more annular recesses for snap-in engagement with the other of the one or more recesses when the recesses are adjacently positioned as the second rod telescopingly moves within the first passageway of the first rod.

4. The implant assembly according to claim 3, wherein at least one of the first and second rods includes a plurality of the annular recesses for retaining the first and second rods at the multiple telescoping positions relative to each other.

5. The implant assembly according to claim 3, wherein the first rod includes at least one opening extending therethrough from an outer surface to the inner wall at the annular recess allowing for access to compress the flexible ring member and release the first and second rods from the retaining mechanism.

6. The implant assembly according to claim 1, wherein at least one of the first and second rods are straight rods.

7. The implant assembly according to claim 1, wherein at least one of the first and second rods are curved.

8. The implant assembly according to claim 7, wherein at least one of the first and second rod members rotates along a longitudinal axis defined by the respective one of the first and second passageways to allow for deterioration of a spine level by level.

9. The implant assembly according to claim 1, further comprising a compression tool that adjusts the compression of at least one of the first and second flexible ring members.

10. The implant assembly according to claim 1, further comprising a third rod member including an inner wall defining a passageway therethrough in telescoping engagement with the second rod, the second rod including a third portion opposite the first rod, the third portion being disposed for telescoping movement relative to the third rod.

11. The implant assembly according to claim 1, wherein:
the second rod has a first end and a second end; and
the first end of the second rod is telescopically disposed within the first passageway.

* * * * *